(12) United States Patent
Mufti et al.

(10) Patent No.: US 8,900,805 B2
(45) Date of Patent: Dec. 2, 2014

(54) QUENCHING METHODS FOR RED BLOOD CELL PATHOGEN INACTIVATION

(75) Inventors: Naheed Mufti, San Ramon, CA (US); Anna Erickson, Richmond, CA (US); Anne North, Pleasant Hill, CA (US)

(73) Assignee: Cerus Corporation, Concord, CA (US)

( * ) Notice: Subject to any disclaimer, the term of this patent is extended or adjusted under 35 U.S.C. 154(b) by 857 days.

(21) Appl. No.: 12/936,763

(22) PCT Filed: Apr. 9, 2009

(86) PCT No.: PCT/US2009/040032
§ 371 (c)(1),
(2), (4) Date: Jan. 25, 2011

(87) PCT Pub. No.: WO2009/126786
PCT Pub. Date: Oct. 15, 2009

(65) Prior Publication Data
US 2011/0286987 A1    Nov. 24, 2011

Related U.S. Application Data

(60) Provisional application No. 61/043,666, filed on Apr. 9, 2008, provisional application No. 61/087,034, filed on Aug. 7, 2008.

(51) Int. Cl.
| | |
|---|---|
| *A01N 1/02* | (2006.01) |
| *A01N 1/00* | (2006.01) |
| *A61L 2/16* | (2006.01) |
| *A61K 35/18* | (2006.01) |
| *A01N 43/42* | (2006.01) |
| *A61L 2/00* | (2006.01) |
| *A61K 35/00* | (2006.01) |

(52) U.S. Cl.
CPC .............. *A61K 35/18* (2013.01); *A01N 1/0215* (2013.01); *A01N 1/0226* (2013.01); *A61L 2/0082* (2013.01); *A01N 43/42* (2013.01); *A01N 1/02* (2013.01); *A61K 35/00* (2013.01)
USPC .................. 435/2; 422/28; 435/1.1

(58) Field of Classification Search
None
See application file for complete search history.

(56) References Cited

U.S. PATENT DOCUMENTS

| | | | |
|---|---|---|---|
| 2,402,665 | A | 6/1946 | Pepper at al. |
| 4,252,645 | A | 2/1981 | Marconi et al. |
| 4,337,269 | A | 6/1982 | Berke et al. |
| 4,727,027 | A | 2/1988 | Wiesehahn et al. |
| 4,748,120 | A | 5/1988 | Wiesehahn et al. |
| 4,944,920 | A | 7/1990 | Rubinstein |
| 4,971,760 | A | 11/1990 | Rubinstein |
| 5,055,485 | A | 10/1991 | Geacintov et al. |
| 5,094,960 | A | 3/1992 | Bonomo |
| 5,120,649 | A | 6/1992 | Horowitz et al. |
| 5,232,844 | A | 8/1993 | Horowitz et al. |
| 5,281,579 | A | 1/1994 | Estep |
| 5,418,130 | A | 5/1995 | Platz et al. |
| 5,559,250 | A | 9/1996 | Cook et al. |
| 5,587,490 | A | 12/1996 | Goodrich, Jr. et al. |
| 5,591,350 | A | 1/1997 | Piechocki et al. |
| 5,601,730 | A | 2/1997 | Page et al. |
| 5,637,451 | A | 6/1997 | Ben-Hur et al. |
| 5,658,722 | A | 8/1997 | Margolis-Nunno et al. |
| 5,660,731 | A | 8/1997 | Piechocki et al. |
| 5,691,132 | A | 11/1997 | Wollowitz et al. |
| 5,753,258 | A | 5/1998 | Schreier et al. |
| 6,093,725 | A | 7/2000 | Cook et al. |
| 6,136,586 | A | 10/2000 | Budowsky |
| 6,143,490 | A | 11/2000 | Cook et al. |
| 6,150,109 | A | 11/2000 | Edson et al. |
| 6,171,777 | B1 | 1/2001 | Cook et al. |
| 6,177,441 | B1 | 1/2001 | Cook et al. |
| 6,270,952 | B1 | 8/2001 | Cook et al. |
| 6,410,219 | B1 | 6/2002 | Cook et al. |
| 6,514,987 | B1 | 2/2003 | Cook et al. |
| 6,544,727 | B1 | 4/2003 | Hei |
| 6,617,157 | B1 | 9/2003 | Budowsky et al. |
| 6,709,810 | B2 | 3/2004 | Cook et al. |
| 6,951,713 | B2 | 10/2005 | Hei et al. |
| 7,037,642 | B2 | 5/2006 | Hei |
| 7,293,985 | B2 | 11/2007 | Cook et al. |
| 7,655,392 | B2 | 2/2010 | Stassinopoulos |
| 2001/0009756 | A1 | 7/2001 | Hei et al. |
| 2002/0045228 | A1 | 4/2002 | Hei et al. |
| 2002/0182581 | A1 | 12/2002 | Cook et al. |
| 2002/0192632 | A1 | 12/2002 | Hei et al. |

(Continued)

FOREIGN PATENT DOCUMENTS

| | | |
|---|---|---|
| EP | 0 352 076 A2 | 1/1990 |
| EP | 0 352 076 A3 | 1/1990 |
| EP | 0 352 076 B1 | 1/1990 |
| EP | 0 457 196 A2 | 11/1991 |
| EP | 0 457 196 A3 | 11/1991 |
| EP | 0 457 196 B1 | 11/1991 |
| EP | 0 641 796 A1 | 3/1995 |
| JP | 2007-262075 A | 10/2007 |
| WO | WO-95/00631 A1 | 1/1995 |
| WO | WO-96/02838 A1 | 2/1996 |

(Continued)

OTHER PUBLICATIONS

Hess et al. "Buffering and dilution in red blood cell storage", Transfusion 46: 50-54, 2006.*

(Continued)

*Primary Examiner* — Ruth Davis
*Assistant Examiner* — Emily Cordas
(74) *Attorney, Agent, or Firm* — Morrison & Foerster LLP

(57) ABSTRACT

The present invention provides improved methods for treating red blood cell compositions with a pathogen-inactivating compound under conditions which provide suitable pathogen inactivation while maintaining cell vitality. Also provided methods of reducing dehydration in red blood cells, as well as treated red blood cell compositions.

77 Claims, 7 Drawing Sheets

(56) References Cited

U.S. PATENT DOCUMENTS

| | | | |
|---|---|---|---|
| 2003/0073650 A1* | 4/2003 | Reddy et al. .................. 514/43 |
| 2003/0113704 A1 | 6/2003 | Stassinopoulous et al. |
| 2004/0029897 A1 | 2/2004 | Cook et al. |
| 2004/0081956 A1 | 4/2004 | Lockerbie et al. |
| 2004/0180321 A1 | 9/2004 | Cook et al. |
| 2004/0185544 A9 | 9/2004 | Hei |
| 2005/0142542 A1 | 6/2005 | Hei et al. |
| 2006/0115466 A1 | 6/2006 | Stassinopulos |

FOREIGN PATENT DOCUMENTS

| | | |
|---|---|---|
| WO | WO-96/09846 A1 | 4/1996 |
| WO | WO-96/14737 A1 | 5/1996 |
| WO | WO-96/39816 A1 | 12/1996 |
| WO | WO-96/39818 A1 | 12/1996 |
| WO | WO-96/40857 A1 | 12/1996 |
| WO | WO-97/02028 A1 | 1/1997 |
| WO | WO-97/07674 A1 | 3/1997 |
| WO | WO-97/16966 A1 | 5/1997 |
| WO | WO-97/18844 A1 | 5/1997 |
| WO | WO-98/30545 A1 | 7/1998 |
| WO | WO-99/34839 A1 | 7/1999 |
| WO | WO-00/50026 A1 | 8/2000 |
| WO | WO-01/91775 A2 | 12/2001 |
| WO | WO-01/91775 A3 | 12/2001 |
| WO | WO-2006/050328 A1 | 5/2006 |
| WO | WO 2006050328 A1 * | 5/2006 |

OTHER PUBLICATIONS

VanDelinder et al. "Separation of plasma from whole human blood in a continuous cross-flow in a molded microfluidic device", Analytical Chemistry 78(11): 3765-3771, 2006.*

Sward-Nilsson et al. "In Vitro Quality of Red Blood Cells Obtained After Automated Separation of Whole Blood by the Atreus 2C+ System and Stored for 42 Days", Vox Sanguinis 91 (Suppl. 3): 308, 2006.*

Waitumbi et al. "Age-related changes in red blood cell complement refulatory proteins and susceptibly to severe malaria", Journal of Infectious Disease 190: 1183-91, 2004.*

US 6,331,387, 12/2001, Hei. (withdrawn).

Aejmelaeus, R. et al. (1996). "Is There an Unidentified Defense Mechanism Against Infection in Human Plasma," *FEBS Letters* 384:128-130.

Al-Harbi, M.M. et al. (1997). "Gentamycin and Cyclosporine Increase Total Soluble Thiols in the Plasma and Lymphocytes of Rats and Perturb Erythrocyte Fragility," *Med. Sci. Res.* 25:155-157.

Anonymous. (1971). "Special Reagents for Thiol Groups," *Aldrichimica Acta* 4(3): 33-35.

Anonymous. (1971). "Special Reagents for Thiol Groups," *Aldrichimica Acta* 4(3): 46-48.

Anonymous. (2003). "Helinx® Technology Inactivates Human T-Cell Leukemia Virus (HTLV I/II) in Human Red Blood Cells," Abstract *presented at: American Association of Blood Banks (AABB)*, 56th Annual Meeting, Nov. 1-4, 2003, located at <http://www.cerus.com/index.cfm/abstracts/2003/Helinx174TechnologyInactivatesHumanTCellLeukemiaVirus-H . . . >, last visited on Jan. 8, 2007, two pages.

Anonymous. (2003). "Helinx® Technology Inactivates Pathogens of Emerging Importance in Red Blood Cell Concentrates," Abstract *presented at: American Society of Hematology (ASH)*, 45th Annual Meeting, Dec. 6-9, 2003, located at <http://www.cerus.com/index.cfm/abstracts/2003/Helinx174TechnologyInactivatesPathogensofEmerging Impor . . . >, last visited on Jan. 8, 2007, two pages.

Anonymous. (2003). "Treatment with Helinx® Technology Does Not Affect the Ability of Red Blood Cells to Overcome Oxidative Stress," Abstract *presented at: American Association of Blood Banks (AABB)*, 56th Annual Meeting, Nov. 1-4, 2003, located at <http://www.cerus.com/index.cfm/abstracts/2003/TreatmentwithHelinx174TechnologyDoesNotAffecttheAbilit . . . >, last visited on Jan. 8, 2007, two pages.

Anonymous. (2004). "Antibody Formulation to S-303-Treated RBCs in Setting of Chronic RBC Transfusion," Abstract *presented at:American Society of Hematology (ASH)*, 46th Annual Meeting, Dec. 4-7, 2004, located at <http://www.cerus.com/index.cfm/abstracts/2004/AntibodyFormulationtoS303TreatedRBCsinSettingofChronic . . . >, last visited on Jan. 8, 2007, two pages.

Anonymous. (2004). "Elimination of Immunoreactivity of Red Cells Treated with a Modified S-303 Pathogen Inactivation Process," Abstract *presented at: American Society of Hematology (ASH)*, 46th Annual Meeting, Dec. 4-7, 2004, located at <http://www.cerus.com/index.cfm/abstracts/2004/EliminationofImmunoreactivityofRedCellsTreatedwithaMod . . . >, last visited on Jan. 8, 2007, two pages.

Anonymous. (2004). "Transfusion of S-303 Treated RBCs to Treat Acute Anemia During or Following Cardiac Surgery: Results of a Phase III Trial," Abstract *presented at:American Society of Hematology (ASH)*, 46th Annual Meeting, Dec. 4-7, 2004, located at <http://www.cerus.com/index.cfm/abstracts/2004/TransfusionofS303TreatedRBCsToTreatAcuteAnemiaduringor . . . >, last visited on Jan. 8, 2007, two pages.

Anonymous. (Dec. 3, 2004). "Cerus Corporation and Collaborators to Present at American Society of Hematology Meeting," *Press Release, Cerus Corporation*, located at <http://www.cerus.com/index.cfm/News/Press_Release_Archive?Year=2007&NID=8 . . . >, last visited on Jan. 8, 2007, four pages.

Awasthi, Y.C. et al. (Dec. 28, 1984). "Purification and Characterization of a New Form of Glutathione S-Transferase from Human Erythrocytes," *Biochemical and Biophys. Res. Commun.* 125(3):1053-1060.

Baxt, B. et al. (1976). "Mechanisms of Vesicular Stomatitis Virus-Induced Cytopathic Effects," *Virology* 72:383-392.

Begleiter, A. et al. (1996). "Chlorambucil in Chronic Lymphocytic Leukemia: Mechanism of Action," *Leukemia and Lymphoma* 23:187-201.

Beutler, E. et al. (Jun. 1982). "The Osmotic Fragility of Erythrocytes After Prolonged Liquid Storage and After Reinfusion," *Blood* 59(6):1141-1147.

Bolton, M.G. et al. (May 1991). "Specificity of Isozymes of Murine Hepatic Gluthathione *S*-Transferase for the Conjugation of Glutathione with L-Phenylalanine Mustard," *Cancer Research* 51:2410-2415.

Bolton, M.G. et al. (1993). "Kinetic Analysis of the Reaction of Melphalan with Water, Phosphate, and Glutathione," *Drug Metab. Dispos.* 21:986-996.

Bonadonna, G. et al. (1964). "Protection Studies with Sodium Thiosulfate Against Methyl bis(J-Chloroethyl)amine Hydrochloride (HN2) and its Ethylenimonium Derivative," *Clin. Pharm. & Thera.* 6(1):50-64.

Budowsky, E.I. et al. (1996). "Principles of Selective Inactivation of the Viral Genome: Dependence of the Rate of Viral RNA Modification on the Number of Protonizable Groups in Ethyleneimine Oligomers," *Vaccine Res.* 5(1):29-39.

Castro, G.M. et al. (2005). "A Modified S-303 Pathogen Inactivation Process Eliminates Immunoreactivity of S-303 RBC Detected in Pivotal Clinical Trials," *presented at the: European Hematology Association(ASH)*, $10^{th}$ Congress, Stockholm, Sweden, Jun. 2-5, 2005, sixteen pages.

Chong, Y. et al. (1990). "Evaluation of Thiol Borth for the Culture of *Salmonella typhi* and Other Bacteria from Blood," *Yonsei Medical Journal* 31(2):163-167.

Colvin, M. et al. (Mar. 1976). "Alkylating Properties of Phosphoramide Mustard," *Cancer Res.* 36:1121-1126.

Colvin, O.M. et al. (1993). "Role of Glutathione in Cellular Resistance to Alkylating Agents," *Adv. Enzyme Regul.* 33:19-26.

Danon, D. et al. (Oct. 1964). "Determination of Density Distriution of Red Cell Population," *J Lab Clin Med* 64(4):668-674.

Davey, R.J. et al. (1992). "The Effect of Prestorage Irradiation on Posttransfusion Red Cell Survival," *Transfusion* 32(6):525-528.

(56) References Cited

OTHER PUBLICATIONS

Dern, R.J. et al. (1967). "Studies on the Preservation of Human Blood. II. The Relationship of Erythrocyte Adenosine Triphosphate Levels and other in Vitro Measures to Red Cell Storageability," *J. Lab & Clin Med* 69(6):968-978.

Dirr, H. et al. (1994). "X-Ray Crystal Structures of Cytosolic Glutathione S-Transferases: Implications for Protein Architecture, Substrate Recognition and Catalytic Function," *Eur. J. Biochem* 220:645-661.

Dirven, H.A.A.M. et al. (Mar. 1996). "Glutathione Conjugation of Alkylating Cytostatic Drugs with a Nitrogen Mustard Group and the Role of Glutathione S-Transferases," *Chem. Res. Toxicol.* 9(2):351-360.

Dirven, H.A.A.M. et al. (Apr. 15, 1995). "The Role of Human Glutathione S-Tranferases Isoenzymes in the Formation of Glutathione Conjugates of the Alkylating Cytostatic Drug Thiotepa," *Cancer Res.* 55:1701-1706.

Dorr, R.T. (Feb. 1991). "Chemoprotectants for Cancer Chemotherapy," *Semin. Oncol.* 18(1-Suppl.2):48-58.

Dulik, D.M. et al. (1990). "Characterization of Glutathione Conjugates of Chlorambucil by Fast Atom Bombardment and Thermospray Liquid Chromatography/Mass Spectrometry," *Biomed Environ Mass Spectrom* 19:248-252.

Dulik, D.M. et al. (Oct. 1, 1986). "Characterization of Melphalan-Glutathione Adducts Whose Formation is Catalyzed by Glutathione Transferases," *Biochem Pharmacol.* 35(19):3405-3409.

Dulik, D.M. et al. (1987). "Conversion of Melphalan to 4-(Glutathionyl)Phenylalanine. A Novel Mechanism for Conjugation by Glutathione-S-tranferases," *Drug Metab. Dispos.* 15(2):195-199.

Fasth, A. et al. (1973). "Protective Effect of Thiosulfate and Metabolic Thiosulfate Precursors Against Toxicity of Nitrogen Mustard ($HN_2$)," *Biochem Pharmacology* 22:1337-1351.

Gamcsik, M.P. et al. (1997). "Kinetics of the Conjugation of Aniline Mustards with Glutathione and Thiosulfate," *Chem. Biol. Interact.* 105:35-52.

Gao, X. et al. (1991). "A Novel Cationic Liposome Reagent for Efficient Transfection of Mammalian Cells," *Biochem. Biophys. Res. Commun.* 179(1):280-285.

Gao, X. et al. (1993). "Cytoplasmic Expression of a Reporter Gene by Co-Delivery of T7 RNA Polymerase and T7 Promoter Sequence with Cationic Liposomes," *Nucleic Acids Res.* 21(12):2867-2872.

Gao, X. et al. (1996). "Potentiation of Cationic Liposome-Mediated Gene Delivery by Polycations," *Biochemistry* 35(3):1027-1036.

Gourdie, T.A. (1991). "Synthesis and Evaluation of DNA-Targeted Spatially Separated Bis(aniline mustards) as Potential Alkylating Agents with Enhanced DNA Cross-Linking Capability," *J. Med. Chem.* 34(1):240-248.

Greenwalt, T.J. et al. (1990). "Studies in Red Blood Cell Preservation: 3. A Phosphate-Ammonium-Adenine Addictive Solution," *Vox Sang* 58:94-99.

Guenther, T.M. et al. (1992). "Direct Measurement of Melphalan Conjugation with Glutathione: Studies with Human Melanoma Cells and Mammalian Liver," *J. Pharmacol. Exp. Ther.* 260(3):1331-1336.

Guillemain, B. et al. (2003). "Helinx® Technology Inactivates Human T-Cell Leukemia Virus (HTLV-I/II) in Human Red Blood Cells," Abstract *presented at the 56th Annual Meeting of the American Association of Blood Banks (AABB)*, San Diego, CA, Nov. 1-5, 2003, two pages.

Hageman, G.J. et al. (1997). "Reducing Effects of Garlic Constituents on DNA Adduct Formation in Human Lymphocytes in Vitro," *Nutrition and Cancer* 27(2):177-185.

Hanson, C.V. et al. (Sep. 1990). "Application of a Rapid Microplaque Assay for Determination of Human Immunodeficiency Virus Neutralizing Antibody Titers," *J. Clin. Microbio.* 28(9):2030-2034.

Högman, C.F. et al. (1993). "Half-Strength Citrate CPD Combined with a New Additive Solution for Improved Storage of Red Blood Cells Suitable for Clinical Use," *Vox Sang* 65:271-278.

Högman, C.F. et al. (1991). "Storage of Saline-Adenine-Glucose-Mannitol-Suspended Red Cells in a new Plastic Container: Polyvinylchloride Plasticized with Butyryl-n-Trihexyl-Citrate," *Transfusion* 31(1):26-29.

Hsiung, G.D. et al. (1957). "Morphologic Characteristics of Plaques Produced on Monkey Kidney Monolayer Cultures by Enteric Viruses (Poliomyelitis, Coxsackie, and Echo Groups)," *The Journal of Immunology* 78:128-136.

International Search Report mailed on May 11, 2010, for PCT Application No. PCT/US2009/040032, filed on Apr. 9, 2009, three pages.

International Search Report mailed Apr. 5, 2006, for PCT Application No. PCT/US2005/039392 filed Oct. 31, 2005, five pages.

Kawabata, T.T. et al. (1990). "Mechanisms of in vitro Immunosuppression by Hepatocyte-Generated Cyclophosphamide Metabolites and 4-Hydroperoxycyclophosphamide," *Biochem. Pharmacol.* 40(5):927-935.

Koch, T. et al. (1996). "Effects of N-Acetylcysteine on Bacterial Clearance," *European J. of Clinic. Invest.* 26:884-892.

Lasic D.D. (1997). "Liposomes," Chapter 6 in *Liposomes in Gene Delivery*, CRC Press: Boca Ration, FL, pp. 67-112.

Lew, V.L. et al. (May 15, 2003, e-pub. Jan. 16, 2003). Excess Hemoglobin Disgestion and the Osmotic Stability of *Plasmodium Falciparum-infected* Red Blood Cells, *Blood* 101(10):4189-4194.

Logrippo, G.A. et al. (1958). "Chemical and Combined Methods for Plasma Sterilization" in *Proceedings of the Sixth Congress of the International Society of Blood Transfusion*, S. Karger: New York, NY, pp. 225-230.

Malmberg, P.O. et al. (1979). "Effect of Increased Blood-Oxygen Affinity on Oxygen Transport in Hemorrhagic Shock," *J. Appl. Physiol. Respirat Environ Exercise Physiol.* 47:889-895.

Mangels, J.I. et al. (1978). "Quantitative Evaluation of Three Commercial Blood Culture Media for Growth of Anaerobic Organisms," *J. of Clin Microbiology* 7(1):59-62.

Marcus, P.I. et al. (1994). "Cell Killing by Viruses: 1. Comparison of Cell-Killing, Plaque-Forming, and Defective-Interfering Particles of Vesicular Stomatitis Virus," *Virology* 57:321-338.

Mattes, W.B. (1992). "Use of [8-$^3$H]Guanine-Labeled Deoxyribonucleic Acid to Study Alkylating Agent Reaction Kinetics and Stability," *Anal. Biochem.* 206(1):161-167.

Mulder, G.J. et al. (1997). "Modulation of Glutathione Conjugation in Vivo: How to Decrease Glutathione Conjugation in Vivo or in Intact Cellular Systems in Vitro," *Chemico-Biological Interactions* 105:17-34.

Mullan, R.J. et al. (Jun. 23, 1989) "Guidelines for Prevention of Transmission of Human Immunodeficiency Virus and Hepatitis B Virus to Health-Care and Public Safety Workers," *Morbidity and Mortality Weekly Report* 38(5-6):1, 3-37.

Ness, P. M. et al. (Oct. 2001). "An Animal Model for Delayed Hemolytic Transfusion Reactions," *Trans. Med. Rev.* 15(4):305-317.

Petz, L.D. et al., eds. (1996). "K Irradiation of Cellular Blood Components for Prevention of TA-GVHD," in "Graft-Versus-Host-Disease" in *Clinical Practice of Transfusion Medicine*, Third Edition, Churchill Livingstone, pp. 939-940.

Popovic, M. et al. (May 4, 1984). "Detection, Isolation, and Continuous Production of Cytophatic Retroviruses (HTLV-III) from Patients with AIDS and Pre-AIDS," *Science* 224:497-500.

Press Release (Sep. 4, 2003). "Baxter and Cerus Halt Red Blood Cell Clinical Trials for Investigational Pathogen Inactivation System," Cerus Corporation, 2 pages.

Press Release (Nov. 17, 2003). "Vitex Halts Entrollment in Phase III Chronic Trial of the INACTINE™ Pathogen Reduction System," V.I. Technologies, Inc, 2 pages.

Roth, Jr., E.F. et al. (1987). "Survival Rates and Properties of Sickel Cell Anemia Red Cells Treated with Nitrogen Mustard," *Pathophysiological Aspects of Sickle Cell Vaso-Occlusion* pp. 245-261.

Rywkin, S. et al. (1992). "Importance of Type I and Type II Mechanisms in the Photodynamic Inactivation of Viruses in Blood with Aluminum Phthalocyanine Derivatives," *Photochemistry and Photobiology* 56(4):463-469.

Schott, M.A. et al. (2005). "Modification of the S-303 RBC Pathogen Inactivation Process Results in Normal S-303 RBC Viability in Rabbits Hyper-immunized to S-303," *presented at the: International*

(56) References Cited

OTHER PUBLICATIONS

*Society of Blood Transfusion (ISBT)*, XV Regional Congress, Europe, Athens, Greece, Jul. 2-6, 2005, two pages.

Simon, E.R. (Jul.-Aug. 1977). "Adenine in Blood Banking," *Transfusion* 17(4):317-325.

Song, P.-S. et al. (Jun. 1979). "Review Article: Photochemistry and Photobiology of Psoralens," *Photochem. and Photobio.* 29:1177-1197.

Stassinpoulos, A. et al. (2005) "A Modified S-303 pathogen Inactivation Process Eliminates Immunoreactivity of S-303 RBC Detected in Pivotal Clinical Trials" Abstract No. 0774 *presented at:European Hematology Association (EHA)*, 10th Congress, Concord, United States of America, Jun. 5, 2005, located at <http://www.parthen-impact.com/cgi-bin/pco/6_05EHA/public/index.cgi?unit=_search_r . . . >,last visited on Jan. 8, 2007, two pages.

Stassinpoulos, A. et al., (2005). "Retention of RBC Viability After pathogen Inactivation with S-303: Use of a hyperimmune (Anti-S-303) rabbit transfusion model," Abstract No. 0614 *presented at:European Hematology Assocation (EHA)*,10[th] Congress, Stockholm , Sweden, Jun. 2-5, 2005, located at <http://www.parthen-impact.com/cgi-bin/pco/6_05EHA/public/index.cgi?unit=pub_search_r . . . >, last visited on Jan. 8, 2007, two pages.

Suzuki, T. et al. (Sep. 1987)."Biotinylated Erythrocytes: In Vivo Survival and in Vitro Recovery," *Blood* 70(3):791-795.

Szinicz, L. et al. (1981). "Effect of Various Compounds on the Reaction of tris-(2-Chloroethyl)amine with Ribonucleic Acid In Vitro and on its Toxicity in Mice," *Arzneimittel-Forshung* 31:1713-1717.

Tew, K.D. (Aug. 15, 1994). "Glutathione-Associated Enzymes in Anticancer Drug Resistance," *Cancer Research* 54:4313-4320.

Wagner, Jr., S.J. et al. (1993). "Red Cell Alterations Associated with Virucidal Methylene Blue Phototreatment," *Transfusion* 33(1):30-36.

Watson, E. et al. (Dec. 1985). "Kinetics of Phosphoramide Mustard Hydrolysis in Aqueous Solution," *J. Pharm. Sci.* 74(12):1283-1292.

Wedner, H.J. et al. (1985). "Inhibition of Lectin-Induced Lymphocyte Activation by 2-cyclohexene-1-One: Analysis of DNA Synthesis in Individual Cells by BUdR Quenching of Hoechst 33258," (1985). *Int. J. Immunopharmac.* 7(1):25-30.

Weinberg, E. et al. (Feb. 1984). "Effectiveness of the Antimicrobial Removal Device, BACTEC 16B Medium, and Thiol Broth in Neutralizing Antibacterial Activities of Imipenem, Norfloxacin, and Related Agents," *J. of Clin. Microbiology* 19(2):207-209.

Woodson, R.D. (1979). "Physiological Significance of Oxygen Dissociation Curve Shifts," *Critical Care Medicine* 7(9):368-373.

Written Opinion mailed on May 11, 2010, for PCT Application No. PCT/US2009/040032, filed on Apr. 9, 2009, eight pages.

Written Opinion mailed on Apr. 5, 2006, for PCT Application No. PCT/US2005/039392 filed Oct. 31, 2005, five pages.

Yuan, Z.-M. et al. (1991). "Glutathione Conjugation with Phosphoramide Mustard and Cyclophosphamide. A Mechanistic Study Using Tandem Mass Spectometry," *Drug Metab. Dispos.* 19(3):625-629.

Dirven, H.A.A.M. et al. (1995). "Glutathione Conjugation of the Cytostatic Drug Ifosfamide and the Role of Human Glutathione S-Transferases," *Chem. Res. Toxicol.* 8(7):979-986.

Dirven, H.A.A.M. et al. (1994). "The Interaction of Glutathione with 4-Hydroxycyclophosphamide and Phosphoramide Mustard, Studied by $^{31}$P Nuclear Magnetic Resonance Spectroscopy," *Chem. Bio. Interact.* 93:185-196.

Schott, M.A. et al. (2005). "Retention of RBC Viability After Pathogen Inactivation with S-303: Use of a Hyperimmune (Anti-S-303) Rabbit Transfusion Model," *presented at the 10th Congress of the European Hematology Association (EHA)*, Stockholm, Sweden, Jun. 2-5, 2005, two pages.

Stassinopoulos, A. et al. (2004). "Elimination of Immunoreactivity of Red Cells Treated with a Modified S-303 Pathogen Inactivation Process," Abstract *presented at the 46th Annual Meeting of the American Society of Hematology (ASH)*, San Diego, CA, Dec. 4-7, 2004, two pages.

\* cited by examiner

QUENCHING METHODS FOR RED BLOOD CELL PATHOGEN INACTIVATION

CROSS REFERENCE TO RELATED APPLICATIONS

This application is a National Phase application under 35 U.S.C. §371 of International Application No. PCT/US2009/040032 filed Apr. 9, 2009, which claims priority benefit of U.S. Provisional Application No. 61/043,666, entitled "Quenching Methods For Red Blood Cell Pathogen Inactivation" filed Apr. 9, 2008, and U.S. Provisional Application No. 61/087,034, entitled "Quenching Methods For Red Blood Cell Pathogen Inactivation" filed Aug. 7, 2008. The disclosures of which are incorporated herein by reference in their entirety.

STATEMENT OF RIGHTS TO INVENTIONS MADE UNDER FEDERALLY SPONSORED RESEARCH

This invention was made with Government support of Grant No. W81XWH-08-1-0480 awarded by the US Army Medical Research and Material Command. The Government has certain rights in this invention.

FIELD OF THE INVENTION

The field of this invention relates to improved methods of quenching reactive electrophilic compounds used in treating blood products to inactivate possible pathogen contaminants. In particular, nucleophilic compounds, such as thiols, are used at an elevated concentration to quench the reactive electrophilic compounds in red blood cell compositions, then decreased in concentration to reduce red blood cell (RBC) dehydration.

BACKGROUND OF THE INVENTION

The transmission of disease by blood products and other biological materials remains a serious health problem. While significant advances in blood donor screening and blood testing have occurred, viruses such as hepatitis B (HBV), hepatitis C (HCV), and human immunodeficiency virus (HIV) may escape detection in blood products during testing due to low levels of virus or viral antibodies. In addition to the viral hazard, there are currently no adequate licensed tests to screen for the presence of non-viral microbes, such as bacteria or protozoans, in blood intended for use in transfusions. The risk also exists that a hitherto unknown pathogen may become prevalent in the blood supply and present a threat of disease transmission, as in fact occurred before the recognition of the risk of HIV transmission via blood transfusions.

Chemical agents have been introduced into blood or blood plasma to inactivate pathogens prior to clinical use of the blood product. Typically, for blood products having little or no red blood cell content, such as platelets and plasma, photochemically activated compounds such as psoralens are used. For red blood cell-containing blood products, compounds have been developed for pathogen inactivation, which do not require photoactivation. These compounds typically have electrophilic groups that react with pathogens, more specifically with pathogen nucleic acid. For example, U.S. Pat. No. 5,055,485 describes the inactivation of viruses in cell and protein-containing compositions using aryl diol epoxides. Other compounds that generate electrophiles in situ may be used. LoGrippo et al. evaluated the use of nitrogen mustard, $CH_3$—$N(CH_2CH_2Cl)_2$, for viral inactivation. LoGrippo et al., Proceedings of the Sixth Congress of the International Society of Blood Transfusion, Bibliotheca Haematologica (Hollander, ed.), 1958, pp. 225-230. More significantly, U.S. Pat. Nos. 5,691,132; 6,177,441; 6,410,219; 6,143,490; and 6,093,725, the disclosures of which are hereby incorporated by reference, describe the use of compounds that have a nucleic acid targeting component as well as an electrophilic component that reacts with the nucleic acid in order to inactivate the pathogen. U.S. Pat. Nos. 6,093,725 and 6,514,987, the disclosures of which are hereby incorporated by reference, describe similar compounds, wherein the nucleic acid targeting component of the compound is linked to the reactive electrophilic component via a hydrolysable linker. U.S. Pat. Nos. 6,136,586 and 6,617,157, the disclosures of which are hereby incorporated by reference, describe using ethyleneimine oligomers and related compounds for pathogen inactivation. These ethyleneimine-derived compounds typically have an aziridine group, which provides the reactive electrophilic component, and a polyamine component, which provides nucleic acid targeting of the compound. The general class of nucleic acid targeted compounds having an electrophilic or similar group reactive with the nucleic acid are used to inactivate pathogens in blood, blood products, and a variety of samples of biological origin.

There is some concern that, while these compounds are designed to specifically target nucleic acids, they may react with other components of the blood, such as proteins or cellular membranes. These side-reactions are unfavorable and may cause adverse effects, such as modifications of proteins and cell membranes that may be recognized by the immune system. When such treated blood products are used repeatedly, they may result in an immune response of the recipient to the treated blood product. U.S. Pat. Nos. 6,270,952; 6,709,810; and 7,293,985, the disclosures of which are hereby incorporated by reference, describe methods of quenching such pathogen-inactivating compounds in order to reduce the level of any such adverse side-reactions. U.S. Patent Publication No. 2006/0115466, the disclosure of which is hereby incorporated by reference, describes improvements to these quenching conditions which address an immune response developed against the pathogen-inactivating compound. However, despite the improvement in quenching effectiveness, in some cases the treated red blood cells have been found to have decreased lifespan attributed to increased cell dehydration as measured by decreased osmotic fragility and decreased spun hematocrit.

Thus, there is a need for methods to reduce unwanted electrophilic side-reactions of pathogen-inactivating compounds while preserving the ability of the pathogen-inactivating compound to inactivate harmful pathogens without adversely affecting the vitality and lifespan of the treated blood product. Specifically, there is a need for improved methods of quenching pathogen-inactivating compounds in red blood cells.

BRIEF SUMMARY OF THE INVENTION

The present invention provides a variety of methods for treating red blood cell compositions with a pathogen-inactivating compound and a quencher under conditions which provide suitable pathogen inactivation and reduction of unwanted side reactions (such as modification of the red blood cells), while reducing or minimizing adverse effects such as increased dehydration of the cells. In some embodiments, the quencher is glutathione which is neutralized with an appropriate amount of base. In some embodiments, the method involves reducing the concentration of glutathione following pathogen inactivation.

In one aspect, the present invention provides a method of treating a red blood cell composition comprising: a) providing i) an effective amount of a pathogen-inactivating compound to inactivate a pathogen, if present, wherein the pathogen-inactivating compound comprises a functional group which is, or which forms, a reactive electrophilic group, ii) an effective amount of a quencher comprising a thiol group, wherein the thiol is capable of reacting with the reactive electrophilic group of the pathogen-inactivating compound, and iii) a composition comprising red blood cells; b) mixing the pathogen-inactivating compound and quencher with the composition comprising red blood cells; and c) sufficiently decreasing the concentration of the quencher in the mixture to an amount which reduces the level of red blood cell dehydration resulting from storage of the mixture, relative to the level of red blood cell dehydration resulting from storage of the mixture at the original concentration of quencher. In some of these embodiments, decreasing the concentration of the quencher comprises removal of the solution used during inactivation and addition of a final additive solution (e.g., any solution described in herein, such as SAG-M, AS-5 or any solution of Tables 2, 3, or 4).

In some embodiments, step (a) further comprises providing a suitable base, step (b) further comprises mixing the base with the composition comprising red blood cells, and the base is of sufficient amount to reduce the level of an unwanted reaction of the pathogen-inactivating compound with red blood cells in the mixture, relative to the mixture without the base. In some embodiments, the unwanted reaction of the pathogen-inactivating compound with red blood cells is modification of the surface of the red blood cells by the pathogen-inactivating compound. In some embodiments, step (a) further comprises providing a suitable base, step (b) further comprises mixing the base with the composition comprising red blood cells, and the base is of sufficient amount to reduce the level of anti-pathogen inactivating compound antibody binding to the treated red blood cell composition in the resulting mixture by at least about 5% (or at least about 10%, at least about 25%, at least about 50%, at least about 75%, or at least about 90%) relative to the mixture without the base. In some embodiments, the base and the quencher are mixed with the red blood cell composition prior to, at the same time, or no more than about 30 minutes after mixing the pathogen-inactivating compound with the red blood cell composition. In some embodiments, the base and the quencher are mixed together prior to mixing either the base or the quencher with the red blood cell composition. In some embodiments, the base is NaOH. In some embodiments, the base is a basic buffer. In some embodiments, the base comprises about 0.5 to 1.5 equivalents of base, where an equivalent means a molar amount that is equivalent to the molar amount of quencher in the mixture. In some embodiments, the base comprises about 0.75 to 1.25 equivalents of base. In some embodiments, the base comprises about 1 equivalent of base. In some embodiments, the resulting mixture of step (b) has a pH at 37° C. of about 6.0 to 7.5. In some embodiments, the pH is about 6.5 to 7.1. In some embodiments, the pH is about 6.8 or 6.9.

In some embodiments, the quencher comprises cysteine or a derivative of cysteine. In some embodiments, the quencher is glutathione or a pharmaceutically acceptable salt thereof. In some embodiments, the concentration of the quencher in the resulting mixture of step (b) is greater than 2 mM. In some embodiments, the quencher concentration is about 5 mM to about 30 mM. In some embodiments, the quencher concentration is about 15 mM to about 25 mM. In some embodiments, the quencher concentration is about 20 mM.

In some embodiments, decreasing the concentration of quencher in step (c) comprises centrifugation of the mixture followed by removal of the supernatant. In some embodiments, step (c) comprises size-exclusion separation. In some embodiments, the quencher in the resulting mixture of step (c) is at a concentration of less than about 10 mM. In some embodiments, the quencher concentration is less than about 8 mM. In some embodiments, the quencher concentration is less than about 6 mM (or less than about 4 mM, or less than about 2 mM). In some embodiments, storage of the mixture is storage of the mixture for greater than 10 days at 4° C. In some embodiments, storage of the mixture is storage of the mixture for greater than 42 days (or 28 days) at 4° C. In some embodiments, the method comprises the addition of an additive solution (e.g., any additive solution described in Table 2, and/or an additive solution comprising sodium chloride, adenine, glucose, phosphate, guanosine, citrate and/or mannitol). In some embodiments, the mixture is stored in an additive solution (e.g., any additive solution described in Table 2, and/or an additive solution comprising sodium chloride, adenine, glucose, phosphate, guanosine, citrate and/or mannitol). In some embodiments, the method further comprises replacement of a treatment solution (e.g., any solution described in Tables 2, 3, or 4 and/or a solution comprising sodium chloride, adenine, glucose, phosphate, guanosine, citrate, and/or mannitol) with an additive solution (e.g., any additive solution described in Table 2, and/or an additive solution comprising sodium chloride, adenine, glucose, phosphate, guanosine, citrate and/or mannitol). In some embodiments, the chloride concentration of the composition prior to decreasing the concentration of the quencher is less than about 100 mM (or about 75 mM). In some embodiments, the chloride concentration of the composition following decreasing the concentration of the quencher and/or adding the additive solution is greater than about 100 mM (or about 125 mM).

In some embodiments of each of the aforementioned methods, as well as other methods described herein, the functional group is a mustard, a mustard intermediate, or a mustard equivalent. In some embodiments, the functional group is, or is capable of forming, an aziridinium ion. In some embodiments, the reactive electrophilic group is capable of reacting with nucleic acids. In some embodiments, the pathogen-inactivating compound further comprises a nucleic acid binding ligand. In some embodiments, the nucleic acid binding ligand is an intercalator. In some embodiments, the intercalator is an acridine. In some embodiments, the pathogen-inactivating compound comprises a frangible linker linking the functional group and the nucleic acid-binding ligand. In some embodiments, the pathogen-inactivating compound is β-alanine, N-(acridin-9-yl), 2-[bis(2-chloroethy)amino]ethyl ester. In some embodiments, the concentration of the pathogen inactivation compound in the resulting mixture of step (b) is about 0.1 µM to about 5 mM. In some embodiments, the concentration is sufficient to inactivate at least 1 log of a pathogen in the red blood cell composition, if present. In some embodiments, the concentration is sufficient to inactivate at least 3 logs of a pathogen. In some embodiments, the time between step (b) and step (c) is about 1 to 48 hours. In some embodiments, the time is about 10 to 30 hours. In some embodiments, the time is about 15 to 25 hours. In some embodiments, the treatment inactivates at least 1 log of a pathogen contaminant in the red blood cell composition, if present. In some embodiments, the treatment inactivates at least 3 logs. In some embodiments, the method further comprises the step of decreasing the concentration of the pathogen-inactivating compound in the mixture. In some embodiments, the steps of decreasing the concentration of the quencher in the mixture and decreasing the concentration of the pathogen-inactivating compound in the mixture occur at the same time.

In some embodiments of each of the aforementioned methods, as well as other methods described herein, at 20 hours following step (b), the red blood cells (RBCs) of the resulting mixture have an anti-pathogen inactivating compound antibody binding capacity (ABC) of less than 65% compared to the ABC value of red blood cells from the same method under the same conditions, but without the use of base. In some embodiments, the RBCs have an average ABC of less than about 50,000. In some embodiments, the RBCs have an average ABC of less than about 40,000. In some embodiments, the RBCs have an average ABC of between about 25,000 and 70,000. In some embodiments, the RBCs have an average ABC of between about 35,000 and 45,000. In some embodiments, the RBCs of the resulting mixture have less then 1% hemolysis following step (c). In some embodiments, the RBCs have less then 1% hemolysis at a time of 42 days (or 28 days) at 4° C. following step (c). In some embodiments, the RBCs of the resulting mixture have a Packed Cell Volume (PCV) of greater than 50% following step (c). In some embodiments, the RBCs have a PCV of greater than 50% at a time of 42 days (or 28 days) at 4° C. following step (c). In some embodiments, the RBCs of the resulting mixture have a Median Corpuscular Fragility value greater than 140 (or 150) after 42 days (or 28 days) at 4° C. following step (c). In some embodiments, the amount of pathogen inactivation compound is not reduced and/or the pathogen inactivation compound is not contacted with a compound adsorption device (CAD).

In an additional aspect, the invention provides a method of reducing dehydration of red blood cells, comprising: a) providing a red blood cell composition comprising a mixture of i) a quencher, where the quencher is capable of reacting with a pathogen-inactivating compound, and ii) red blood cells; and b) sufficiently decreasing the concentration of the quencher (and optionally the concentration of the pathogen-inactivating compound and/or byproducts thereof) in the mixture to an amount which reduces the level of red blood cell dehydration resulting from storage of the mixture relative to the level of red blood cell dehydration resulting from storage of the mixture at the original concentration of quencher. In some embodiments, the quencher comprises cysteine or a derivative of cysteine. In some embodiments, the quencher is glutathione or a pharmaceutically acceptable salt thereof. In some embodiments, the quencher in the resulting mixture of step (b) is at a concentration of less than about 10 mM. In some embodiments, the quencher concentration is less than about 8 mM. In some embodiments, the quencher concentration is less than about 6 mM, or less than about 2 mM. In some embodiments, the red blood cells (RBCs) of the resulting mixture have less then 1% hemolysis following step (b). In some embodiments, the RBCs have less then 1% hemolysis at a time of 42 days (or 28 days) at 4° C. following step (b). In some embodiments, the RBCs of the resulting mixture have a Packed Cell Volume (PCV) of greater than 50% following step (b). In some embodiments, the RBCs of the resulting mixture have a PCV of greater than 50% at a time of 42 days (or 28 days) at 4° C. following step (b). In some embodiments, the RBCs of the resulting mixture have a Median Corpuscular Fragility value greater than 140 (or 150) after 42 days (or 28 days) at 4° C. following step (b). In some embodiments, storage of the mixture is storage of the mixture for greater than 10 days at 4° C. In some embodiments, storage of the mixture is storage of the mixture for greater than 42 days (or 28 days) at 4° C. In some embodiments, the amount of pathogen inactivation compound is not reduced and/or the pathogen inactivation compound is not contacted with a compound adsorption device (CAD).

Red blood cell (RBC) compositions produced by each of the aforementioned methods are provided. RBC compositions preparable by each of the aforementioned methods are also provided.

In a further aspect, the invention provides a composition comprising a) red blood cells, wherein the red blood cells have covalently reacted with an electrophilic group of a pathogen-inactivating compound; and b) a quencher comprising a thiol group that is capable of reacting with the pathogen-inactivating compound; wherein the composition is suitable for infusion into humans after storage up to 42 days (or 28 days) at 4° C. In some embodiments, at least 1 log of a pathogen is inactivated, if present. In some embodiments, at least 3 logs are inactivated. In some embodiments, the electrophilic group is a mustard, a mustard intermediate, or a mustard equivalent. In some embodiments, the electrophilic group is, or is capable of forming, an aziridinium ion. In some embodiments, the electrophilic group is capable of reacting with nucleic acids. In some embodiments, the electrophilic group is covalently reacted with the cell surface of the red blood cells. In some embodiments, the pathogen-inactivating compound further comprises a nucleic acid binding ligand. In some embodiments, the nucleic acid binding ligand is an intercalator. In some embodiments, the intercalator is an acridine. In some embodiments, the pathogen-inactivating compound comprises a frangible linker linking the electrophilic group and the nucleic acid binding ligand. In some embodiments, the pathogen-inactivating compound is β-alanine, N-(acridin-9-yl), 2-[bis(2-chloroethy)amino]ethyl ester. In some embodiments, the quencher comprises cysteine or a derivative of cysteine. In some embodiments, the quencher is glutathione or a pharmaceutically acceptable salt thereof. In some embodiments, the quencher is at a concentration that is sufficiently low to avoid or minimize red blood cell dehydration during storage. In some embodiments, the quencher concentration is less than about 10 mM. In some embodiments, the quencher concentration is less than about 8 mM. In some embodiments, the quencher concentration is less than about 6 mM, or less than about 2 mM. In some embodiments, the red blood cells (RBCs) have a Packed Cell Volume (PCV) of greater than 55%. In some embodiments, the RBCs have a PCV of greater than 60%. In some embodiments, the RBCs have an average antibody binding capacity (ABC) of less than about 50,000. In some embodiments, RBCs have an average ABC of less than about 40,000. In some embodiments, the RBCs have an average ABC of between about 25,000 and 60,000. In some embodiments, the RBCs have an average ABC of between about 25,000 and 70,000. In some embodiments, the RBCs have an average ABC of between about 35,000 and 45,000. In some embodiments, the composition further comprises an additive solution (e.g., any additive solution described in Table 2, and/or an additive solution comprising sodium chloride, adenine, glucose, phosphate, guanosine, citrate and/or mannitol). In some embodiments, the chloride concentration of the additive solution and/or of the composition is greater than about 100 mM (or about 125 mM).

In an additional aspect, the invention provides methods of infusing red blood cells into an individual, comprising: a) providing any one of the aforementioned red blood cell compositions or a red blood cell composition produced by any one of the methods described herein and, b) infusing the red blood cell composition into the individual.

In one aspect, the invention provides a method of treating a red blood cell composition comprising: (a) mixing (i) a pathogen-inactivating compound comprising a functional group which is, or which forms, a reactive electrophilic group (e.g., an effective amount of a pathogen-inactivating compound to inactivate a pathogen, if present); (ii) a quencher (e.g., an effective amount of a quencher) comprising a thiol group, wherein the thiol is capable of reacting with the reactive electrophilic group of the pathogen-inactivating compound; and (iii) a composition comprising red blood cells; and (b) sufficiently decreasing the concentration of the quencher in the mixture to an amount which reduces the level of red blood cell dehydration resulting from storage of the mixture relative to the level of red blood cell dehydration resulting from storage of the mixture at the original concentration of quencher. In some of these embodiments, decreasing the concentration of the quencher comprises removal of the solution used during inactivation and addition of a final additive solution (e.g., any solution described in herein, such as SAG-M, AS-5 or any solution of Tables 2, 3, or 4). The method may comprise any one or more of the embodiments listed above and/or herein.

In some embodiments, the method further comprises mixing a suitable base with the composition comprising red blood cells, and the base is of sufficient amount to reduce the level of an unwanted reaction of the pathogen-inactivating compound with red blood cells in the mixture, relative to the mixture without the base. In some embodiments, the unwanted reaction of the pathogen-inactivating compound with red blood cells is modification of the surface of the red blood cells by the pathogen-inactivating compound. In some embodiments, method further comprises mixing a suitable base with the composition comprising red blood cells, and the base is of sufficient amount to reduce the level of anti-pathogen inactivating compound antibody binding to the treated red blood cell composition in the resulting mixture by at least about 5% (or at least about 10%, at least about 25%, at least about 50%, at least about 75%, or at least about 90%) relative to the mixture without the base.

In one aspect, the invention provides a method of reducing dehydration in a red blood cell composition wherein the composition is a mixture comprising a quencher capable of reacting with a pathogen-inactivating compound, and red blood cells; the method comprising, sufficiently decreasing the concentration of the quencher in the mixture to an amount which reduces the level of red blood cell dehydration resulting from storage of the mixture relative to the level of red blood cell dehydration resulting from storage of the mixture at the original concentration of quencher.

In another aspect, the invention provides a method of red blood cells infusion, comprising infusing a red blood cell composition described herein into an individual.

DETAILED DESCRIPTION OF THE INVENTION

Figure 1:
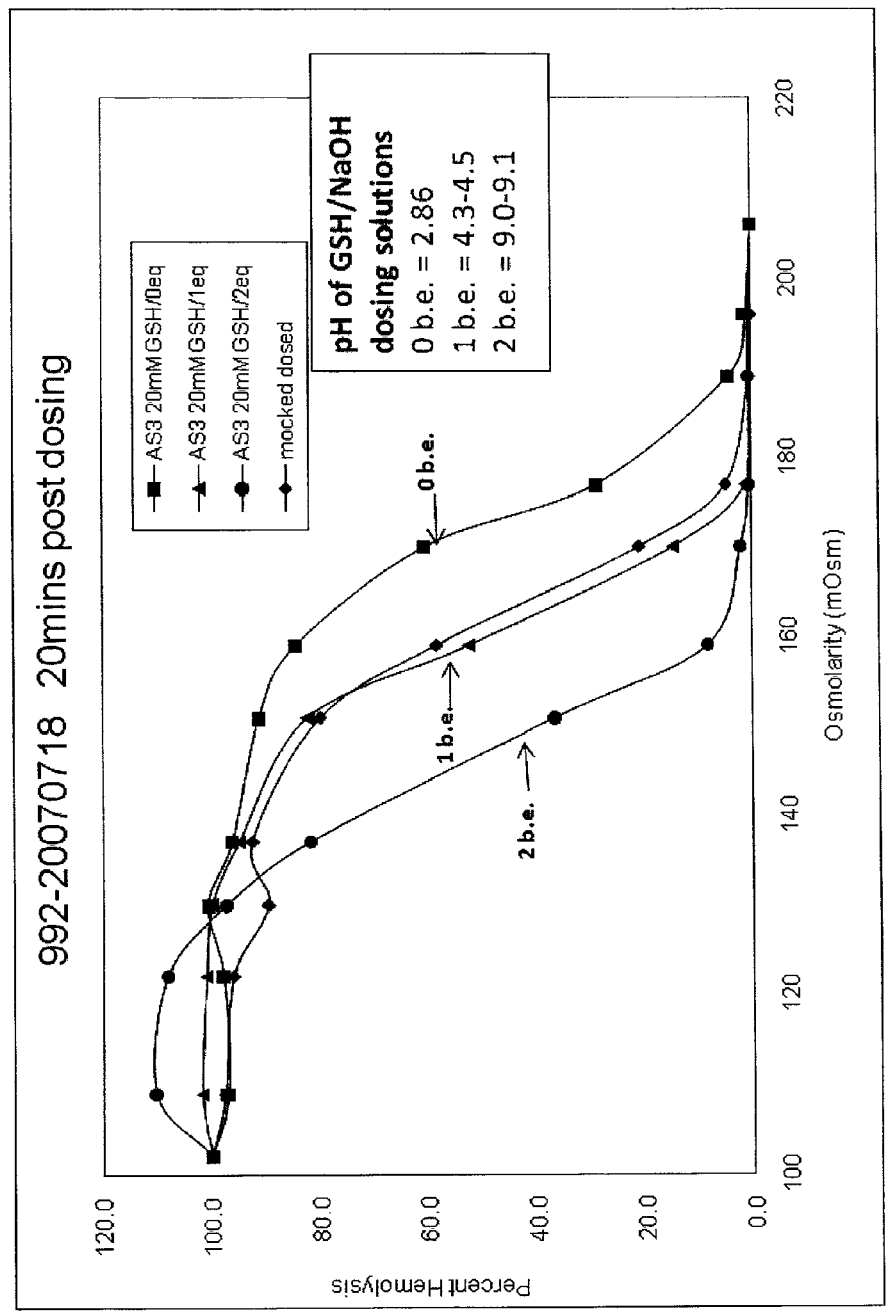
FIG. 1 shows the osmotic fragility of red blood cells at various levels of base after initial quencher dosing as described in Example 6.

The present invention provides methods for treating red blood cell compositions to inactivate pathogens which may be present, while reducing or minimizing unwanted side reactions (such as modification of the red blood cells leading to an undesired immune response) and while reducing or minimizing adverse effects on cell vitality (e.g., decreased osmotic fragility and/or increased dehydration) and/or lifespan during and after treatment. We have found that the proper control of pH in conjunction with suitable amounts of quencher during the pathogen inactivation process can reduce initial dehydration of red blood cells treated with a pathogen-inactivating compound. The process can then be followed by reduction of the initial quencher concentration to provide healthy pathogen-inactivated red blood cells capable of cell storage, without significant changes in osmotic fragility. These methods are particularly suitable for preparation of red blood cell compositions in which pathogens have been inactivated for clinical use, especially when the compositions are to be stored for a period of time prior to clinical use.

Accordingly, the present invention in one aspect provides a method of treating a red blood cell composition comprising a pathogen-inactivating compound and a quencher, by (1) mixing the pathogen-inactivating compound and quencher with the composition comprising red blood cells; and (2) sufficiently decreasing the concentration of the quencher to reduce the level of red blood cell dehydration resulting from storage of the mixture relative to the level of red blood cell dehydration resulting from storage of the mixture at the original concentration.

In other aspects, the present invention provides methods of reducing dehydration and/or increasing osmotic fragility in red blood cells, as well as methods of infusing red blood cells into humans. Also provided are treated red blood cell compositions.

Red Blood Cells

Red blood cell compositions of the invention include, but are not limited to, any blood product comprising red blood cells (e.g., human blood), wherein the blood product provides, or is processed to provide, red blood cells suitable for use in humans, mammals, and/or vertebrates, such as for infusion. Red blood cell compositions include, for example, whole blood and red blood cell concentrates, such as packed red blood cells (pRBCs; e.g., red blood cells with increased hematocrit and/or not containing additive solution). The red blood cell compositions may be described by their hematocrit or packed cell volume (PCV), a measure of the concentration of red blood cells in the composition. Red blood cell compositions may have a hematocrit in the range of about 1 to 100%, more likely about 10 to 90%, also about 35 to 80%, or about 40 to 70%. Such red blood cell compositions may include chemicals, such as pathogen-inactivating compounds and quenchers. They may also include buffers and other solutions, such as red blood cell additive solutions (e.g., any solution described in herein, such as SAG-M, AS-5 or any solution of Tables 2, 3, or 4), including salts or buffered solutions. In some embodiments, the red blood cell compositions described herein are packed red blood cells having a hematocrit in the range of about 70 to 90%, or about 75 to 85%, or about 80%, prior to use in the methods of treating described herein. In some embodiments, the red blood cell compositions are non-packed red blood cells having a hematocrit in the range about 50 to 70%, or about 55 to 65%, or about 60%, prior to and/or during use in the methods of treating described herein. In some embodiments, the red blood cell compositions are diluted with a diluent solution and have a hematocrit in the range about 30 to 50%, or about 35 to 45%, or about 40%, prior to and/or during use in the methods of treating described herein. In some embodiments, the red blood cell compositions described herein have been leukoreduced prior to use in the methods of treating described herein. In some embodiments, the red blood cell compositions have not been leukoreduced. Any red blood cell composition that will come into contact with, or be introduced into, a living human, mammal, or vertebrate, where such contact carries a risk of transmitting disease due to contaminating pathogens may be treated as disclosed herein.

Blood Pathogens

A pathogen contaminant, if present, to be inactivated in the methods of the invention includes any nucleic acid-containing agent capable of causing disease in a human, other mammals, or vertebrates. The pathogenic agent may be unicellular or multicellular. Examples of pathogens are bacteria, viruses, protozoa, fungi, yeasts, molds, and mycoplasmas which cause disease in humans, other mammals, or vertebrates. The genetic material of the pathogen may be DNA or RNA, and the genetic material may be present as single-stranded or double-stranded nucleic acid. Table 1 lists examples of viruses, and is not intended to limit the invention in any manner.

TABLE 1

Non-limiting examples of viruses

| Family: | Virus: |
|---|---|
| Adeno | Adenovirus 2 |
|  | Canine hepatitis |
| Arena | Pichinde |
|  | Lassa |
| Bunya | Turlock |
|  | California encephalitis |
| Herpes | Herpes simplex 1 |
|  | Herpes simplex 2 |
|  | Cytomegalovirus |
|  | Pseudorabies |
| Orothomyxo | Influenza |
| Papova | SV-40 |
| Paramyxo | Measles |
|  | Mumps |
|  | Parainfluenza 2 and 3 |
| Picorna | Poliovirus 1 and 2 |
|  | Coxsackie A-9 |
|  | Echo 11 |
| Pox | Vaccinia |
|  | Fowl Pox |
| Reo | Blue tongue |
|  | Colorado tick fever |
| Retro | HIV |
|  | Avian sarcoma |
|  | Murine sarcoma |
|  | Murine leukemia |
| Rhabdo | Vesicular stomatitis virus |
| Toga | Western equine encephalitis |
|  | Dengue 2 |
|  | Dengue 4 |
|  | St. Louis encephalitis |
| Hepadna | hepatitis B |

TABLE 1-continued

Non-limiting examples of viruses

| Family: | Virus: |
|---|---|
| Bacteriophage | Lambda |
|  | R17 |
|  | T2 |
| (Rickettsia) | *R. akari* (rickettsialpox) |

In addition to inactivating possible pathogen contaminants, the methods of the present invention may also inactivate leukocytes that may be present in the red blood cell composition. Leukoreduction methods are used to preferably remove most of the leukocytes from red blood cell compositions intended for infusion, as they may result in unwanted immune responses in the recipient. However, not all blood is leukoreduced, or leukoreduction methods may not remove all of the leukocytes. Therefore, inactivation of any residual leukocytes by the methods of the invention as described herein may further reduce the risk of such immune responses.

Pathogen-Inactivating Compounds

The inactivation of a pathogen in the red blood cell compositions is effected by contacting the pathogen in the red blood cell composition with a pathogen-inactivating compound. In any of the embodiments described herein, the pathogen-inactivating compound (e.g., S-303 described herein) may be present in an effective amount (e.g., an effective amount to inactivate a pathogen, such as an amount sufficient to inactivate, for example, at least 1 log, 2 log, or 3 log of a pathogen in the red blood cell composition, if present). Pathogen-inactivating compounds that may be used by the methods of the invention include compounds that comprise a functional group which is, or which is capable of forming and has formed, e.g. in situ, a reactive group, such as an electrophilic group. In some cases, the pathogen-inactivating compounds of the present invention do not require photoactivation to be reactive. For example, the functional group may be a mustard group, a mustard group intermediate, a mustard group equivalent, an epoxide, a formaldehyde or a formaldehyde synthon. Such functional groups are capable of forming in situ a reactive group, such as an electrophilic aziridine, aziridinium, thiirane or thiiranium ion. A mustard group may be a mono- or bis-(haloethyl)amine group or a mono (haloethyl)sulfide group. A mustard equivalent is a group that reacts by a mechanism similar to the mustards, for example by forming reactive intermediates such as aziridinium and aziridine groups or thiirane and thiiranium groups. Examples include aziridine derivatives, mono or bis-(mesylethyl)amine groups, mono-(mesylethyl)sulfide groups, mono or bis-(tosylethyl)amine groups and mono-(tosylethyl)sulfide groups. A formaldehyde synthon is any compound that breaks down to a formaldehyde, which includes a hydroxylamine such as hydroxymethylglycine. The reactive group of the pathogen-inactivating compound is capable of reacting with the nucleic acids of pathogens, for example with nucleophilic groups on the nucleic acid. The reactive group is also capable of reacting with a nucleophilic group of a quencher. Pathogen-inactivating compounds may also include a component that targets the compound to nucleic acids, such as an anchor portion. The anchor portion comprises a moiety which is capable of binding non-covalently to a nucleic acid biopolymer, such as DNA or RNA, and is also referred to as a nucleic acid binding ligand, nucleic acid binding group, or nucleic acid binding moiety. Examples of such compounds are described in U.S. Pat. Nos. 5,691,132, 6,410,219, 6,136,586, 6,617,157, and 6,709,810, each of which is incorporated by reference herein. Another class of pathogen-inactivating compounds that may be quenched by the methods of the invention comprises the above-mentioned reactive groups linked to a nucleic acid binding group via a hydrolysable linker, as described in U.S. Pat. No. 6,514,987, incorporated by reference herein. The anchor portion of the pathogen-inactivating compounds has an affinity for nucleic acids. This affinity may be due to any of several modes of binding to the nucleic acid non-covalently, including, but not limited to, intercalation, minor groove binding, major groove binding, and electrostatic binding (e.g., phosphate backbone binding). The affinity may also be due to mixed modes of binding (e.g., intercalation and minor groove binding). The binding may be sequence-specific (i.e., increased binding affinity for one or more particular nucleic acid sequences over other nucleic acid sequences) or non sequence-specific. Detailed examples of such nucleic acid binding moieties can be found in the above-mentioned patents.

In some embodiments of each of the methods, compositions, and kits described herein, the pathogen-inactivating compound may comprise a functional group which is, or which forms, a reactive electrophilic group reactive with the nucleophile of the chosen quencher. In some embodiments, the pathogen-inactivating group comprises a nucleic acid binding ligand and a functional group which is, or which forms an electrophilic group.

A specific example of a suitable pathogen-inactivating compound for use in the present invention is β-alanine, N-(acridin-9-yl), 2-[bis(2-chloroethyeamino]ethyl ester (also alternatively referred to herein as "S-303"), the structure of which is as follows, including salts thereof.

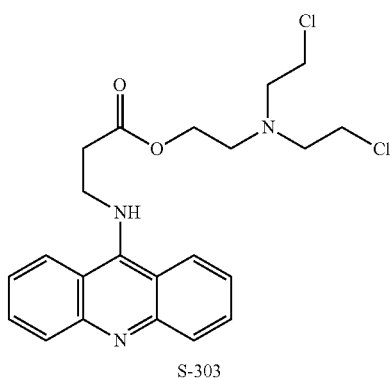 [SMILES: O=C(CCNc1c2ccccc2nc2ccccc12)OCCN(CCCl)CCCl]

S-303

In some embodiments, the concentration of the pathogen-inactivating compound, such as S-303, in the mixture with the red blood cell composition and the quencher is in the range of about 0.05 mM to 4 mM, about 0.05 mM to 2 mM, about 0.05 mM to 0.5 mM, about 0.1 mM to 0.3 mM, or about 0.2 mM. In some embodiments, the molar ratio of quencher to pathogen inactivation compound once both components have been mixed with the red blood cell composition is about 10:1 to about 400:1, also about 10:1 to about 200:1, also about 20:1 to about 200:1, also about 50:1 to about 200:1, also about 100:1.

Quenchers

Quenchers for use in methods of the present invention are intended to reduce unwanted side-reactions of the reactive electrophilic species used to inactivate pathogens (e.g., binding of the pathogen-inactivating compound to the RBC surface which may lead to an undesired immune response). In any of the embodiments described herein, the quencher (e.g., glutathione described herein) may be present in an effective amount (for example, an effective amount to reduce unwanted side reactions, such as the amounts described herein). Suitable quenchers comprise a nucleophilic group that is capable of reacting with the electrophilic group of the pathogen-inactivating compound. Non-limiting examples are described in detail in U.S. Pat. No. 6,709,810, incorporated by reference herein in its entirety. In some embodiments, the quenchers are capable of significantly reducing the unwanted side reactions in a red blood cell composition while allowing the pathogen-inactivating compound to sufficiently inactivate a pathogen that may be contaminating the red blood cell composition. In some embodiments, the improved methods of the present invention provide an effective amount of quencher in combination with an effective amount of pathogen-inactivating compound under conditions which provide optimal reduction in unwanted side reactions combined (e.g., binding of the pathogen-inactivating compound) with sufficient inactivation of pathogens, without significantly altering (e.g., without decreasing) the cell osmotic fragility and without significantly altering (e.g., without increasing) dehydration. A variety of unwanted side reactions may be reduced, such as reaction of the pathogen-inactivating compound with proteins and/or red blood cell components. In some embodiments, the quencher provides optimal reduction in the modification of the red blood cells, such as the binding of IgG to the red blood cells or binding of the pathogen-inactivating compound to the red blood cells. While the methods of the invention involve the ex vivo treatment of red blood cell compositions, some quenchers may remain in the composition upon introduction into an individual. As such, in some embodiments, the quenchers of the invention are suitable for infusion. Suitable quenchers include, but are not limited to, compounds comprising a thiol group, such as quenchers comprising the amino acid cysteine or a suitable derivative of cysteine, such as N-acetyl cysteine. Examples of such quenchers include cysteine and peptides comprising at least one cysteine, such as glutathione. In some embodiments, the suitable quenchers comprise a derivative of cysteine that can form a thiol group in situ, with or without the use of additional chemicals or added enzymes, such as S-acetyl cysteine or other suitable thiol derived prodrugs of cysteine, or peptides comprising S-acetyl cysteine or other suitable thiol derived prodrugs of cysteine. Suitable derivatives of cysteine are those which either comprise, or are capable of forming in situ, a cysteinyl thiol which is capable of reacting with the electrophilic group of the pathogen-inactivating compound.

In some embodiments, the quencher is a peptide of 2 to 10 amino acids, wherein at least one of the amino acids is cysteine, N-acetyl cysteine, S-acetyl cysteine, or other suitable derivative of cysteine. In some embodiments, the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine. In some embodiments, the quencher is a peptide of at least 3 amino acids, such as about 3-10 amino acids, also about 3-6 amino acids, wherein at least one of the amino acids is cysteine, N-acetyl cysteine, S-acetyl cysteine, or other suitable derivative of cysteine, also wherein at least 2 or at least 3 of the amino acids is cysteine, N-acetyl cysteine, S-acetyl cysteine, or other suitable derivative of cysteine.

In a preferred embodiment, the quencher is neutralized glutathione (also known as L-glutathione and γ-L-glutamyl-L-cysteinyl-glycine). Glutathione has many properties that make it particularly useful as a quencher. It is normally present in all cell types. It is not believed to be able to passively penetrate into a pathogen, such as by passing through cell membranes or lipid coats, of bacteria and lipid-enveloped viruses, or by passing through the viral capsid of non-enveloped viruses. At approximately neutral pH glutathione is charged and in the absence of active transport, does not penetrate lipid bilayers to any significant extent. This is consistent with inactivation of lipid enveloped viruses such as HIV and VSV being substantially unaffected by glutathione, including using concentrations of neutralized glutathione greater than 2 mM. The use of glutathione does have some effect on inactivation of e.g., *Yersinia enterocolitica, Staphylococcus epidermidis* and *Serratia marcescens*. However, this can be managed by using effective amounts of neutralized glutathione and pathogen-inactivating compound. As such, preferred methods of quenching are provided wherein contamination of a red blood cell composition by a viral or bacterial pathogen is inactivated by at least 2 log, preferably at least 3 log. In some embodiments, *Staphylococcus epidermidis* may be inactivated by up to at least 3 log, also about 4 log, or about 5 log and VSV can be inactivated by up to at least 4 log, also about 5 log, or about 6 log. In some embodiments, the inactivation of *Staphylococcus epidermidis* with S-303 is within about 3 log, also about 2 log, or about 1 log that of a similar composition inactivated with 2 mM acidic glutathione and 0.2 mM S-303. In some embodiments, the inactivation of VSV with S-303 is within about 2 log, or about 1 log, or essentially equal to that of a similar composition inactivated with 2 mM acidic glutathione and 0.2 mM S-303. At the appropriate conditions, as described by the present invention, glutathione is also compatible with in vitro storage of red blood cells and the resulting red blood cell composition is suitable for introduction in vivo.

In some embodiments, the quencher is glutathione in its reduced form. Glutathione disulfide, the oxidized form of glutathione, may also be used, so long as the glutathione disulfide is sufficiently reduced in solution prior to addition of the solution to the mixture comprising the red blood cell composition or sufficiently reduced after addition to the mixture comprising the red blood cell composition.

In some embodiments, the quencher is a derivative of glutathione, such as a glutathione monoalkyl ester or dialkyl ester, wherein the alkyl group is a straight or branched group having 1 to 10 carbon atoms. Specific examples of alkyl groups include, but are not limited to methyl group, ethyl group, propyl group, isopropyl group, butyl group, isobutyl group, tert-butyl group, pentyl group, isopentyl group, neo-pentyl group, tert-pentyl group, 1-methylbutyl group, hexyl group, isohexyl group, 2-methylpentyl group, 1-ethylbutyl group, heptyl group, octyl group, nonyl group, and decyl group. For instance, non-limiting examples of glutathione derivatives include glutathione methyl ester, glutathione monoethyl ester, and glutathione monoisopropyl ester. In some embodiments, glutathione oxidized diethyl ester (GSSG-(glycyl)-diethyl-ester) is used. In some embodiments, a thioester of glutathione is hydrolyzed after addition to the red blood cell compositions to form the thiol.

It is understood that in some embodiments, the quencher will be provided in the form of a free acid or base, whereas, in other embodiments, the quencher will be provided in the form of a salt. If the quencher is in the form of a salt, the salt is preferably a pharmaceutically acceptable salt. The pharmaceutically-acceptable salts of compounds (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-napthalensulfonate, nicotinate, oxalate, pamoate, pectinate, persulfate, 3-phenylpropionate, phosphate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, didbutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

For example, in some embodiments, the quencher is in the form of a pharmaceutically acceptable salt formed from glutathione. In some embodiments, the quencher is in the form of a pharmaceutically acceptable salt formed from glutathione and one or more cations such as sodium, aluminum, calcium, lithium, magnesium, zinc, or tetramethylammonium. In some embodiments, the quencher is glutathione (reduced) and is provided in the form of glutathione monosodium salt (available, e.g., from Biomedica Foscama, Italy). In some other embodiments, the glutathione (reduced) is provided in the form of glutathione hydrochloride salt. In some other embodiments, the glutathione is provided in the form of a glutathione (reduced) disodium salt. In further embodiments, a glutathione monoalkyl ester sulfate is used. In some embodiments, glutathione is provided in the form of glutathione oxidized disodium salt.

Methods of Inactivation and Quenching

The methods of the present invention involve the combination of a red blood cell composition with a pathogen-inactivating compound and a quencher under conditions wherein, upon mixing the composition with the pathogen-inactivating compound and quencher, the pH of the resulting composition is in a suitable range to provide adequate pathogen inactivation and reduction of unwanted side reactions (such as modification of the red blood cells) with limited or no effect on the vitality (e.g. osmotic fragility and dehydration) and/or lifespan of the treated blood product. Further, the present invention describes decreasing the concentration of the quencher in the red blood cell composition following a period of pathogen inactivation to aid in maintaining the vitality and lifespan of the red blood cells during storage. An additive solution, as described herein, also may be utilized for the red blood cells during storage and may be used to replace treatment solutions and/or diluent solutions used during pathogen inactivation.

The improved methods include several features that may be important for quenching. The first feature is the thiol group, or other suitable nucleophilic group. The second is the adjustment of the pH of the solution. It is possible to provide some level of quenching by suitably adjusting the pH of the solution. As such, the quenchers of the invention provide some buffering capacity to the composition comprising red blood cells, where the buffering capacity itself provides improved quenching. For example, using a cysteine analog such as methionine as a quencher, when appropriately modified to provide a suitable pH change in the red blood cell composition, will result in some level of quenching of binding of the pathogen-inactivating compound to the red blood cells. As the sulfur atom in methionine is not nucleophilic, methionine does not provide any quenching other than providing the necessary pH of the solution. Thus, the combination of pH adjustment and a thiol group provides improved quenching. Proper adjustment of pH and base equivalent may also decrease the level of red blood cell dehydration during the inactivation period. A third feature that may be important for providing improved quenching in some embodiments, is selection of preferred quenchers that do not substantially penetrate inside of pathogens such as viruses and bacteria. Such quenchers provide adequate quenching in the extracellular environment, where detrimental reactions such as binding to red cell surfaces occur, without additional quenching of pathogen-inactivating compound once it has penetrated inside of the pathogen. Finally, the improved quenching methods of the present invention include decreasing the quencher concentration following inactivation and, in some cases, adding an additive solution for storage. The red blood cells have been shown to have improved lifespan and decreased levels of dehydration during storage when the overall concentration of quencher is decreased to suitable levels.

In one aspect, the present invention provides a method of treating a red blood cell composition comprising: a) providing i) a pathogen-inactivating compound comprising a functional group which is, or which forms, a reactive electrophilic group (e.g., an effective amount of a pathogen-inactivating compound to inactivate a pathogen, if present), ii) a quencher (e.g., an effective amount of a quencher as described herein) comprising a thiol group, wherein the thiol is capable of reacting with the reactive electrophilic group of the pathogen-inactivating compound, and iii) a composition comprising red blood cells; b) mixing the pathogen-inactivating compound and quencher with the composition comprising red blood cells; and c) sufficiently decreasing the concentration of the quencher in the mixture to an amount which reduces the level of red blood cell dehydration resulting from storage of the mixture, relative to the level of red blood cell dehydration resulting from storage of the mixture at the original concentration of quencher. In some embodiments, step (a) further comprises providing a suitable base, step (b) further comprises mixing the base with the composition comprising red blood cells, and the base is of sufficient amount to reduce the level of an unwanted reaction of the pathogen-inactivating compound with red blood cells in the mixture, relative to the mixture without the base. In some embodiments, the unwanted reaction of the pathogen-inactivating compound with red blood cells is modification of the surface of the red blood cells by the pathogen-inactivating compound. In some embodiments, step (a) further comprises providing a suitable base, step (b) further comprises mixing the base with the composition comprising red blood cells, and the base is of sufficient amount to reduce the level of anti-pathogen inactivating compound antibody binding to the treated red blood cell composition in the resulting mixture by at least about 5% (or at least about 10%, at least about 25%, at least about 50%, at least about 75%, or at least about 90%) relative to the mixture without the base. In some embodiments, storage of the mixture is greater than, equal to, or less than 7, 10, 14, 21, 28, 35, or 42 days of storage at 4° C. or room temperature. In some embodiments, the mixture is stored in an additive solution (e.g., any additive solution described in Table 2, and/or an additive solution comprising sodium chloride, adenine, glucose, phosphate, guanosine, citrate and/or mannitol). In some embodiments, the method further comprises replacing the solution used during treatment with an additive solution (e.g., any additive solution described in Table 2, and/or an additive solution comprising sodium chloride, adenine, glucose, phosphate, guanosine, citrate and/or mannitol).

In an additional aspect, the invention provides a method of reducing dehydration in red blood cells, comprising: a) providing a red blood cell composition comprising i) a quencher, where the quencher is capable of reacting with a pathogen-inactivating compound, and ii) red blood cells; and b) sufficiently decreasing the concentration of the quencher in the mixture to an amount which reduces the level of red blood cell dehydration resulting from storage of the mixture relative to the level of red blood cell dehydration resulting from storage of the mixture at the original concentration of quencher. In some embodiments, storage of the mixture is greater than, equal to, or less than 7, 10, 14, 21, 28, 35, or 42 days of storage at 4° C. or room temperature. In some embodiments, the method further comprises the addition of an additive solution (e.g., any additive solution described in Table 2, and/or an additive solution comprising sodium chloride, adenine, glucose, phosphate, guanosine, citrate and/or mannitol), e.g., prior to storage.

The quencher and/or added base (or the neutralized quencher) used in the methods described herein may be mixed with the red blood cell composition prior to, at the same time as, or after addition of the pathogen-inactivating compound to the red blood cell composition. If the quencher and base (or neutralized quencher) are mixed with the red blood cell composition after the pathogen-inactivating solution is mixed with the red blood cell composition, the quencher and/or base (or neutralized quencher) are preferably added to the red blood cell composition before a significant amount of side reaction of the pathogen-inactivating compound with the red blood cells has occurred, so that adequate quenching of the undesired side reaction can be achieved. In some embodiments, the quencher and/or base (or neutralized quencher) is mixed with the red blood cell composition within about an hour, within about 30 minutes, within about 20 minutes, within about 10 minutes, within about 5 minutes, within about 2 minutes, or within about 1 minute after mixing the pathogen-inactivating compound with the red blood cell composition. In some embodiments, the quencher and base are mixed with the red blood cell composition at the same time as the pathogen-inactivating compound.

In some embodiments of each of the methods described herein, the quencher and the added base (or the neutralized quencher) are pretreated with the red blood cell composition for a suitable time interval prior to addition of the pathogen-inactivating compound (e.g., S-303), such as less than about an hour, less than about 30 minutes, less than about 20 minutes, less than about 10 minutes, less than about 5 minutes, less than about 2 minutes, or less than about 1 minute before mixing the pathogen-inactivating compound with the red blood cell composition. In some further embodiments, the pretreatment is at a temperature of about 1° C. to 30° C., also about 18° C. to 25° C., or about 37° C., or about room temperature.

In some embodiments of each of the methods described herein, the pathogen-inactivating compound (e.g., S-303) is incubated with the red blood cell composition in the presence of the quencher and the added base (or the neutralized quencher) for a suitable time interval, such as for about 30 minutes to 48 hours, also about 2 to 36 hours, also about 8 to 24 hours, also about 20 hours. In some further embodiments, the incubation is in a temperature range of about 1° C. to 30° C., also about 18° C. to 25° C., or about 37° C., or about room temperature.

With respect to the feature of adjusting the pH of the red blood cell composition, the previous methods of quenching such pathogen-inactivating compounds fail to recognize the importance of the pH of the resulting mixture with respect to both quenching effectiveness and cell vitality during inactivation. While the previous methods have demonstrated the need for sufficient base and suitable pH level for adequately quenching unwanted side reactions of the pathogen-inactivating compound (e.g., by increasing the levels of non-protonated glutathione to reduce binding of the pathogen-inactivating compound to the RBC surface), these methods do not realize and describe the effects of the increased base on cell dehydration during the inactivation process. Thus, one aspect of the present invention involves adjusting the pH of the red blood cell composition to a suitable level for the incubation of the pathogen-inactivating compound and quencher (e.g., a suitable level to avoid adversely affecting dehydration).

In some embodiments, upon mixing the pathogen-inactivating compound and quencher with the red blood cell composition, the pH of the mixture is at suitable level to reduce unwanted side reactions of the pathogen-inactivating compound (e.g., binding of the pathogen-inactivating compound to the RBC surface which may lead to an undesired immune response) and sufficiently reduce cell dehydration during inactivation. In some embodiments, the unwanted side reaction is modification of the surface of the red blood cells by the pathogen-inactivating compound. In some embodiments, the modification is covalent binding of the pathogen-inactivating compound to the surface of the red blood cells. In other embodiments, the modification is non-covalent binding of the pathogen-inactivating compound to the surface of the red blood cells.

As described herein, in some embodiments of each of the methods, an undesired (also referred to herein as "unwanted") side reaction of the pathogen inactivating compound with the red blood cells is reduced. In some embodiments, the undesired side reaction that is reduced is modification of the red blood cell surface by the pathogen inactivating compound. In some embodiments, the level of side reaction is reduced by at least about 5%, at least about 10%, at least about 25%, at least about 50%, at least about 75%, or at least about 90%. The decrease in the side reaction may be evidenced, for example, by measuring the amount of binding to the treated red blood cells of antibodies specific to the pathogen inactivating compound and/or measuring the life span of the treated red blood cells in vivo, and comparing these measurements to red blood cells treated by a second, different method (for example, a method without sufficient quencher and/or base added to the reaction mixture, a method in which no quencher and/or base is added to the reaction mixture, and/or a treatment at a lower pH). For instance, in some embodiments of the methods described herein, the level of anti-pathogen inactivating compound antibody binding to the treated blood cells is decreased by at least about 10%, at least about 25%, at least about 50%, at least about 75%, or at least about 90%, relative to a second method (e.g., a method without sufficient quencher and/or base added to the reaction mixture, a method in which no quencher and/or base is added to the reaction mixture, and/or treatment at a lower pH).

In some embodiments, upon mixing the pathogen-inactivating compound and quencher with the red blood cell composition, the pH of the mixture is in the range of about 6.0 to 8.5, about 6.0 to 7.5, about 6.5 to 7.1, about 6.5 to 7.0, about 6.6 to 6.8, or about 6.6, 6.7, 6.8, or 6.9. While the pH in a red blood cell composition may change with time, it is desirable that the pH is in a desired range when quencher is added to the red blood cell composition, whether or not it already contains pathogen-inactivating compound. The methods of the present invention involve adding pathogen-inactivating compound and quencher to a red blood cell composition. The desired pH range is necessary upon the addition of both the pathogen-inactivating compound and quencher, regardless of the order of addition of the pathogen-inactivating compound and/or quencher to the red blood cell composition. In other words, once all three components have been mixed, the pH is within the desired range. In some embodiments, quencher is added prior to pathogen-inactivating compound. In some embodiments, pathogen-inactivating compound is added prior to quencher. In some embodiments, quencher and pathogen-inactivating compound are added essentially simultaneously. Thus, upon addition of pathogen-inactivating compound and quencher means at the point when both of the quencher and pathogen-inactivating compound have been mixed with the red blood cell composition. The desired pH can be achieved by several means, and is not limited as to when the pH of the red blood cell composition is adjusted, or in some embodiments, is not significantly adjusted from the natural pH of the blood product. For example, the desired pH of the red blood cell composition can be achieved by adjusting the pH. The pH adjustment may be done, for example, by addition of a suitable additive solution, such as a buffering solution, prior to adding the pathogen-inactivating compound and quencher. In some embodiments, the red blood cell composition may be washed one or more times with a suitable buffer before suspending in the same or other suitable buffer. Alternatively, the pH of the red blood cell composition can be adjusted simultaneously with the addition of either the pathogen-inactivating compound, the quencher, or both. In some embodiments, the pH is adjusted simultaneously with addition of the quencher. In some embodiments, the quencher is neutralized, such that addition of the neutralized quencher provides the desired pH range in the red blood cell composition. As an example, the neutralization of glutathione can be used to effect the necessary pH adjustments. In some embodiments, an appropriate level of neutralization of the glutathione can be used, for example by addition of 1 equivalent of base, to provide a quencher that, upon addition to a red blood cell composition, will provide the necessary pH adjustment of the composition. The appropriate neutralization will depend upon the quencher used. For example, when a peptide is used it may depend on the amino acid components of the peptide. In some embodiments, a quencher can be used that does not significantly affect the pH of the red blood cell composition. For example, use of a peptide comprising a cysteine that may further comprise one or more amino acids that result in a more neutral pH for a solution of the naturally isolated peptide. In some embodiments, the peptide further comprises at least one basic amino acid, such as arginine or lysine.

In some embodiments of the methods described herein, where a base is mixed with the red blood cell composition along with the pathogen-inactivating compound and quencher to increase the pH of the mixture to a desired level and/or to improve quenching of undesired side reactions, the base is a basic salt. The basic salt may first be dissolved in an aqueous solution prior to mixing with the red blood cell composition. In other embodiments, the salt may be added directly to the red blood cell composition in solid form. In some embodiments, the basic salt comprises the quencher and provides both the quencher and the base to the mixture. In some embodiments, the base used in the method is a strong base, such as NaOH. Typically, a strong base like NaOH will be dissolved first in aqueous solution prior to mixing with the red blood cell composition. In some embodiments, the strong base (e.g., in solution or solid form) is mixed with the quencher prior to mixing the quencher with the red blood cell composition. In some embodiments, the base is a basic buffer (added in sufficient quantities and having an appropriate pKa to bring the mixture to the desired pH range). If a basic buffer is used, the buffer will, in some embodiments, be a pharmaceutically acceptable buffer. In some embodiments, the buffer will have a titratable proton with a pKa in the range of about 7 to 8. Examples of buffers which can be used as basic buffers include, but are not limited to, N-(2-hydroxyethyl)-piperazine-N'-2-ethanesulfonic acid (HEPES), phosphate buffered saline (PBS), and sodium phosphate buffer. Other suitable basic buffers will be readily identifiable by one of ordinary skill in the art.

In some embodiments of each of the methods and compositions described herein, the pH of the mixture of red blood cells, quencher, pathogen-inactivating compound, and any added base is greater than about 5.5, greater than about 5.7, greater than about 6.0, greater than about 6.3, greater than about 6.5, greater than about 6.7, greater than about 7.0, or greater than about 7.2. In some embodiments of each of the methods and compositions described herein, the pH of the mixture of red blood cells, quencher, pathogen-inactivating compound, and base (if any is added) is in the range of about 6.0 to 8.5, about 6.0 to 7.5, about 6.5 to 7.1, about 6.5 to 7.0, or about 6.6 to 6.8, or about 6.6, 6.7, 6.8, or 6.9. In some embodiments, the indicated pH is the pH at room temperature. In some embodiments, the indicated pH is the pH at 37° C. For example, in some embodiments, the composition comprising the red blood cells are treated with the pathogen-inactivating compound in the presence of the quencher and any added base, wherein the pH of the mixture is in the range of about 6.5 to about 7.0 (or 7.1) at 37° C.

In some embodiments, the pH of the mixture of red blood cells, quencher, and the base (if base is added as part of the method) is in the range of about 6.0 to 8.5, about 6.0 to 7.5, about 6.5 to 7.1, about 6.5 to 7.0, or about 6.6 to 6.8, or about 6.5, 6.7, 6.8, or 6.9, prior to mixing the pathogen-inactivating compound with the red blood cell composition. In some other embodiments, the pH is achieved at the same time as or within about 1 hour, within about 30 minutes, within about 20 minutes, within about 10 minutes, within about 5 minutes, or within about 2 minutes of mixing the pathogen-inactivating compound with the composition comprising the red blood cells. In some embodiments of those methods where the pH is adjusted, the pH is adjusted to the desired pH range prior to, at the same time as, within about 1 hour, within about 30 minutes, within about 20 minutes, within about 10 minutes, within about 5 minutes, or within about 2 minutes of mixing the pathogen-inactivating compound with the composition comprising the red blood cells. In those embodiments, where the quencher is glutathione and the pathogen-inactivating compound is S-303, the pH of the mixture comprising the red blood cell composition and the quencher is preferably adjusted to the desired pH range (e.g., pH 6.5 to 7.0) prior to mixing the S-303 with the red blood cell composition.

In some embodiments, the resulting pH of the composition after mixing the red blood cells, quencher, and the base, is not necessarily an adjustment of the pH of the starting red blood cell composition. For example, a red blood cell composition may have a pH in the desired range of 6.0-7.5, and the pH of the composition does not change significantly on addition of quencher, and subsequently pathogen-inactivating compound. In such embodiments, the quencher either naturally provides the desired pH, or is neutralized accordingly to provide the desired pH. It is the combination of adding high initial amounts of quencher, such as about 5 mM to about 40 mM, with a resulting pH in the desired range that is important. Known methods using such concentrations of glutathione, for example, have not been used with the desired pH range in conjunction with other aspects of the present invention. Thus, for peptides, regardless of the peptide quencher, it can be effectively neutralized as needed to provide a suitable pH range when added to a red blood cell composition, and further may be selected to provide a suitable amount of buffering in the desired pH range. As such, a neutralized quencher means that the quencher is suitably titrated with acid or base as needed such that on addition to a red blood cell composition, the resulting mixture has a pH that provides better quenching of unwanted side reactions (e.g., binding of the pathogen-inactivating compound to the RBC surface which may lead to an undesired immune response) while avoiding cell dehydration during inactivation, such as a pH in the range of about 6.0 to 8.5, about 6.0 to 7.5, about 6.5 to 7.0, about 6.5 to 7.1, or about 6.6 to 6.8, or about 6.6, 6.7, 6.8, or 6.9. In some embodiments, the peptide as isolated naturally, is suitably neutralized, i.e. requires no addition of acid or base to provide the desired pH in the final mixture. Further, preferred quenchers will provide buffering capacity to maintain the pH in the desired range for a time necessary to quench unwanted side reactions.

In some embodiments of each of the methods and compositions described herein, the quencher is neutralized. A quencher is said to be "neutralized" by a base, if a sufficient amount of the base has been combined with the quencher, such that the quenching of an undesired side reaction between the pathogen-inactivating compound and the red blood cells is improved in a mixture comprising the composition comprising the red blood cells, the pathogen-inactivating compound, and quencher. A "neutralized quencher" does not necessarily have a neutral pH, nor is it necessarily uncharged. In some embodiments, the neutralized quencher is neither in its most protonated form nor its most deprotonated form. In some embodiments, where the quencher is very acidic, the pH of the neutralized quencher may still be lower than 7.0 (e.g., about 6.6, 6.7, 6.8, or 6.9). In some embodiments, the pH of solution of the neutralized quencher may be greater than 7.0. In some embodiments, the pH of the solution of the neutralized quencher will be detectably higher than that of the quencher prior to addition of the base. In some embodiments, the quencher is neutralized with at least about 0.25 equivalents, at least about 0.5 equivalents, at least about 0.75 equivalents, at least about 1 equivalent, at least about 1.25 equivalents, at least about 1.5 equivalents, or at least about 2 equivalents of a base. In some embodiments, the quencher is neutralized with less than about 2 equivalents, less than about 1.5 equivalents, less than about 1.25 equivalents, less than about 1 equivalent, or less than about 0.75 equivalents of a base. In some embodiments, the quencher is neutralized with about 0.25 to about 2 equivalents, about 0.5 to about 1.5 equivalents, or about 0.75 to about 1.25 equivalents of base. In some embodiments, the quencher is neutralized with about 0.75 equivalent of base. In other embodiments, the quencher is neutralized with about 1 equivalent of base. In other embodiments, the quencher is neutralized with about 1.25 equivalent of base. For example, In some embodiments of the invention, glutathione is neutralized with about 1 equivalent of a suitable base, such as sodium hydroxide. In this instance, a solution of the protonated glutathione has a pH of approximately 3, a solution neutralized with 1 equivalent of sodium hydroxide has a pH of approximately 4.5, and a solution neutralized with 2 equivalents of sodium hydroxide has a pH of approximately 9.5. Any appropriate peptide quencher comprising at least one cysteine can be suitably adjusted to provide the desired pH upon addition to the red blood cell composition.

Appropriate methods for neutralizing glutathione and other quenchers will be readily apparent to those of ordinary skill in the art. In some embodiments, sodium hydroxide is used to neutralize or partially neutralize the quencher. In some embodiments, solid pellets of NaOH are first dissolved in water to generate a concentrated solution of the base, such as a 1 N, 5 N, 10 N, or 20 N NaOH solution. In some embodiments, an appropriate amount of that NaOH solution is then added to the quencher either prior to, at the same time as, or following addition of the quencher to the mixture. Alternatively, the NaOH is added to the red blood cell composition or the pathogen-inactivating compound, or the combination of the two, prior to the addition of the quencher to the mixture.

In addition to providing a quencher that is suitably pH-adjusted or neutralized, in some embodiments, preferred quenchers are not able to significantly enter into the pathogens, such that they optimally quench unwanted reactions in the extracellular environment, but do not interfere with pathogen inactivation once the pathogen-inactivating compound has penetrated inside of the pathogen.

In some embodiments of each of the methods described herein, the quencher is an acidic compound. In some embodiments, the quencher is provided in the free acid form. In some embodiments, the quencher is acidic and at least about 1 equivalent of base is added to neutralize the quencher. A solution comprising such a neutralized quencher may be, in some instances, basic, neutral, or even acidic. In some embodiments, about 1 equivalent of base is added to neutralize or partially neutralize the quencher. In some embodiments, about 2 equivalents of base are added. In some embodiments, the quencher is acidic and about 0.5 to about 1.5 equivalents of base is used to neutralize the quencher. In some embodiments, about 0.75 to about 1.25 equivalents of base are used. In some embodiments, about 1 equivalent of base is used.

In some embodiments, the quencher is neutralized prior to addition to the red blood cell composition and/or pathogen-inactivating compound. In other embodiments, the quencher is neutralized after combining the quencher with either the red blood cell composition and/or pathogen-inactivating compound. In some embodiments, the pH of the neutralized quencher prior to addition to the red blood cell composition and/or pathogen-inactivating compound is in the range of about 2.5 to 7.5, about 3.0 to 6.5, about 3.5 to 5.5, about 4.0 to 5.0, or about 4.3 to 4.5, or about 4.4.

In some embodiments, the quencher is glutathione and is provided in the form of glutathione monosodium salt and is neutralized with about 1 equivalent of base, or is not neutralized with base. In some other embodiments, the quencher is glutathione and is provided in the form of glutathione hydrochloride salt and is neutralized with about 1 equivalent of base.

In some embodiments of each of the methods described herein, the initial concentration of the quencher in the mixture comprising the red blood cell composition, quencher, pathogen-inactivating compound, and any added base is elevated during a period for inactivation, and then reduced to a lowered concentration following the period of inactivation. In some embodiments, the initial concentration of the quencher is adequate to sufficiently reduce unwanted side reactions of the pathogen-inactivating compound (e.g., binding of the pathogen-inactivating compound to the RBC surface), then reduced to a lowered concentration to sufficiently reduce adversely affecting the vitality (e.g., osmotic fragility and dehydration) and/or lifespan during cell storage.

The invention embraces any number of methods used to reduce the concentration of quencher following the period of pathogen inactivation. In some embodiments, the concentration of quencher (e.g., glutathione) is reduced by centrifugation of the mixture comprising the red blood cell composition, quencher, and pathogen-inactivating compound, followed by removal of the supernatant of the mixture, then the addition of fresh solution, such as an additive solution (e.g., any additive solution described in Table 2, and/or an additive solution comprising sodium chloride, adenine, glucose, phosphate, guanosine, citrate and/or mannitol), for resuspension of the cells (e.g., via washing the cells). The process of centrifugation, supernatant removal, and addition of fresh solution (e.g., any additive solution described in Table 2, and/or an additive solution comprising sodium chloride, adenine, glucose, phosphate, guanosine, citrate and/or mannitol), may be, in some embodiments, repeated for an additional 1, 2, 3, 4, or 5 or more times. In some embodiments, the method used to reduce the concentration of the quencher is automated. In some embodiments, the fresh solution does not comprise the quencher or comprises a lower concentration of the quencher. In some embodiments, the concentration of quencher (e.g., glutathione) is reduced by chemically deactivating the quencher. In some embodiments, the concentration of quencher (e.g., glutathione) is reduced by adsorption in a batch or flow removal process or size exclusion in flow process using membranes (e.g., hollow fiber membranes or dialysis membranes), or size exclusion beads. In some embodiments, the quencher is not reduced and/or is not contacted with a compound adsorption device (CAD).

In some embodiments of each of the methods and compositions described herein, the initial concentration of the quencher (e.g., glutathione) in the mixture comprising the red blood cell composition, quencher, pathogen-inactivating compound, and any added base is greater than about 2 mM, greater than about 4 mM, greater than about 6 mM, greater than about 8 mM, greater than about 10 mM, greater than about 15 mM, or greater than about 20 mM. In some embodiments, the initial quencher concentration in the mixture is in the range of about 2 mM to 100 mM, about 2 mM to 40 mM, about 4 mM to 40 mM, about 5 mM to 40 mM, about 5 mM to 30 mM, or about 10 mM to 30 mM, or up to 2 mM, 5 mM, 10 mM, 15 mM, 20 mM, 25 mM, 30 mM, 35 mM, 40 mM, 45 mM, 50 mM, or 100 mM. In some embodiments, the initial quencher concentration in the mixture is about 20 mM.

In some embodiments of each of the methods and compositions described herein, the initial concentration of quencher (e.g., glutathione) in the mixture of red blood cells, quencher, and the pathogen-inactivating compound is greater than about 2 mM, greater than about 4 mM, greater than about 6 mM, greater than about 8 mM or greater than about 10 mM, and the pH of the mixture is greater than about 5.5, greater than about 5.7, greater than about 6.0, greater than about 6.3, greater than about 6.5, greater than about 6.7, greater than about 7.0, or greater than about 7.2. In some embodiments of each of the methods and compositions described herein, the initial concentration of the quencher in the mixture is in the range of about 2 mM to 40 mM, about 4 mM to 40 mM, about 5 mM to 40 mM, about 5 mM to 30 mM, or about 10 mM to 30 mM, or about 20 mM, and the pH of the mixture is in the range of about 6.0 to 8.5, about 6.0 to 7.5, about 6.5 to 7.1, about 6.5 to 7.0, or about 6.6 to 6.8, or about 6.6, 6.7, 6.8, or 6.9. In some embodiments, the initial concentration of quencher in the mixture is greater than about 2 mM, greater than about 4 mM, greater than about 6 mM, greater than about 8 mM or greater than about 10 mM, and the pH of the mixture is in the range of about 6.0 to 8.5, about 6.0 to 7.5, about 6.5 to 7.1, about 6.5 to 7.0, or about 6.6 to 6.8, or about 6.6, 6.7, 6.8, or 6.9. In some embodiments, the concentration of quencher (e.g., glutathione) in the mixture is in the range of about 10 mM to about 30 mM, and the pH of the mixture is in the range of about 6.0 to 7.5. In some embodiments, the concentration of quencher (e.g., glutathione) in the mixture is in the range of about 20 mM, and the pH of the mixture is in the range of about 6.5 to 7.0 (or 7.1).

In some embodiments of each of the methods and compositions described herein, the initial concentration of the quencher (e.g., glutathione) in the mixture comprising the red blood cell composition, quencher, pathogen-inactivating compound and any added base following the period of inactivation is reduced by greater than 2-fold, or 3-fold, or 4-fold, or 5-fold, or 6-fold, or 7-fold, or 8-fold, 9-fold, or 10-fold, or 15-fold, or 20-fold, or 25-fold, or 30-fold, or 35-fold, or 40-fold, or 50-fold, or 100-fold, or 500-fold, or 1000-fold relative to the initial concentration of the quencher (e.g., glutathione) in the mixture.

In some embodiments of each of the methods and compositions described herein, the lowered concentration of the quencher (e.g., glutathione) in the mixture comprising the red blood cell composition, quencher, pathogen-inactivating compound and any added base following the period of inactivation is less than about 15 mM, less than about 10 mM, less than about 8 mM, less than about 6 mM, less than about 5 mM, less than about 4 mM, less than about 3 mM, less than about 2 mM, less than about 1 mM, less than about 0.75 mM, less than about 0.5 mM, or less than about 0.25 mM. In some embodiments, the lowered concentration of the quencher in the mixture following the period of inactivation is in the range of about 1 mM to 20 mM, about 2 mM to 15 mM, about 3 mM to 10 mM, about 4 mM to 8 mM, or about 5 mM to 6 mM. In some embodiments, the lowered concentration of the quencher in the mixture following the period of inactivation is at a concentration of up to about 0.25 mM, or 0.5 mM, or 0.75 mM, or 1 mM, or 1.5 mM, or 2 mM, or 3 mM, or 4 mM, or 5 mM, or 6 mM, or 7 mM, or 8 mM, or 9 mM, or 10 mM, or 12.5 mM, or 15 mM, or 20 mM.

In some embodiments of each of the methods and compositions described herein, the initial concentration of the quencher (e.g., glutathione) in the mixture comprising the red blood cell composition, quencher, pathogen-inactivating compound and any added base is greater than 2 mM, greater than about 4 mM, greater than about 6 mM, greater than about 8 mM or greater than about 10 mM, and the lowered concentration of the quencher in the mixture following the period of inactivation is less than about 15 mM, less than about 10 mM, less than about 8 mM, less than about 6 mM, less than about 5 mM, less than about 4 mM, less than about 3 mM, less than about 2 mM, less than about 1.5 mM, less than about 1 mM, less than about 0.75 mM, less than about 0.5 mM, or less than about 0.25 mM. In some embodiments, the initial concentration of the quencher is in the range of about 2 mM to 100 mM, about 2 mM to 40 mM, about 4 mM to 40 mM, about 5 mM to 40 mM, about 5 mM to 30 mM, or about 10 mM to 30 mM, or about 20 mM, and the lowered concentration of the quencher in the mixture following the period of inactivation is in the range of about 1 mM to 20 mM, about 2 mM to 15 mM, about 3 mM to 10 mM, about 4 mM to 8 mM, or about 5 mM to 6 mM. In some embodiments, the initial concentration of the quencher (e.g., glutathione) is in the range of about 10 mM to 30 mM, and the lowered concentration of the quencher in the mixture following the period of inactivation is in the range of about 2 mM to 15 mM. In some embodiments, the initial concentration of the quencher (e.g., glutathione) is about 20 mM, and the lowered concentration of the quencher in the mixture following the period of inactivation is in the range of about 4 mM to 8 mM.

In some embodiments, the initial concentration of the quencher (e.g., glutathione) in the mixture comprising the red blood cell composition, quencher (e.g., glutathione), pathogen-inactivating compound and any added base is greater than 2 mM, greater than about 4 mM, greater than about 6 mM, greater than about 8 mM or greater than about 10 mM; the pH of the mixture is greater than about 5.5, greater than about 5.7, greater than about 6.0, greater than about 6.3, greater than about 6.5, greater than about 6.7, greater than about 7.0, or greater than about 7.2; and the lowered concentration of the quencher in the mixture following the period of inactivation is less than about 15 mM, less than about 10 mM, less than about 8 mM, less than about 6 mM, less than about 5 mM, less than about 4 mM, less than about 3 mM, less than about 2 mM, less than about 1.5 mM, less than about 1 mM, less than about 0.75 mM, less than about 0.5 mM, or less than about 0.25 mM. In some embodiments, the initial concentration of the quencher is in the range of about 2 mM to 100 mM, about 2 mM to 40 mM, about 4 mM to 40 mM, about 5 mM to 40 mM, about 5 mM to 30 mM, or about 10 mM to 30 mM, or about 20 mM; the pH of the mixture is in the range of about 6.0 to 8.5, about 6.0 to 7.5, about 6.5 to 7.0, about 6.5 to 7.1, or about 6.6 to 6.8, or about 6.6, 6.7, 6.8, or 6.9; and the lowered concentration of the quencher in the mixture following the period of inactivation is in the range of about 1 mM to 20 mM, about 2 mM to 15 mM, about 3 mM to 10 mM, about 4 mM to 8 mM, or about 5 mM to 6 mM. In some embodiments, the initial concentration of the quencher (e.g., glutathione) is in the range of about 10 mM to 30 mM; the pH of the mixture is in the range of about 6.0 to 7.5; and the lowered concentration of the quencher in the mixture following the period of inactivation is in the range of about 2 mM to 15 mM. In some embodiments, the initial concentration of the quencher (e.g., glutathione) is about 20 mM; the pH of the mixture is in the range of about 6.5 to 7.0 (or 7.1); and the lowered concentration of the quencher in the mixture following the period of inactivation is in the range of about 4 mM to 8 mM.

In some embodiments of each of the methods and compositions described herein, the period of time between the point of addition of the quencher at the initial concentration and the point of reducing the concentration of the quencher to a lowered concentration in the mixture comprising the red blood cell composition, quencher, pathogen-inactivating compound, and any added base is sufficient to reduce unwanted side reactions of the pathogen-inactivating compound (e.g., binding of the pathogen-inactivating compound to the RBC surface which may lead to an undesired immune response). In some embodiments, the period of time is sufficient to reduce unwanted side reactions of the pathogen-inactivating compound and to avoid or reduce cell dehydration during the inactivation process.

In some embodiments, the period of time between the point of addition of the quencher at the initial concentration and the point of reducing the concentration of the quencher to a lowered concentration in the mixture comprising the red blood cell composition, quencher, pathogen-inactivating compound, and any added base is greater than, about equal to, or less than 5 hours, 10 hours, 15 hours, 20 hours, 25 hours, 30 hours, 35 hours, 40 hours, or 50 hours. In some embodiments, the period of time is about 1 to 96 hours, or about 1 to 72 hours, or about 1 to 48 hours, or about 10 to 30 hours, or about 15 to 25 hours, or about 20 hours.

In some embodiments of each of the methods and compositions described herein, the initial concentration of the quencher (e.g., glutathione) in the mixture comprising the red blood cell composition, quencher, pathogen-inactivating compound and any added base is greater than 2 mM, greater than about 4 mM, greater than about 6 mM, greater than about 8 mM, greater than about 10 mM, or greater than about 15 mM; the lowered concentration of the quencher in the mixture following the period of inactivation is less than about 25 mM, less than about 20 mM, less than about 15 mM, less than about 10 mM, less than about 8 mM, less than about 6 mM, less than about 5 mM, less than about 4 mM, less than about 3 mM, less than about 2 mM, less than about 1.5 mM, less than about 1 mM, less than about 0.75 mM, less than about 0.5 mM, or less than about 0.25 mM; and the period of time between the point of addition of the quencher at the initial concentration and the point of reducing the concentration of the quencher to a lowered concentration is greater than, about equal to, or less than 5 hours, 10 hours, 15 hours, 20 hours, 25 hours, 30 hours, 35 hours, 40 hours, or 50 hours.

In some embodiments, the initial concentration of the quencher is in the range of about 2 mM to 100 mM, about 2 mM to 40 mM, about 4 mM to 40 mM, about 5 mM to 40 mM, about 5 mM to 30 mM, or about 10 mM to 30 mM, or about 20 mM; the lowered concentration of the quencher in the mixture following the period of inactivation is in the range of about 1 mM to 20 mM, about 2 mM to 15 mM, about 3 mM to 10 mM, about 4 mM to 8 mM, or about 5 mM to 6 mM; and the period of time between the point of addition of the quencher at the initial concentration and the point of reducing the concentration of the quencher to a lowered concentration is about 1 to 96 hours, or about 1 to 72 hours, or about 1 to 48 hours, or about 10 to 30 hours, or about 4 to 30 hours, or about 10 to 25 hours, or about 15 to 25 hours, or about 20 hours.

In some embodiments, the initial concentration of the quencher (e.g., glutathione) is in the range of about 10 mM to 30 mM; the lowered concentration of the quencher in the mixture following the period of inactivation is in the range of about 2 mM to 15 mM; and the period of time between the point of addition of the quencher at the initial concentration and the point of reducing the concentration of the quencher to a lowered concentration is about 10 to 30 hours. In some embodiments, the initial concentration of the quencher (e.g., glutathione) is about 20 mM; and the lowered concentration of the quencher in the mixture following the period of inactivation is in the range of about 4 mM to 8 mM; and the period of time between the point of addition of the quencher at the initial concentration and the point of reducing the concentration of the quencher to a lowered concentration is about 15 to 25 hours. In some of these embodiments, the pH of the mixture is in the range of about 6.5 to 7.0 (or 7.1). In other of these embodiments, the pH of the mixture is in the range of about 6.0 to 7.5.

In any of these embodiments, the temperature of the mixture comprising the red blood cell composition and quencher during the period of time between the point of addition of the quencher at the initial concentration and the point of reducing the concentration of the quencher to a lowered concentration in is in a temperature range of about 1° C. to 30° C., also about 18° C. to 25° C., or about 37° C., or about room temperature.

In some embodiments, the present invention provides a method of treating a red blood cell composition comprising: a) providing i) a pathogen-inactivating compound (e.g., an effective amount of a pathogen-inactivating compound to inactivate a pathogen, if present) comprising a frangible linker linking a mustard group and a nucleic acid-binding ligand (e.g., S-303), ii) a quencher (e.g., an effective amount of a quencher) comprising a thiol group, wherein the thiol is capable of reacting with the reactive electrophilic group of the pathogen-inactivating compound (e.g., glutathione), iii) a composition comprising red blood cells, and iv) a suitable base (e.g., NaOH); b) mixing the pathogen-inactivating compound, quencher, and suitable base with the composition comprising red blood cells; and c) sufficiently decreasing the concentration of the quencher in the mixture to an amount which reduces the level of red blood cell dehydration resulting from storage of the mixture (e.g., after 10, 28, or 42 days at 4° C.), relative to the level of red blood cell dehydration resulting from storage of the mixture at the original concentration of quencher. In some embodiments, the mixture comprises about 0.5 to 1.5 equivalents of base (or about 0.75 to 1.25 equivalents), where an equivalent means a molar amount that is equivalent to the molar amount of quencher in the mixture, and/or the resulting mixture of step (b) has a pH at 37° C. of about 6.0 to 7.5 (or about 6.5 to 7.0, or 7.1). In some embodiments, the base of step (a) is of sufficient amount to reduce the level of anti-pathogen inactivating compound antibody binding to the treated red blood cell composition in the resulting mixture by at least about 5% (or at least about 10%, at least about 25%, at least about 50%, at least about 75%, or at least about 90%) relative to the mixture without the base. In some embodiments, the quencher concentration is about 5 mM to about 30 mM (or about 15 mM to about 25 mM) and/or the quencher in the resulting mixture of step (c) is at a concentration of less than about 10 mM (or less than about 6 mM, or less than about 2 mM). In some embodiments, the concentration of the pathogen inactivation compound in the resulting mixture of step (b) is about 0.1 μM to about 5 mM and/or is sufficient to inactivate at least 1 log (or 3 log) of a pathogen in the red blood cell composition, if present. In some embodiments, the time between step (b) and step (c) is about 1 to 48 hours (or 15 to 25 hours). In some embodiments, at 20 hours following step (b), the red blood cells (RBCs) of the resulting mixture have an antibody binding capacity (ABC) of less than 65% compared to the ABC value of red blood cells from the same method under the same conditions, but without the use of base and/or have an average ABC of less than about 50,000 (or between about 25,000 and 70,000), and/or have less then 1% hemolysis following step (c) (or following storage for 28 or 42 days at 4° C.) and/or have a Packed Cell Volume (PCV) of greater than 50% following step (c) (or following storage for 28 or 42 days at 4° C.) and/or have a Median Corpuscular Fragility value greater than 140 (or 150) after 28 (or 42) days at 4° C. following step (c). In some of these embodiments, decreasing the concentration of the quencher in step (c) comprises removal of the solution used during inactivation and addition of a final additive solution (e.g., any solution described in herein, such as SAG-M, AS-5, any solution of Tables 2, 3, or 4, or an additive solution comprising sodium chloride, adenine, glucose, phosphate, guanosine, citrate, and/or mannitol).

In some embodiments, the present invention provides a method of treating a red blood cell composition comprising (a) mixing (i) a pathogen-inactivating compound (e.g., an effective amount of a pathogen-inactivating compound to inactivate a pathogen, if present) comprising a functional group which is, or which forms, a reactive electrophilic group (e.g, S-303); (ii) a quencher (e.g., an effective amount of a quencher) comprising a thiol group (e.g., glutathione), wherein the thiol is capable of reacting with the reactive electrophilic group of the pathogen-inactivating compound; (iii) a composition comprising red blood cells; and (iv) a suitable base (e.g., NaOH), and; (b) sufficiently decreasing the concentration of the quencher in the mixture to an amount which reduces the level of red blood cell dehydration resulting from storage of the mixture relative to the level of red blood cell dehydration resulting from storage of the mixture (e.g., after 10, 28, or 42 days at 4° C.) at the original concentration of quencher. In some embodiments, the mixture comprises about 0.5 to 1.5 equivalents of base (or about 0.75 to 1.25 equivalents), where an equivalent means a molar amount that is equivalent to the molar amount of quencher in the mixture, and/or the resulting mixture of step (a) has a pH at 37° C. of about 6.0 to 7.5 (or about 6.5 to 7.0, or 7.1). In some embodiments, the base of step (a) is of sufficient amount to reduce the level of anti-pathogen inactivating compound antibody binding to the treated red blood cell composition in the resulting mixture by at least about 5% (or at least about 10%, at least about 25%, at least about 50%, at least about 75%, or at least about 90%) relative to the mixture without the base. In some embodiments, the quencher concentration is about 5 mM to about 30 mM (or about 15 mM to about 25 mM) and/or the quencher in the resulting mixture of step (b) is at a concentration of less than about 10 mM (or less than about 6 mM, or less than about 2 mM). In some embodiments, the concentration of the pathogen inactivation compound in the resulting mixture of step (a) is about 0.1 µM to about 5 mM and/or is sufficient to inactivate at least 1 log (or 3 log) of a pathogen in the red blood cell composition, if present. In some embodiments, the time between step (a) and step (b) is about 1 to 48 hours (or 15 to 25 hours). In some embodiments, at 20 hours following step (a), the red blood cells (RBCs) of the resulting mixture have an antibody binding capacity (ABC) of less than 65% compared to the ABC value of red blood cells from the same method under the same conditions, but without the use of base and/or have an average ABC of less than about 50,000 (or between about 25,000 and 70,000), and/or have less then 1% hemolysis following step (b) (or following storage for 28 or 42 days at 4° C.) and/or have a Packed Cell Volume (PCV) of greater than 50% following step (b) (or following storage for 28 or 42 days at 4° C.) and/or have a Median Corpuscular Fragility value greater than 140 (or 150) after 28 (or 42) days at 4° C. following step (b). In some of these embodiments, decreasing the concentration of the quencher in step (b) comprises removal of the solution used during inactivation and addition of a final additive solution (e.g., any solution described in herein, such as SAG-M, AS-5, any solution of Tables 2, 3, or 4, or an additive solution comprising sodium chloride, adenine, glucose, phosphate, guanosine, citrate, and/or mannitol).

In some embodiments, the present invention provides a method of reducing dehydration in red blood cells, comprising: a) providing a red blood cell composition comprising i) a quencher (e.g., glutathione), where the quencher is capable of reacting with a pathogen-inactivating compound, and ii) red blood cells; and b) sufficiently decreasing the concentration of the quencher in the mixture to an amount which reduces the level of red blood cell dehydration resulting from storage of the mixture relative to the level of red blood cell dehydration resulting from storage of the mixture at the original concentration of quencher (e.g., after 10, 28, or 42 days at 4° C.). In some embodiments, the quencher in the resulting mixture of step (b) is at a concentration of less than about 10 mM (or less than about 6 mM, or less than about 2 mM). In some embodiments, the red blood cells (RBCs) of the resulting mixture have less then 1% hemolysis following step (b) (or following storage for 28 or 42 days at 4° C.) and/or have a Packed Cell Volume (PCV) of greater than 50% following step (b) (or following storage for 28 or 42 days at 4° C.) and/or have a Median Corpuscular Fragility value greater than 140 (or 150) after 28 (or 42) days at 4° C. following step (b).

The methods of the invention include the ex vivo use of a pathogen-inactivating compound and a quencher. The ex vivo use involves using the compounds for treatment of a red blood cell composition, outside of a living human, mammal, or vertebrate, where the treated biological material is intended for use inside of a living human, mammal, or vertebrate. For example, removal of blood from a human, and introduction of a compound into that blood to inactivate pathogens, is defined as an ex vivo use of the compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo. Some embodiments of the present invention involve the ex vivo use of a quencher, where the red blood cell composition is intended for in vivo use. In some instances, some level of quencher remains in the red blood cell composition such that the quencher is also introduced in vivo. The in vitro use of a material or compound involves a use of the material or compound outside of a living human, mammal, or vertebrate, where the material or compound is not intended for reintroduction into a living human, mammal, or vertebrate. An example of an in vitro use would be the diagnostic analysis of components of a red blood cell sample. The methods of the invention may be applied to the in vitro use of the red blood cell compositions, as modification of the red blood cells or other constituents may affect the in vitro analysis of the components of the blood sample. Thus, the methods of the invention may provide safety in handling of such in vitro samples with adequate quenching of modifications of the sample that might otherwise interfere with diagnostic testing of the sample.

Additive solutions, including salts and/or buffered solutions, may be used with the methods and red blood cell compositions described herein. For example, a selected buffer (e.g., SAG-M, AS-5, or any solution described in Tables 2, 3, and/or 4) may be added to the red blood cell composition prior to, during, and/or following the period of inactivation and/or at the time the quencher concentration is decreased.

Methods of Inactivation Using Packed Red Blood Cells

In some embodiments, packed red blood cells (pRBCs) (e.g., red blood cells lacking additive solution and/or having a hematocrit in the range of about 70 to 90%, or about 75 to 85%, or about 80%) are subjected to an inactivation method described herein (e.g., a method wherein the composition comprises about 20 mM GSH with about 1 equivalent base and about 0.2 mM S-303), then subjected to (in some cases, preserved with) an additive solution (e.g., SAG-M, AS-5, or any solution described herein or in Table 2). Examples of additive solutions are shown in Table 2 and described herein. In some of these embodiments, the additive solution (e.g., any solution described herein or in Table 2) is added to the red blood cell composition comprising quencher, pathogen-inactivating compound, and any added base, from about 5 minutes to 20 hours following the addition of the pathogen-inactivating compound (e.g., S-303) and/or the quencher (e.g., GSH). In some embodiments, the additive solution is added to the RBC composition from about 5 minutes to 10 hours, or about 5 minutes to 5 hours, or about 5 minutes to 60 minutes, or about 5 minutes to 30 minutes, or about 10 minutes to 20 minutes, or about 15 minutes following the addition of the pathogen-inactivating compound (e.g., S-303) and/or the quencher (e.g., GSH). In some embodiments, the concentration of the quencher is decreased as described herein following the addition of the additive solution (e.g., SAG-M, AS-5, or any solution described herein or in Table 2). For example, pRBCs may be treated with an inactivation method described herein (e.g., treatment wherein the composition comprises about 20 mM GSH, about 1 equivalent base, and about 0.2 mM S-303), then treated with an additive solution (e.g., SAG-M, AS-5, or any solution described herein or in Table 2) at a specified time after the addition of the pathogen-inactivating compound and/or the quencher (such as at about 5 minutes to 5 hours, or about 10 minutes to 20 minutes, or about 15 minutes), followed by decreasing of the quencher concentration as described herein (e.g., to less than about 10 mM, or less than about 5 mM). In some of these embodiments, decreasing the quencher concentration comprises removal of the treatment solution and/or additive solution, followed by the addition of a final additive solution (e.g., SAG-M, AS-5, or any solution described herein or in Table 2) to provide a red blood cell composition having, e.g., a hematocrit in the range about 50 to 70%, or about 55 to 65%, or about 60%. In some embodiments, the concentration of chloride ion in the red blood cell composition prior to and/or during inactivation is less than or greater than about 150 mM, or about 120 mM, or about 100 mM, or about 90 mM, about 80 mM, or about 70 mM, or about 60 mM, or about 50 mM, about 40 mM, about 30 mM, or about 20 mM, about 10 mM, or between about 25 and 250 mM, or about 40 and 100 mM, or about 50 and 75 mM, or about 60 and 70 mM, or about 65 mM.

In some embodiments, the additive solution referred to herein (e.g., the additive solution administered prior to and/or following decrease of the quencher concentration) comprises one or more of the following components: dextrose, adenine, guanosine, mannitol, citrate (e.g., sodium citrate), citric acid, phosphate (e.g., $Na_2HPO_4$ and/or $NaH_2PO_4$) and chloride (e.g., from sodium chloride). In some embodiments, the concentration of dextrose of the additive solution and/or the final concentration of dextrose in the RBC composition following exchange (e.g., prior to transfusion) is at a concentration from about 10 mM to about 150 mM, or about 20 mM to about 120 mM, or about 25 mM to about 100 mM, or about 30 mM to about 75 mM, or about 40 mM to about 50 mM. In some embodiments, the concentration of adenine of the additive solution and/or the final concentration of adenine in the RBC composition following exchange (e.g., prior to transfusion) is at a concentration from about 0.5 mM to about 5 mM, or about 0.75 mM to about 3 mM, or about 1 mM to about 2.5 mM. In some embodiments, the concentration of guanosine of the additive solution and/or the final concentration of guanosine in the RBC composition following exchange (e.g., prior to transfusion) is at a concentration from about 0.5 mM to about 5 mM, or about 0.75 mM to about 3 mM, or about 1 mM to about 2.5 mM, or about 1.5 mM to about 2 mM. In some embodiments, the concentration of mannitol of the additive solution and/or the final concentration of mannitol in the RBC composition following exchange (e.g., prior to transfusion) is at a concentration from about 10 mM to about 150 mM, or about 20 mM to about 120 mM, or about 25 mM to about 100 mM, or about 30 mM to about 75 mM, or about 40 mM to about 50 mM, or about 35 mM to about 45 mM. In some embodiments, the concentration of citrate (e.g., sodium citrate) of the additive solution and/or the final concentration of citrate in the RBC composition following exchange (e.g., prior to transfusion) is at a concentration from about 5 mM to about 100 mM, or about 10 mM to about 75 mM, or about 15 mM to about 50 mM, or about 15 mM to about 35 mM, or about 20 mM to about 30 mM. In some embodiments, the concentration of phosphate (e.g., $Na_2HPO_4$ and/or $NaH_2PO_4$) of the additive solution and/or the final concentration of phosphate in the RBC composition following exchange (e.g., prior to transfusion) is at a concentration from about 1 mM to about 150 mM, or about 2 mM to about 100 mM, or about 3 mM to about 75 mM, or about 4 mM to about 50 mM, or about 5 mM to about 25 mM, or about 10 mM to about 20 mM. In some embodiments, the concentration of chloride of the additive solution and/or the final concentration of chloride in the RBC composition following exchange (e.g., prior to transfusion) is less than or greater than about 500 mM, or about 250 mM, or about 200 mM, or about 150 mM, or about 100 mM, about 75 mM, or about 50 mM, or about 25 mM, or about 25 to about 250 mM, or about 40 to about 100 mM, or about 50 to about 75 mM, or about 60 to about 70 mM, or about 100 to about 200 mM, or about 125 mM to about 175 mM, or about 150 mM.

In some embodiments, the additive solution referred to herein (e.g., the additive solution administered prior to and/or following decrease of the quencher concentration) and/or the final RBC composition following exchange (e.g., prior to transfusion) comprises 10 mM to about 150 mM (or about 50 mM to about 90 mM) dextrose, 0.5 mM to about 5 mM (or about 0.75 mM to about 3 mM) adenine, about 10 mM to about 150 mM (or about 25 mM to about 100 mM) mannitol, about 10 mM to about 75 mM (or about 15 mM to about 50 mM) citrate (e.g., sodium citrate), about 3 mM to about 75 mM (or about 5 mM to about 25 mM) phosphate (e.g., $Na_2HPO_4$ and/or $NaH_2PO_4$), and about 50 to about 250 mM, or (about 100 to about 175 mM) chloride.

TABLE 2

Exemplary Additive Solutions

| | AS-1 | AS-3 | SAG-M | Eryth-rosol | AS-5 | PAGGS-M | MAP |
|---|---|---|---|---|---|---|---|
| Dextrose (mM) | 111.0 | 55.5 | 45.4 | 81.1 | 45.4 | 47.5 | 36.4 |
| Adenine (mM) | 2.0 | 2.2 | 1.3 | 1.6 | 2.2 | 1.4 | 1 |
| Guanosine (mM) | | | | | | 1.44 | |
| Mannitol (mM) | 41.2 | | 28.8 | 42.5 | 28.8 | 55 | 80 |
| Sodium Citrate Dihydrate (mM) | | 20 | | 26.6 | | | 5.1 |
| $Na_2HPO_4$ (mM) | | | | 17 | | 8 | |
| $NaH_2PO_4$ (mM) | | 20 | | 4.7 | | 8 | 6 |
| NaCl (mM) | 154.0 | 70 | 150 | | 150 | 72 | 85 |
| Citric Acid (mM) | | 2 | | | | | 1 |
| Osmolality (mOsm) | | 276 | 359 | 175 | 351 | 296 | |

Methods of Inactivation Using Diluted Red Blood Cells

The red blood cell compositions described herein may be diluted prior to inactivation. Subjecting the red blood cells to a diluent may decrease the concentration of dissolved species (e.g., salts such as Cl⁻) to a level that is suitable for the inactivation with methods described herein. Examples of diluent solutions are described herein and shown in Table 3. In some embodiments, non-packed red blood cells (e.g., red blood cells having a hematocrit in the range about 50 to 70%, or about 55 to 65%, or about 60% and optionally comprising SAG-M or Optisol) are subjected to a diluent solution (e.g., any solution described herein or in Table 3) prior to an inactivation method described herein (e.g., a method wherein the composition comprises about 20 mM GSH with about 1 equivalent base and about 0.2 mM S-303), followed by decreasing of the quencher concentration as described herein (e.g., to less than about 10 mM, or less than about 5 mM). In some of these embodiments, decreasing the quencher concentration comprises removal of the treatment solution (e.g., a diluted treatment solution) followed by the addition of a final additive solution (e.g., SAG-M, AS-5, or any solution described above or in Table 2) to provide, for example, a red blood cell composition having a hematocrit in the range about 50 to 70%, or about 55 to 65%, or about 60%). In some embodiments, the concentration of chloride ion in the red blood cell composition is diluted to less than or greater than about 150 mM, or about 120 mM, or about 100 mM, or about 90 mM, about 80 mM, or about 70 mM, or about 60 mM, or about 50 mM, about 40 mM, about 30 mM, or about 20 mM, about 10 mM, or between about 25 and 250 mM, or about 40 and 100 mM, or about 50 and 75 mM, or about 60 and 70 mM, or about 65 mM prior to inactivation. In some embodiments, the amount (by volume) of diluent solution added to the RBC solution is between about 0.2 and 2 times, or about 0.3 and 1.5 times, or about 0.4 and 1 times, or about 0.5 and 0.75 times the amount of RBC solution. In some of these embodiments, the red blood cell composition is diluted with a diluent solution (e.g., any solution described herein or in Table 3) to a hematocrit level in the range about 30 to 50%, or about 35 to 45%, or about 40%.

In some embodiments, the diluent solution referred to herein comprises one or more of the following components: dextrose, adenine, mannitol, citrate (e.g., sodium citrate), citric acid, phosphate (e.g., $Na_2HPO_4$ and/or $NaH_2PO_4$) and chloride (e.g., from sodium chloride). In some embodiments, the concentration of dextrose of the diluent solution and/or the final concentration of dextrose in the RBC composition following dilution with the diluent solution is at a concentration from about 10 mM to about 150 mM, or about 20 mM to about 120 mM, or about 25 mM to about 100 mM, or about 30 mM to about 75 mM, or about 40 mM to about 50 mM, or about 50 mM to about 60 mM. In some embodiments, the concentration of adenine of the diluent solution and/or the final concentration of adenine in the RBC composition following dilution with the diluent solution is from about 0.5 mM to about 5 mM, or about 0.75 mM to about 3 mM, or about 1 mM to about 2.5 mM. In some embodiments, the concentration of mannitol of the diluent solution and/or the final concentration of mannitol in the RBC composition following dilution is from about 10 mM to about 150 mM, or about 20 mM to about 120 mM, or about 25 mM to about 100 mM, or about 30 mM to about 75 mM, or about 40 mM to about 60 mM, or about 25 mM to about 35 mM. In some embodiments, the concentration of citrate (e.g., sodium citrate) of the diluent solution and/or the final concentration of citrate in the RBC composition following dilution with the diluent solution is from about 5 mM to about 100 mM, or about 10 mM to about 75 mM, or about 15 mM to about 50 mM, or about 15 mM to about 35 mM, or about 20 mM to about 30 mM. In some embodiments, the concentration of phosphate (e.g., $Na_2HPO_4$ and/or $NaH_2PO_4$) of the diluent solution and/or the final concentration of phosphate in the RBC composition following dilution with the diluent solution is from about 1 mM to about 150 mM, or about 2 mM to about 100 mM, or about 3 mM to about 75 mM, or about 4 mM to about 50 mM, or about 5 mM to about 25 mM, or about 10 mM to about 20 mM. In some embodiments, the concentration of chloride of the diluent solution and/or following dilution with the diluent solution is less than or greater than about 500 mM, or about 250 mM, or about 200 mM, or about 150 mM, or about 120 mM, or about 100 mM, or about 90 mM, or about 80 mM, or about 70 mM, or about 60 mM, or about 50 mM, or about 40 mM, or about 30 mM, or about 20 mM, about 10 mM or about 25 to about 250 mM, or about 40 to about 100 mM, or about 50 to about 75 mM, or about 60 to about 70 mM, or about 100 to about 200 mM, or about 125 mM to about 175 mM.

In some embodiments, the diluent solution referred to herein and/or the RBC composition following dilution with the diluent solution comprises 10 mM to about 150 mM (or about 35 mM to about 65 mM) dextrose, 0.5 mM to about 5 mM (or about 0.75 mM to about 3 mM) adenine, about 10 mM to about 150 mM (or about 25 mM to about 75 mM) mannitol, about 10 mM to about 75 mM (or about 15 mM to about 50 mM) citrate (e.g., sodium citrate), about 3 mM to about 75 mM (or about 5 mM to about 25 mM) phosphate (e.g., $Na_2HPO_4$ and/or $NaH_2PO_4$), and about 5 to about 50 mM, or (about 10 to about 25 mM) chloride.

In some embodiments, non-packed red blood cells are subjected to a diluent solution (e.g., any solution described above or in Table 3) prior to an inactivation method described herein, followed by decreasing of the quencher concentration as described herein, then treated with a final additive solution (e.g., SAG-M, AS-5, or any solution described above or in Table 2) to provide an RBC composition suitable for use (e.g., suitable of transfusion). In some embodiments, the final additive solution may be any additive solution described herein, for example, an additive solution wherein the concentration of chloride (and/or the final concentration of chloride in the RBC composition following exchange, such as prior to transfusion) is less than about 500 mM, or about 250 mM, or about 200 mM, or about 150 mM, or about 100 mM, about 75 mM, or about 50 mM, or about 25 mM, or between about 25 and 250 mM, or about 40 and 100 mM, or about 50 and 75 mM, or about 60 and 70 mM, or about 100 and 200 mM, or about 125 mM and 175 mM, or about 150 mM.

TABLE 3

Exemplary Diluent Solutions

| | DS 1 | DS 2 | DS 3 | DS 4 | DS 5 | DS 6 | DS 7 | DS 8 | DS 9 | DS 10 | DS 11 | DS 12 | DS 13 |
|---|---|---|---|---|---|---|---|---|---|---|---|---|---|
| Dextrose (mM) | 55 | 55 | 55 | 55 | 55 | 45.4 | 45.4 | 45.4 | 45.4 | 45.4 | 45.4 | 45.4 | |
| Adenine/ Adenine HCl (mM) | 1.3 | 1.3 | 1.3 | 1.3 | 1.3 | 1.3 | 1.3 | 1.3 | 1.3 | 1.3 | 1.3 | 1.3 | 1.3 |
| Mannitol (mM) | 55 | 55 | 55 | 55 | 55 | 28.8 | | | 28.8 | 28.8 | 28.8 | 28.8 | 28.8 |

TABLE 3-continued

Exemplary Diluent Solutions

| | DS 1 | DS 2 | DS 3 | DS 4 | DS 5 | DS 6 | DS 7 | DS 8 | DS 9 | DS 10 | DS 11 | DS 12 | DS 13 |
|---|---|---|---|---|---|---|---|---|---|---|---|---|---|
| Sodium Citrate dihydrate or anhydrous (mM) | 20 | 20 | | | | 33.5 | 33.5 | 33.5 | 20 | 20 | 20 | 20 | 20 |
| $Na_2HPO_4$ (mM) | | | | 20 | 15 | | | 33.5 | 12.7 | 3.5 | 16.2 | 20 | |
| $NaH_2PO_4$ (mM) | | | | | | 33.5 | 33.5 | | 3.5 | 12.7 | | | 16.2 |
| NaCl (mM) | | | | 15 | 20 | | | | | | | | |
| Osmolality (mOsm) | 180 | 178 | 128 | 177 | 179 | 287 | 243 | 215 | 227 | 179 | 174 | 181 | |
| pH | 6.9 | 7.6-8.0 | | 8.61 | 8.38 | 6.28 | 6.29 | 8.77 | 7.48 | 6.63 | 8.62 | 8.7 | 7.5 |

Methods of Inactivation Using Reconstituted Packed Red Blood Cells

In some embodiments, packed red blood cells (pRBCs) (e.g., red blood cells having a hematocrit in the range of about 70 to 90%, or about 75 to 85%, or about 80%) are subjected to a treatment solution prior to conducting the inactivation method described herein (e.g., a method wherein the composition comprises about 20 mM GSH with about 1 equivalent base and about 0.2 mM S-303). Examples of treatment solutions are shown in Table 4. In some embodiments, the treatment solution (e.g., any solution described in Table 4) is added to the pRBCs prior to the addition of the quencher, pathogen-inactivating compound, and any added base. In some of these embodiments, the pRBC composition is treated with a treatment solution resulting in non-packed red blood cells (e.g., red blood cells having a hematocrit in the range about 50 to 70%, or about 55 to 65%, or about 60%). In some embodiments, (a) a treatment solution is added to pRBCs, (b) an inactivation method described herein (e.g., a method wherein the composition comprises about 20 mM GSH with about 1 equivalent base and about 0.2 mM S-303) is conducted, and (c) the concentration of the quencher is decreased as described herein (e.g., to less than about 10 mM, or less than about 5 mM). In some of these embodiments, step (c) comprises removal of the treatment solution and addition of a final additive solution (e.g., any solution described in herein, such as SAG-M, AS-5 or any solution of Tables 2, 3, or 4) to provide, for example, a red blood cell composition having a hematocrit in the range about 50 to 70%, or about 55 to 65%, or about 60%. In some of these embodiments, the concentration of chloride ion in the red blood cell composition prior to and/or during inactivation is less than or greater than about 150 mM, or about 120 mM, or about 100 mM, or about 90 mM, about 80 mM, or about 70 mM, or about 60 mM, or about 50 mM, about 40 mM, or about 30 mM, or about 20 mM, about 10 mM, or between about 25 and 250 mM, or about 40 and 100 mM, or about 50 and 75 mM, or about 60 and 70 mM, or about 65 mM.

In some embodiments, the treatment solution referred to herein comprises one or more of the following components: dextrose, adenine, mannitol, citrate (e.g., sodium citrate), citric acid, phosphate (e.g., $Na_2HPO_4$ and/or $NaH_2PO_4$) and chloride (e.g., from sodium chloride). In some embodiments, the concentration of dextrose of the treatment solution and/or the concentration of dextrose in the additive solution following removal of the treatment solution in the RBC composition is from about 10 mM to about 150 mM, or about 20 mM to about 120 mM, or about 25 mM to about 100 mM, or about 30 mM to about 75 mM, or about 40 mM to about 50 mM, or about 50 mM to about 60 mM. In some embodiments, the concentration of adenine of the treatment solution and/or the concentration of adenine in the additive solution following removal of the treatment solution in the RBC composition is from about 0.5 mM to about 5 mM, or about 0.75 mM to about 3 mM, or about 1 mM to about 2.5 mM. In some embodiments, the concentration of mannitol in the treatment solution and/or the concentration of mannitol in the additive solution following removal of the treatment solution in the RBC composition is from about 10 mM to about 150 mM, or about 20 mM to about 120 mM, or about 25 mM to about 100 mM, or about 30 mM to about 75 mM, or about 40 mM to about 60 mM. In some embodiments, the concentration of citrate (e.g., sodium citrate) in the treatment solution and/or the concentration of citrate in the additive solution following removal of the treatment solution in the RBC composition is from about 1 mM to about 100 mM, or about 2 mM to about 75 mM, or about 5 mM to about 50 mM, or about 7.5 mM to about 25 mM, or about 10 mM to about 15 mM. In some embodiments, the concentration of phosphate (e.g., $Na_2HPO_4$ and/or $NaH_2PO_4$) in the treatment solution and/or the concentration of phosphate in the additive solution following removal of the treatment solution in the RBC composition is from about 1 mM to about 150 mM, or about 2 mM to about 100 mM, or about 3 mM to about 75 mM, or about 4 mM to about 50 mM, or about 5 mM to about 25 mM, or about 10 mM to about 20 mM. In some embodiments, the concentration of chloride in the treatment solution and/or the concentration of chloride in the additive solution following removal of the treatment solution in the RBC composition is from about 250 mM, or about 200 mM, or about 150 mM, or about 120 mM, or about 100 mM, or about 90 mM, or about 80 mM, or about 70 mM, or about 60 mM, or about 50 mM, or about 40 mM, or about 30 mM, or about 20 mM, about 10 mM, or about 25 to about 250 mM, or about 40 to about 100 mM, or about 50 to about 75 mM, or about 60 to about 70 mM, or about 100 to about 200 mM, or about 125 mM to about 175 mM.

In some embodiments, the treatment solution and/or the additive solution following removal of the treatment solution in the RBC composition comprises 10 mM to about 150 mM (or about 35 mM to about 65 mM) dextrose, 0.5 mM to about 5 mM (or about 0.75 mM to about 3 mM) adenine, about 10 mM to about 150 mM (or about 25 mM to about 75 mM) mannitol, about 5 mM to about 75 mM (or about 10 mM to about 20 mM) citrate (e.g., sodium citrate), about 3 mM to about 75 mM (or about 5 mM to about 25 mM) phosphate (e.g., Na$_2$HPO$_4$ and/or NaH$_2$PO$_4$), and about 5 to about 100 mM, or (about 25 to about 75 mM) chloride.

TABLE 4

Exemplary Treatment Solutions

|  | Sol 1 | Sol 2 | Sol 3 | Sol 4 | Sol 5 |
|---|---|---|---|---|---|
| Dextrose (mM) | 45.4 | 45.4 | 45.4 | 45.4 | 45.4 |
| Adenine/Adenine HCl (mM) | 1.3 | 1.3 | 1.3 | 1.3 | 1.3 |
| Mannitol (mM) | 55 | 44.5 | 44.5 | 44.5 | 30 |
| Sodium Citrate dihydrate or anhydrous (mM) |  | 12 | 12 | 12 |  |
| Na$_2$HPO$_4$ (mM) |  |  |  |  | 15 |
| NaH$_2$PO$_4$ (mM) |  |  |  |  |  |
| NaCl (mM) | 70 | 60 | 60 | 60 | 70 |
| Osmolality (mOsm) |  |  |  |  |  |
| pH (adjusted with citric acid) |  |  | 7 | 6.5 | 6.5 |

Evaluating Method Efficacy

In addition to comparing the log inactivation as discussed above, the efficacy of the improved quenching methods may be evaluated by several other methods, as described in US Patent Publication No. 2006/0115466, the content of which is hereby incorporated by reference in its entirety. For example, the quenching methods may be assessed by evaluating the modification of the red blood cell composition, in terms of the function, morphology and the hydration status of the red blood cells, and in terms of the reactivity of the treated red blood cells with the immune system, such as with antibodies. If the treated red blood cell composition is intended for human use, such as infusion, the quenching methods should not substantially damage red blood cell function (e.g., via dehydration). The lack of a substantially damaging effect on red blood cell function may be measured by methods known in the art for testing red blood cell function. In particular, levels of dehydration can be measured, for example, by hematocrit (packed cell volume, PCV), osmotic fragility, mean corpuscular hemoglobin concentration (MCHC), percent hemolysis, and ektacytometry. The levels of other indicators of function, such as total ATP (adenosine 5'-triphosphate), total 2,3-DPG (2,3-diphosphoglycerol) or extracellular potassium may be measured, and compared to an untreated control. Additionally, intracellular and extracellular pH, hemoglobin, glucose consumption and lactate production may be measured. The improved methods of the present invention can be compared to the previously described conditions of treatment in US Patent Publication No. 2006/0115466 (e.g., fully quenched (2 base equivalent) 20 mM glutathione in combination with the S-303/red blood cell mixture without reduction in quencher concentration following incubation described therein).

In some embodiments of the present invention, the red blood cells of the methods and compositions described herein have minimal or no damage following treatment (e.g., dehydration, hemolysis, etc.). In some embodiments, the red blood cells of the resulting mixture comprising the red blood cell composition, quencher, pathogen-inactivating compound and any added base (before or after the reduction in the quencher concentration) have less than 4%, or less than 3%, or less than 2%, less than 1% hemolysis, or less than 0.5% hemolysis. In some embodiments, the red blood cells of the resulting mixture have less than 4%, or less than 3%, or less than 2%, or less than 1%, or less than 0.5% hemolysis at a time of about 10 days at 4° C., or about 28 or 42 days at 4° C., or about 42 days at 4° C. following the reduction in concentration of the quencher (e.g., glutathione).

In some embodiments, the red blood cells of the resulting mixture comprising the red blood cell composition, quencher, pathogen-inactivating compound and any added base (before or after the reduction in the quencher concentration) have greater than 50%, or greater than 55%, or greater than 60%, or greater than 65% packed cell volume (PCV). In some embodiments, the red blood cells of the resulting mixture have greater than 50%, or greater than 55%, or greater than 60%, or greater than 65% packed cell volume (PCV) at a time of about 10 days at 4° C., or about 28 or 42 days at 4° C., or about 42 days at 4° C. following the reduction in concentration of the quencher (e.g., glutathione).

In some embodiments, the red blood cells of the resulting mixture comprising the red blood cell composition, quencher, pathogen-inactivating compound and any added base (before or after the reduction in the quencher concentration) have a Median Corpuscular Fragility (MCF; osmolarity at which 50% of hemolysis occurs) greater than 130, or greater than 135, or greater than 140, or greater than 145, or greater than 150, or greater than 155. In some embodiments, the red blood cells of the resulting mixture have a Median Corpuscular Fragility (MCF) greater than 130, or greater than 135, greater than 140, or greater than 145, or greater than 150, or greater than 155 at a time of about 10 days at 4° C., or about 28 or 42 days at 4° C., or about 42 days at 4° C. following the reduction in concentration of the quencher (e.g., glutathione).

Methods for determining ATP, 2,3-DPG, glucose, hemoglobin, hemolysis, and potassium are available in the art and described herein in the experimental section. See for example, Davey et al., *Transfusion*, 32:525-528 (1992), the disclosure of which is incorporated herein. Methods for determining red blood cell function are also described in Greenwalt et al., *Vox Sang*, 58:94-99 (1990); Hogman et al., *Vox Sang*, 65:271-278 (1993); and Beutler et al., *Blood*, Vol. 59 (1982) the disclosures of which are incorporated herein by reference. For example, total ATP and total 2,3-DPG may be measured using a SIGMA® ATP kit or 2,3-DPG kit (SIGMA®, St. Louis, Mo.). The ATP kit may be used following SIGMA® procedure No. 366-UV, the disclosure of which is hereby incorporated by reference. Total ATP may also be measured using a luciferase based enzymatic assay or a protocol described by Beutler (1984). Extracellular potassium levels may be measured using a CIBA CORNING™ Model 614 K$^+$/Na$^+$ Analyzer (CIBA CORNING DIAGNOSTICS CORP.™, Medford, Mass.). The extracellular pH may be measured by centrifuging the cells at 4° C. for 15 minutes at 12,000×g and removing the supernatant, for which the pH may be measured using a standard pH meter at room temperature (e.g. BECKMAN®, Epoxy Calomel electrode). For the intracellular pH, the remaining pellet may be capped in the centrifuge tube and stored at about −80° C. for at least 2 hours. This then may be lysed by the addition of deionized water. The lysed sample may be mixed well and the pH of the solution may be measured either at room temperature using a standard pH meter or at room temperature using a CIBA CORNING™ Model 238 Blood Gas Analyzer (CIBA CORNING DIAGNOSTICS CORP.™, Medford, Mass.). Measurements can be made shortly after treatment and as a function of post-treatment storage, for example storage for up to 42 days. The methods of the present invention provide a red blood cell composition wherein hemolysis of the treated red blood cells is less than 3% after 28 day storage, more preferably less than 2% after 42 day storage, and most preferably less than or equal to about 1% after 42 day storage at 4° C. In some embodiments are provided a red blood cell composition (e.g., a red blood cell composition using any of the methods described herein) wherein the total ATP level may be higher when compared to a red blood cell composition treated using 2 mM acidic glutathione and 0.2 mM S-303. In some embodiments, the quenching methods described herein provide red blood cell compositions having ATP levels that are about 20%, also 30%, also 40% or about 50% higher when compared to compositions from methods using 2 mM acidic glutathione and 0.2 mM S-303. In some embodiments, the higher level of ATP is maintained after 7, 14, 21, 28, 35, or 42 days of storage. In some embodiments, the higher level of ATP decreases during storage.

In some embodiments of the present invention, the methods and compositions described herein include red blood cell compositions wherein the red blood cells have a reduced number of unwanted side reactions from the pathogen-inactivating compound (e.g., binding of the pathogen-inactivating compound to the RBC surface). In some embodiments, the side reaction is modification of the surface of the red blood cells by the pathogen-inactivating compound. The reduction in modification of red blood cells in the methods of the present invention can be evaluated by several assays known in the art, such as those described in U.S. Patent Publication No. 2006/0115466, the content of which is hereby incorporated by reference. Quantification of acridine bound to the RBC surface can also be determined using a sensitive fluorescence-activated immune flow cytometric assay (IFC) described herein.

With respect to the fluorescence detection assays, the quenching methods of the present invention, when compared with the same treatment without the use of base (e.g., methods using neutralizing glutathione compared to the same methods using non-neutralized glutathione), may result in reduction of the median fluorescence by at least 10%, also at least 25%, also at least 50%, also at least 75%, or at least 90%. For example, the quenching methods of the present invention using any of the compositions described with the use of base (e.g., a red blood cell composition comprising about 15-25 mM glutathione, about 0.5 to 1.5 equivalent of base, and about 0.2 mM S-303) may result in a lower level of median fluorescence when compared to an identical composition, but without the use of base (e.g., a red blood cell composition comprising about 15-25 mM glutathione and about 0.2 mM S-303 without base).

The level of pathogen-inactivating compound bound to the RBC surface for the quenching methods and compositions of the present inventions also can be measured in terms of Antibody Binding Capacity (ABC; the number of molecules of pathogen-inactivating compound or derivative thereof per red cell, as determined by the use of calibration beads from BANGS LABORATORIES, INC.™; Fishers, Ind.; see Examples 5 and 9) which involves a mouse monoclonal anti-acridine antibody conjugated to allophycocyanin (APC) and a FACS-Caliber flow cytometer (BD™ BIOSCIENCES). In some embodiments of any of the methods and compositions of the present invention, the RBCs have an average ABC value of less than about 75,000, or less than about 70,000, or less than about 60,000, or less than about 55,000, or less than about 52,500, or less than about 50,000, or less than about 47,500, or less than about 45,000, or less than about 42,500, or less than about 40,000, or less than about 37,500, or less than about 35,000, or less than about 32,500, or less than about 30,000, or less than about 27,500, or less than about 25,000. In some embodiments, the RBCs have an average ABC value of between about 10,000 and 80,000, or between about 20,000 and 70,000, or between about 25,000 and 70,000, or between about 25,000 and 60,000, or between about 30,000 and 50,000, or between about 35,000 and 45,000. In some embodiment of the methods described herein, when compared with such similar treatment with quencher and base (e.g., neutralized glutathione), may result in an ABC value of less than 90%, also less than 75%, also less than 65%, also less than 55%, also less than 45%, also less than 35%, also less than 25%, or less than 10% as compared to the identical methods using a RBC composition that is not treated with base (e.g., glutathione that is not neutralized).

The quenching methods of the invention can also be compared to existing methods by determining the level of modification of nucleic acids in a sample. Typically, a red blood cell composition may contain leukocytes, and the nucleic acid from the leukocytes can be isolated. A pathogen-inactivating compound having a radioactive isotope that, upon reaction of the compound with nucleic acid, will remain bound to the nucleic acid. This can be used to assess the amount of compound reacted with the nucleic acid for a variety of quenching methods, and provides a measure that can be directly correlated to expected leukocyte inactivation. The number of S-303 adducts formed per 1,000 nucleic acid base pairs can be used as a model to assess the expected impact of the various methods on pathogen inactivation. Alternatively, a suitable amount of a pathogen can be added to a red blood cell composition and the nucleic acid of the pathogen can be isolated after treatment. However, in this case the sample needs to be leukoreduced such that the levels of any residual leukocytes will not interfere with the measurement of pathogen nucleic acid.

In addition to providing adequate pathogen inactivation while reducing the levels of unwanted side reactions (e.g., binding of the pathogen-inactivating compound to the RBC surface which may lead to an undesired immune response) and dehydration, the quenching methods of the present invention also provide, in at least some embodiments, a reduction in the concentration of reactive electrophilic species after pathogen inactivation. If the red blood cell compositions are intended for infusion, it is important that the level of reactive electrophilic species is as low as possible, preferably essentially no longer detectable. The presence of the reactive electrophilic species may be determined using methods available in the art, such as chromatographic methods including liquid chromatography-mass spectroscopy (LC-MS-MS). In addition, the residual activity of a sample may be assessed by evaluating its ability to react with a guanine residue of a nucleic acid, such as using the general alkylator assay described by Mattes (Mattes, W R, Anal. Biochem. 1992 October; 206(1):161-7). In this assay, the RBCs are extracted after a suitable incubation time with the pathogen-inactivating compound and quencher. Any residual pathogen-inactivating compound, as well as the quencher and other small species, are separated from the proteins. These species are then incubated with double-stranded (ds) DNA synthesized with 8-$^3$H guanine residues. The residual pathogen-inactivating compound reacts with ds DNA at the N7 position of guanine, which acidifies the 8-H reside and releases the $^3$H into solution, where it can be isolated and measured. The amount of tritium released can be quantified, and has a 1:1 correlation with the amount of residual alkylator present in the extracted samples tested. The level of electrophilic species as determined by these methods can be assessed using the improved methods of the invention and comparing to known methods.

In some embodiments of each of the methods described herein, the method further comprises the step of reducing the concentration of a compound in the mixture, wherein the compound is selected from the group consisting of the pathogen-inactivating compound and a degradation product of the pathogen-inactivating compound. In some embodiments, the method comprises the step of reducing the concentration of the pathogen-inactivating compound in the mixture. In some embodiments, the method comprises the step of reducing the concentration of the electrophilic species in the mixture. The concentration of the pathogen-inactivating compound in a biological material, such as a blood product, can be reduced after the treatment, for example by adsorption in a batch or flow removal process. Methods and devices which may be used are described in U.S. Pat. Nos. 6,544,727; 6,331,387; 6,951,713; and 7,037,642; and U.S. Patent Applications 2002/0192632 (abandoned) and 2001/0009756 (abandoned), the disclosures of each of which are incorporated herein by reference in their entirety. Accordingly, in some embodiments, the concentration of the pathogen-inactivating compound is reduced by contacting the mixture with an adsorption medium comprising adsorbent particles having an affinity for the pathogen-inactivating compound. In some embodiments, the adsorption system would be configured to remove the pathogen-inactivating compound in a batch process. In some embodiments, the pathogen inactivation compound is not reduced by using a compound adsorption device. In some embodiments, the concentration of the pathogen-inactivating compound in the mixture is reduced by washing the red blood cells using techniques known in the art. In some embodiments, the concentration of the pathogen-inactivating compound in the mixture is reduced by removing some or all of the treatment solution (e.g., SAG-M, AS-5, or any solution described in Tables 2, 3, and/or 4) by methods described herein and/or known in the art (e.g., using centrifuges and expression devices or combined centrifuge and expressors such as TACSI® made by TERUMO®). In some embodiments, the concentration of the pathogen-inactivating compound in the mixture is reduced by removing some or all of the treatment solution (e.g., SAG-M, AS-5, or any solution described in Tables 2, 3, and/or 4), followed by addition of an additive solution (e.g., SAG-M, AS-5, or any solution described in Table 2) to the mixture. In some embodiments, the concentration of the pathogen-inactivating compound is reduced simultaneously with a reduction in the concentration of the quencher.

Treated Blood Compositions

In some embodiments, the invention also provides red blood cell compositions resulting from each of the treatment methods described herein. In some embodiments, the invention also provides red blood cell compositions preparable by each of the treatment methods described herein. In one aspect, the invention provides a composition comprising a) red blood cells, wherein the red blood cells have covalently reacted with an electrophilic group of a pathogen-inactivating compound; and b) a quencher comprising a thiol group that is capable of reacting with the pathogen-inactivating compound; wherein the composition is suitable for infusion into humans after storage of 28 or 42 days at 4° C.

In some embodiments of each of the methods and compositions described herein, the red blood cells in the red blood cell composition are mammalian blood cells. For instance, the red blood cells may be rodent (e.g., mouse or rat), canine, lagomorph (e.g., rabbit), non-human primate (e.g., chimpanzee), or human red blood cells. For example, in some embodiments, the red blood cells are human. In some embodiments, the red blood cells have been leukoreduced. In some other embodiments, the red blood cells have not been leukoreduced. In some embodiments, there is a possibility that the composition comprising red blood cells is contaminated with a pathogen. In some embodiments, the red blood cell composition is contaminated with a pathogen. In some embodiments, at least 1 log, or at least 2 logs, or at least 3 logs, or at least 4 logs of pathogen in the composition is inactivated, if present.

In some embodiments, the invention embraces red blood cell compositions wherein the red blood cells have been modified with a pathogen-inactivating compound (e.g., S-303), as described herein. In some embodiments, the red blood cell compositions produced by the treatment of the methods comprise degradation products of the pathogen inactivating compound (e.g., the reaction product of the quencher with the pathogen inactivating compound). In some embodiments, the modification is reaction of the electrophilic group of a pathogen-inactivating compound with the red blood cell surface. In some embodiments, the pathogen-inactivating compound is covalently bound to the red blood cell surface. In some embodiments, the pathogen-inactivating compound is covalently bound to one or more proteins on the red blood cell surface. In some embodiments, the modification is a nucleophilic group of the red blood cell reacted with the electrophilic group of the pathogen-inactivating compound, wherein the electrophilic group is a mustard group and the nucleophilic group has replaced one or more of the chlorine atoms of the mustard group. In some embodiments, the pathogen-inactivating compound is non-covalently bound to the red blood cell surface. In some embodiments the RBC compositions have an average ABC value of less than 75,000, or less than 70,000, or less than 60,000, or less than 55,000, or less than 52,500, or less than 50,000, or less than 47,500, or less than 45,000, or less than 42,500, or less than 40,000, or less than 37,500, or less than 35,000, or less than 32,500, or less than 30,000, or less than 27,500, or less than 25,000. In some embodiments, the RBCs have an average ABC value of between about 10,000 and 80,000, or between about 20,000 and 70,000, or between about 25,000 and 70,000, or between about 25,000 and 60,000, or between about 30,000 and 50,000, or between about 35,000 and 45,000.

In some embodiments, the red blood cell compositions comprise reduced levels of modification of the surface of the red blood cells by the pathogen inactivating compound, relative to red blood cells produced by other methods involving treatment with the pathogen inactivating compound. In some embodiments, the red blood cell compositions produced by the treatments of the methods described herein comprise a reduced amount of pathogen inactivating compound comprising the reactive electrophilic group after completion of the treatment, relative to a red blood cells composition produced by another method involving treatment with the pathogen inactivating compound (e.g., a method without sufficient quencher and/or base added to the reaction mixture, a method in which no quencher and/or base is added to the reaction mixture, and/or a treatment at a lower pH). In some embodiments, the amount of pathogen inactivating compound comprising the reactive electrophilic group in the composition has been reduced by about 10%, about 25%, about 50%, about 75%, about 90%, about 95%, or about 99%, relative to a composition treated by another method involving the pathogen inactivating compound (e.g., a method without sufficient quencher and/or base added to the reaction mixture, a method in which no quencher and/or base is added to the reaction mixture, and/or treatment at a lower pH).

In some of these embodiments, the red blood cell composition comprises residual quencher compound (e.g., glutathione). In some embodiments, the composition comprises a concentration of quencher sufficiently low to maintain RBC vitality and lifespan and avoid red blood cell dehydration and/or reduced osmotic fragility during storage. In some embodiments, the composition comprises a concentration of quencher that is sufficiently lower than a concentration of quencher previously used in the composition. In some embodiments, the higher concentration of quencher previously used decreases RBC vitality and lifespan and/or increases red blood cell dehydration and decreases osmotic fragility during storage, while the lower concentration is sufficiently lower than a concentration of quencher previously used in the composition. In some embodiments, the concentration of the quencher in the composition is less than about 25 mM, less than about 20 mM, less than about 15 mM, less than about 10 mM, less than about 8 mM, less than about 6 mM, less than about 5 mM, less than about 4 mM, less than about 3 mM, less than about 2 mM, or than about 1 mM. In some embodiments, the concentration of the quencher in the composition is in the range of about 1 mM to 20 mM, about 2 mM to 15 mM, about 3 mM to 10 mM, about 4 mM to 8 mM, or about 5 mM to 6 mM.

In some embodiments, the composition comprises an additive solution (e.g., a solution described in Table 2, or a solution comprising any combination of the components described in Table 2). In some embodiments, the composition comprises sodium chloride, adenine, glucose, phosphate, and/or mannitol. In some embodiments, the final concentration of chloride ion in the RBC composition (e.g., prior to transfusion) is less than about 500 mM, or about 250 mM, or about 200 mM, or about 150 mM, or about 100 mM, about 75 mM, or about 50 mM, or about 25 mM, or between about 25 and 250 mM, or about 40 and 100 mM, or about 50 and 75 mM, or about 60 and 70 mM, or about 100 and 200 mM, or about 125 mM and 175 mM, or about 150 mM.

In some embodiments, the composition is suitable for infusion into an individual (e.g., a human) after about 2 days, or about 5 days, or about 10 days, or about 15 days, or about 20 days, or about 28 days, or about 35 days, or about 42 days of storage at 4° C.

In some of these embodiments, the composition comprises a) red blood cells that are covalently reacted with an electrophilic group of a pathogen-inactivating compound (e.g., S-303) on the cell surface and i) have a packed cell volume (PCV) of greater than 60%, and/or ii) have an average antibody binding capacity (ABC) of between about 25,000 and 70,000 (or about 35,000 and 45,000) and b) a glutathione quencher at a concentration of less than about 8 mM (or less than 6 mM, or less than about 2 mM). In some embodiments, at least 3 log (or at least 1 log) of a pathogen is inactivated, if present. In some embodiments, the composition is suitable for infusion into humans up to 28 or 42 days of storage at 4° C.

Kits

In addition to the improved methods of quenching, the present invention provides disposable kits for the processing of a red blood cell composition, where the processing may be done manually or automatically. In some embodiments, the present invention provides kits comprising the pathogen-inactivating compound, quencher, and/or base used in the each of the methods described herein. In some embodiments, the kit provides fresh solution (such as buffer for resuspension of the cells) for use following decreasing of the quencher concentration described herein.

In some embodiments, the kit comprises S-303, including any salts thereof and neutralized glutathione, including any salts thereof. S-303 may be in solid form or in solution. Similarly, the neutralized glutathione may be in solid form or in solution. These solids or solutions may further comprise acceptable excipients, adjuvants, diluents, or stabilizers. In some embodiments, S-303 is the hydrochloride salt and the neutralized glutathione is neutralized with about 1 equivalent of sodium hydroxide. In some embodiments, S-303 and neutralized glutathione are in solid form and the kit further comprises a suitable solution for dissolving the S-303 and a suitable solution for dissolving the neutralized glutathione. In some embodiments, the invention provides a kit comprising a pathogen-inactivating compound, a quencher and a solution for dissolving the quencher, wherein the solution neutralizes or partially neutralizes the quencher. The methods and kits discussed herein encompass any suitable pharmaceutical formulation of the pathogen-inactivating compound and quencher, which can be formulated as a mixture or separately. Pharmaceutically acceptable formulations are known to those skilled in the art, and examples of suitable excipients, adjuvants, diluents or stabilizers can be found, for example, in Gennaro, ed., Remington's The Science and Practice of Pharmacy, $20^{th}$ edition, Lippincott Williams & Wilkins. The invention also includes the resulting compositions of the methods described above, comprising red blood cells, a pathogen-inactivating compound and quencher as described above, wherein the composition is in a suitable pH range to effect improved quenching of the pathogen-inactivating compound.

In another aspect, the invention provides a kit useful, e.g., for treating red blood cell compositions to inactivate pathogens, comprising a pathogen-inactivating compound comprising a nucleic acid binding ligand and a functional group which is, or which forms, an electrophilic group (including any salt thereof) a quencher comprising a thiol group (including any salt thereof), and about 0.75 to about 1.25 equivalent base, wherein an equivalent means a molar amount that is equivalent to the molar amount of quencher in the kit. In some embodiments, the kit comprises about 1 equivalents of a suitable base.

In still another aspect, the invention provides a kit for treating red blood cell compositions to inactivate pathogens, comprising a nucleic acid binding ligand and a functional group which is, or which forms, an electrophilic group (e.g., S-303), including any salt thereof, a neutralized quencher comprising a thiol group (e.g., neutralized glutathione), including any salt thereof, and optionally fresh solution (such as buffer for resuspension of the cells) for use following decreasing of the quencher concentration described herein. In some embodiments, the solution is an additive solution, diluent solution, and/or a treatment solution described herein (e.g., SAG-M, AS-5, or any solution described above or in Table 2, 3, and/or 4).

Examples, Materials, & Methods

The invention is further illustrated by the following non-limiting examples.

Example 1

Organism Preparation

Examples, Materials, & Methods

Bacterial and viral strains used for these studies were clinical isolates obtained from either the California Department of Health Services or the American Type Culture Collection.

Bacteria: Frozen working stocks of bacteria were inoculated into a 500 mL flask containing a mixture of 50% yeast extract media without added glucose and 50% fetal bovine serum. The flasks were incubated overnight in a shaking waterbath set at 37° C. Gram positive bacteria were spiked into the blood product directly from the overnight culture. The overnight cultures of Gram negative bacteria were further subcultured by a 1:1000 dilution into fresh culture medium and incubated as above until they reach log phase as determined by optical density. This log phase growth was spiked into the blood product for PI experiments.

Viruses: Cell free viral stocks were prepared using the appropriate cell lines for each virus. These stocks were frozen at −80° C. until they were thawed and spiked directly into the blood product for PI experiments.

Example 2

Preparation of RBC Units

Blood was received at Cerus as 450 mL or 500 mL units of whole blood either on the day of collection or up to 3 days after collection. In most cases the whole blood was leukofiltered before being processed into RBC units. Occasional units could not be successfully leukofiltered (e.g., blood from donors with sickle trait) and these units were used without leukofiltration for PI studies of organisms that are not known to survive inside white blood cells.

After leukofiltration, the blood was centrifuged and the plasma was expressed. The desired RBC additive solution, such as AS-3 (NUTRICEL®), was then added and the resulting RBC unit was either used immediately or stored at 4° C. until use.

Example 3

Pathogen Inactivation (PI)

The PI process involves inoculation of RBC units with a culture of the organism to be tested. The typical target input titer of organisms in the RBC units was approximately $10^6$ cfu or pfu/mL of RBC. In most cases the organism volume (including any culture medium) was approximately 1% of the RBC unit volume and was not typically greater than 10%. To evaluate inactivation of lower, more physiologically relevant, levels of bacteria, inputs from 10 to $10^5$ cfu/unit were used. For low level input studies two RBC units were pooled, spiked, then split into a Test unit that was treated as described herein and a Control unit to which only quencher (e.g., GSH) was added (no pathogen inactivator, e.g., S-303) and which was kept under the same temperature conditions as the Test unit.

After addition of the organism into the RBC unit, the unit was mixed by grasping the ends of the container and moving the ends 10 times in a figure eight, or bicycle pedal, motion.

The contaminated RBCs were then transferred to the mixing container of the RBC PI process disposable set. The set consists of a series of plastic containers and ports connected by plastic tubing. The mixing container was a dual-port 600-mL capacity PL1813 plastic container. Connected to each of the ports was a Y-tubing set with Luer-adapted pediatric filters attached to one lead. The unused lead on one port connects to another 600-mL capacity PL1813 plastic container (Incubation Container). The remaining unused lead was the line used to connect the original RBC unit.

The dosing solutions were prepared and added to the units as follows: A 600 mM Glutathione (GSH) solution with 1 equivalent of NaOH was prepared by dissolving 2.8 g of GSH in ~12 mL of 0.9% saline and 0.9 mL of 10 N NaOH. The appropriate volume of GSH solution was drawn into a 20 mL capacity syringe. The volume used was typically 10 mL of GSH solution per 280 mL of RBC, plus 2 mL line loss to generate 20 mM GSH in the dosed RBC unit. The syringe containing GSH was attached to the mixing container using the filtered lead that shares a Y fitting with the lead connected to the incubation container. The unit was placed on a rocker to facilitate top to bottom mixing during addition of dosing solutions. The GSH was added to the unit while the unit is mixing on the rocker. The unit was then mixed manually using the figure eight mixing method described above. After addition of GSH the units were allowed to rest at room temperature for 5 minutes.

After the rest period, a small sample of RBCs were removed and cultured to determine the pre-treatment titer. Standard plate assays were used for bacterial samples and cell culture assays were used for viruses.

A 6 mM amustaline hydrochloride (S-303) solution was prepared by dissolving 46 mg S-303 in ~15 mL of 0.9% saline. The appropriate dose of S-303 solution was drawn into a 20 mL syringe. The volume used was typically 10 mL of S-303 solution per 280 mL of RBC, plus 2 mL line loss to generate 0.2 mM S-303 in the dosed RBC unit. The unit was then mixed manually using the figure eight mixing method as described above. The treated RBC unit was incubated at room temperature for a minimum of 3 hours after addition of S-303 to ensure completion of pathogen inactivation prior to sampling for post-treatment titer.

At 3 hours post-PI, samples were removed and cultured, as described above, to determine post-treatment titer. For studies evaluating inactivation of low-level bacterial input, both the Test and Control units were incubated at RT for ~20 hours post-treatment and then incubated at 37° C. overnight. Following 37° C. incubation, samples were removed from each treated Test unit and from the identical untreated Control unit and cultured to obtain a qualitative assessment of bacterial titer. The untreated Control unit exhibited growth.

Log reduction for each unit was determined by taking the log of the ratio of pre-treatment titer to post-treatment titer, where titers were expressed as 10× cfu or pfu/mL.

Example 4

RBC In Vitro Function Experiments

Human RBC units were prepared in additive solutions, such as AS-3 (NUTRICEL®), according the manufacturer's instructions. RBC units were treated with various concentrations of GSH to achieve final concentrations ranging from 2 mM to 30 mM. In some cases the GSH was pH adjusted with 1 or 2 base equivalents with either sodium bicarbonate or sodium hydroxide prior to treatment. Following treatment with GSH the RBC were treated with S-303, dissolved with 0.9% sodium chloride, to achieve a concentration of 0.2 mM S-303 in the RBC, or mock dosed with 0.9% sodium chloride. After treatment, units were incubated for 20 h at 20-25° C. Post incubation some units were centrifuged at 6 min, 21° C., 4100×g, supernatant expressed and 100 mL of fresh additive solution was added to the RBC. All units were placed at 4° C. for storage. Untreated controls were placed at 4° C. after being prepared in additive solution.

In vitro function was assayed at various time points throughout the course of storage. Extracellular pH at 37° C. was determined by measuring the pH of RBC from each unit in a CHIRON® DIAGNOSTICS Blood Gas analyzer. Total ATP was measured using a luciferase based enzymatic assay or a protocol described by Beutler (1984). Cell free supernatants were prepared to evaluate extracellular potassium, glucose, and lactate. Extracellular Potassium was determined by measuring the $K^+$ content of cell free supernatant using a CHIRON® DIAGNOSTICS Na/K analyzer (model #614) or similar analyzer. Extracellular glucose and lactate were evaluated on a NEXCT™ analyzer. Red cell indices were collected using the ADVIA® hematology analyzer (SIEMENS®).

RBCs were washed thrice in 0.9% sodium chloride and incubated a minimum of 1 h at RT prior to analysis for osmotic fragility and density profiles. The method used for osmotic fragility is outlined by Beutler et al., 1982, (Blood Journal 59:1141-1147) and was modified for a 96-well format (Lew et al., 2003, Blood 101:4189-4194). Density distribution curves were obtained according to Danon and Marikovsky, 1964 (J Lab Clin Med 6:668-674), using phthalate esters in microhematocrit tubes.

Example 5

Quantification of Pathogen-Inactivating Compound Binding to RBC Surface

The level of acridine bound to the RBC surface was detected with a sensitive fluorescence-activated immune flow cytometric assay (IFC) using a mouse anti-acridine monoclonal antibody conjugated to allophycocyanin (APC) and a FACS-Caliber flow cytometer (BD™ BIOSCIENCES). Briefly, RBCs were washed thrice in 0.9% saline and resuspended to a 4% hematocrit in flow incubation buffer (HBSS, 1% BSA, 0.1% $NaN_3$, 1 mM EDTA, 3% BSA). Next, mouse monoclonal anti-acridine antibody conjugated to APC was added and incubated for 30 minutes at 4° C.; cells were washed in flow wash buffer (HBSS 1% BSA, 0.1% $NaN_3$, 1 mM EDTA) resuspended in the same buffer and a total of 30,000 events were evaluated in the FACS-Caliber at an appropriate gating. Quantification of numbers of S-303 molecules bound to the cell surface of human RBC (ABC) was performed using QUANTUM SIMPLY CELLULAR™ bead kits (BANG LABORATORIES, INC.™; Fishers, Ind.).

Example 6

Glutathione pH Effects on Immediate and Storage-Related RBC Hydration and Function RBC units were treated with S-303 (0.2 mM) and GSH (20 mM) pH-adjusted with NaOH (varying base equivalents (b.e.)) to potentiate GSH quenching. The pH of tested dosing solutions was 2.9, 4.5, and 8.9 for 0 b.e., 1 b.e., and 2 b.e., respectively. Following treatment, RBCs were stored at 4° C. and assayed periodically for extracellular pH, glucose, lactate, potassium, total ATP and hemolysis. RBC physical parameters (MCV, MCH, MCHC, HDW etc) were measured by optical flow cytometry, osmotic fragility measurements were performed as per Beutler et al., (1982) with modification by Lew et al., (2003).

Figure 2:
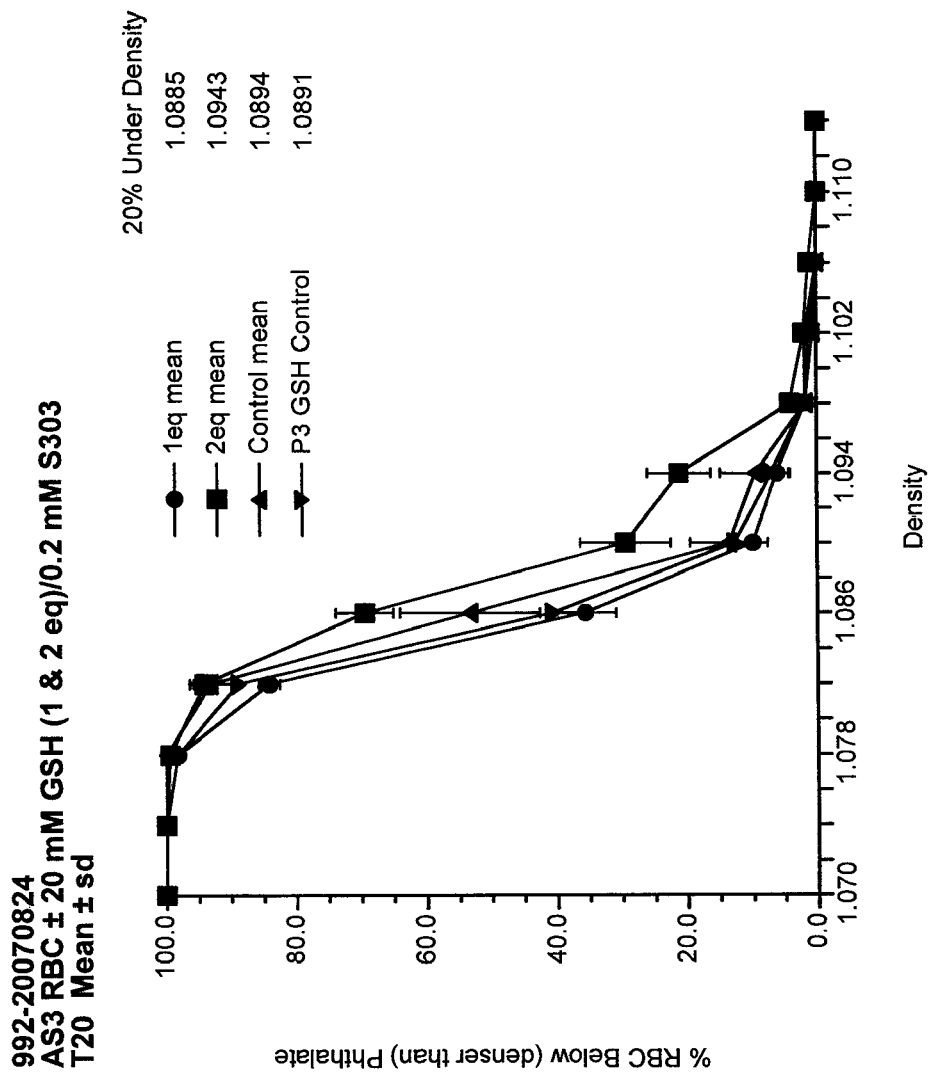
FIG. 2 shows the red blood cell density at various levels of base at 20 hours of incubation.

Exposure of RBC to alkaline GSH resulted in decreased Hct with immediate and sustained decreased osmotic fragility and increased RBC density (e.g., see FIG. 1). This immediate dehydration was corrected by decreasing the base equivalents, resulting in a lower pH of the GSH solutions (see Table 5). Although immediate dehydration was ameliorated, osmotic fragility of RBCs continued to be changed (Table 6; further Examples in FIGS. 2 and 3) by the presence of GSH in a concentration dependent way. Measurement of MCHC and the distribution of MCH using optical flow cytometry (ADVIA® hematology analyzer, SIEMENS®) correlated with changes in osmotic fragility and density. The dehydration was S-303 independent as the effect was also demonstrated by pH and GSH in the absence of S-303.

TABLE 5

Effect of sodium hydroxide base adjusted levels of GSH on RBC hydration immediately post-treatment

| Base Level | MCF* (mOsm) | Hct (%) | MCHC (g/dL) | Blood pH |
|---|---|---|---|---|
| Untreated | 160 | 62 | 31 | 6.743 |
| Mock dosed | Not Done | 56 | 33 | 6.759 |
| Dosed (0 b.e.) | 173 | 59 | 31 | 6.206 |
| Dosed (1 b.e.) | 156 | 52 | 36 | 6.713 |
| Dosed (2 b.e.) | 142 | 47 | 42 | 7.180 |

*MCF (Median Corpuscular Fragility) = osmolarity at which 50% of hemolysis occurs

TABLE 6

Effect of GSH base equivalents on RBC hydration and function during storage

| Time** | Base Level | MCF* (mOsm) | Hct (%) | MCHC (g/dL) | Blood pH | ATP (µmoles/gHb) | Glucose (mM) | Lactate (mM) |
|---|---|---|---|---|---|---|---|---|
| 20 hr | Untreated | 158 | 61 ± 1 | 30 ± 1 | 6.749 ± 0.011 | 5.35 ± 0.41 | 11.6 ± 0.1 | 0.9 ± 0.7 |
| | Dosed (1 b.e.) | 156 | 52 ± 1 | 32 ± 1 | 6.644 ± 0.034 | 6.45 ± 0.37 | 14.5 ± 0.7 | 0.2 ± 0.0 |
| | Dosed (2 b.e.) | 145 | 46 ± 1 | 35 ± 1 | 7.173 ± 0.020 | 8.17 ± 0.50 | 12.8 ± 0.3 | 0.1 ± 0.1 |
| 14 Days | Untreated | 158 | 60 ± 1 | 31 ± 0 | 6.617 ± 0.020 | 4.78 ± 0.62 | 9.8 ± 1.3 | 3.7 ± 0.3 |
| | Dosed (1 b.e.) | 152 | 51 ± 1 | 34 ± 1 | 6.486 ± 0.019 | 4.47 ± 0.70 | 9.4 ± 0.4 | 2.4 ± 0.6 |
| | Dosed (2 b.e.) | 146 | 47 ± 1 | 36 ± 1 | 6.651 ± 0.035 | 5.58 ± 0.36 | 6.2 ± 0.9 | 5.7 ± 0.5 |
| 35 Days | Untreated | 159 | 61 ± 3 | 31 ± 1 | 6.477 ± 0.039 | 3.52 ± 0.37 | 11.6 ± 0.3 | 10.6 ± 2.0 |
| | Dosed (1 b.e.) | 148 | 52 ± 1 | 34 ± 1 | 6.423 ± 0.033 | 2.77 ± 0.49 | 14.5 ± 0.9 | 20.6 ± 1.6 |
| | Dosed (2 b.e.) | 147 | 49 ± 1 | 35 ± 1 | 6.489 ± 0.030 | 3.937 ± 0.51 | 12.8 ± 0.5 | 10.1 ± 1.0 |

*MCF (Median Corpuscular Fragility) = osmolarity at which 50% of hemolysis occurs
**Days post-dosing. Blood dosed at 5 days old.

RBC hydration changes correlated with GSH, pH and concentration, but did not correlate with S-303 or biochemical assays (ATP, lactate, glucose) routinely used to assess RBC function. Limiting exposure to high pH of GSH prevented the initial dehydration effect. Limiting continued exposure of high levels of GSH prevented the storage dehydration effect. These studies show that assessment of the hydration status of stored RBCs should be included as a predictor of RBC quality as substantial changes in hydration had no effect on conventional criteria but may have contributed to the moderate change in red cell life span.

Example 7

Improved Quenching Method with Subsequent Decrease in Quencher Results in Decreased RBC Dehydration Following Storage RBC units were treated with S-303 (0.2 mM) and GSH (20 mM) pH-adjusted with 1 equivalent NaOH to potentiate GSH quenching. Following treatment with GSH the RBC were treated with S-303, dissolved with 0.9% sodium chloride, to achieve a concentration of 0.2 mM S-303 in the RBC, or mock dosed with 0.9% sodium chloride. After treatment, units were incubated for 20 h at 20-25° C. Post incubation some units were centrifuged at 6 min, 21° C., 4100×g, supernatant expressed and 100 mL of fresh additive solution was added to the RBC. All units were placed at 4° C. for storage. Untreated controls were placed at 4° C. after being prepared in additive solution. RBC osmotic fragility measurements were performed as per Beutler et al., (1982) with modification per Lew et al., (2003).

Figure 3:
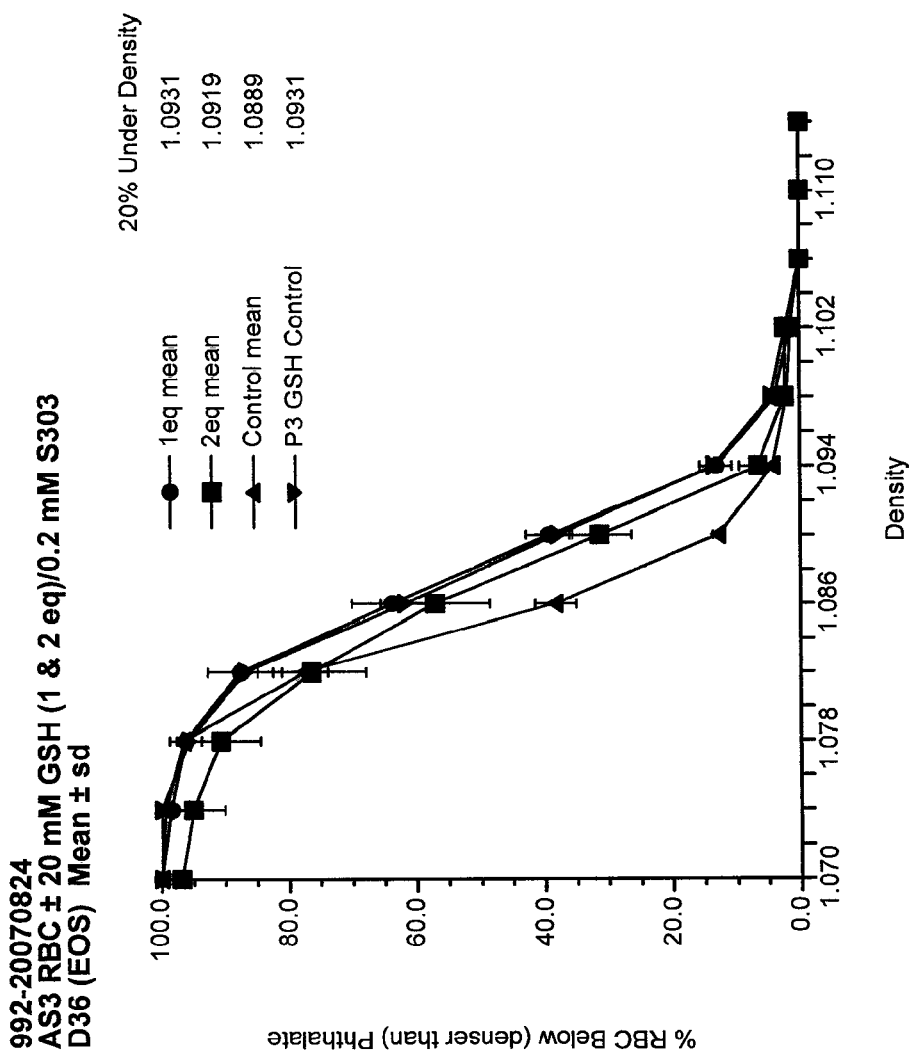
FIG. 3 shows the red blood cell density at various levels of base after incubation and 36 days of storage.
Figure 4:
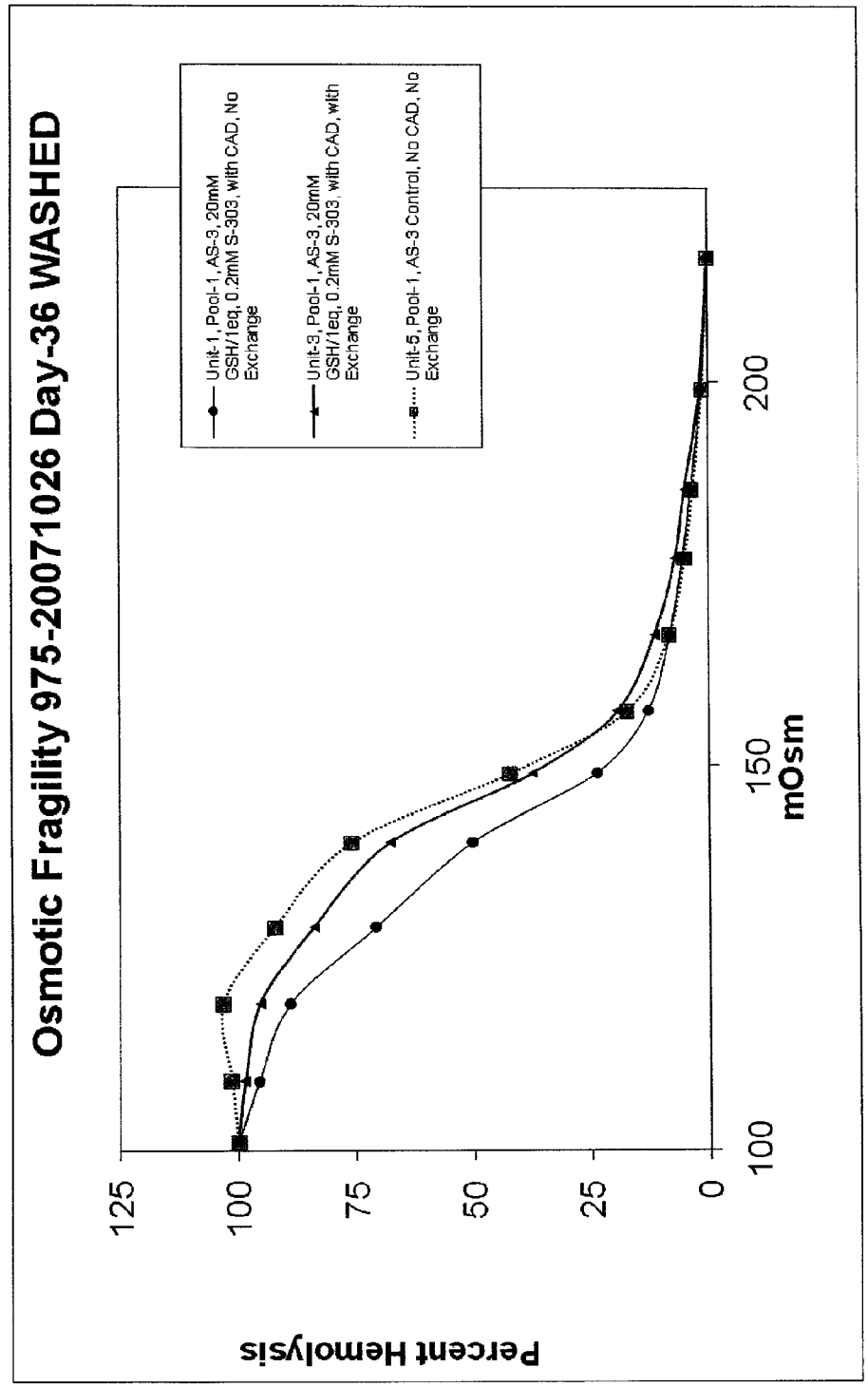
FIG. 4 shows the osmotic fragility of red blood cells after incubation and 36 days of storage with and without decreasing the quencher concentration (i.e. with/without exchange step).
Figure 5:
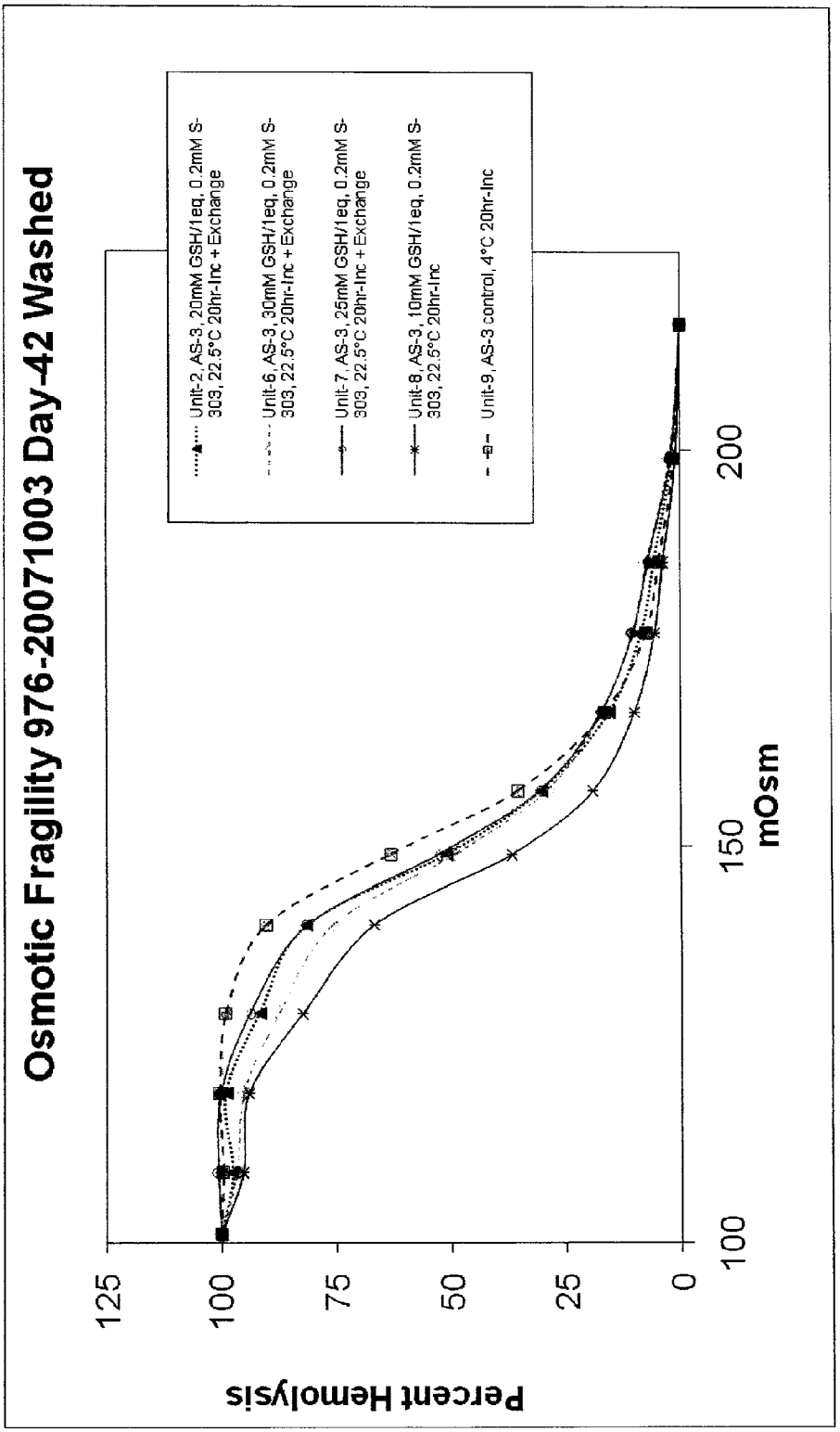
FIG. 5 shows the osmotic fragility of red blood cells after incubation and 42 days of storage with varying initial quencher concentration (with exchange step) compared to moderate initial quencher concentration (without exchange step).
Figure 6:
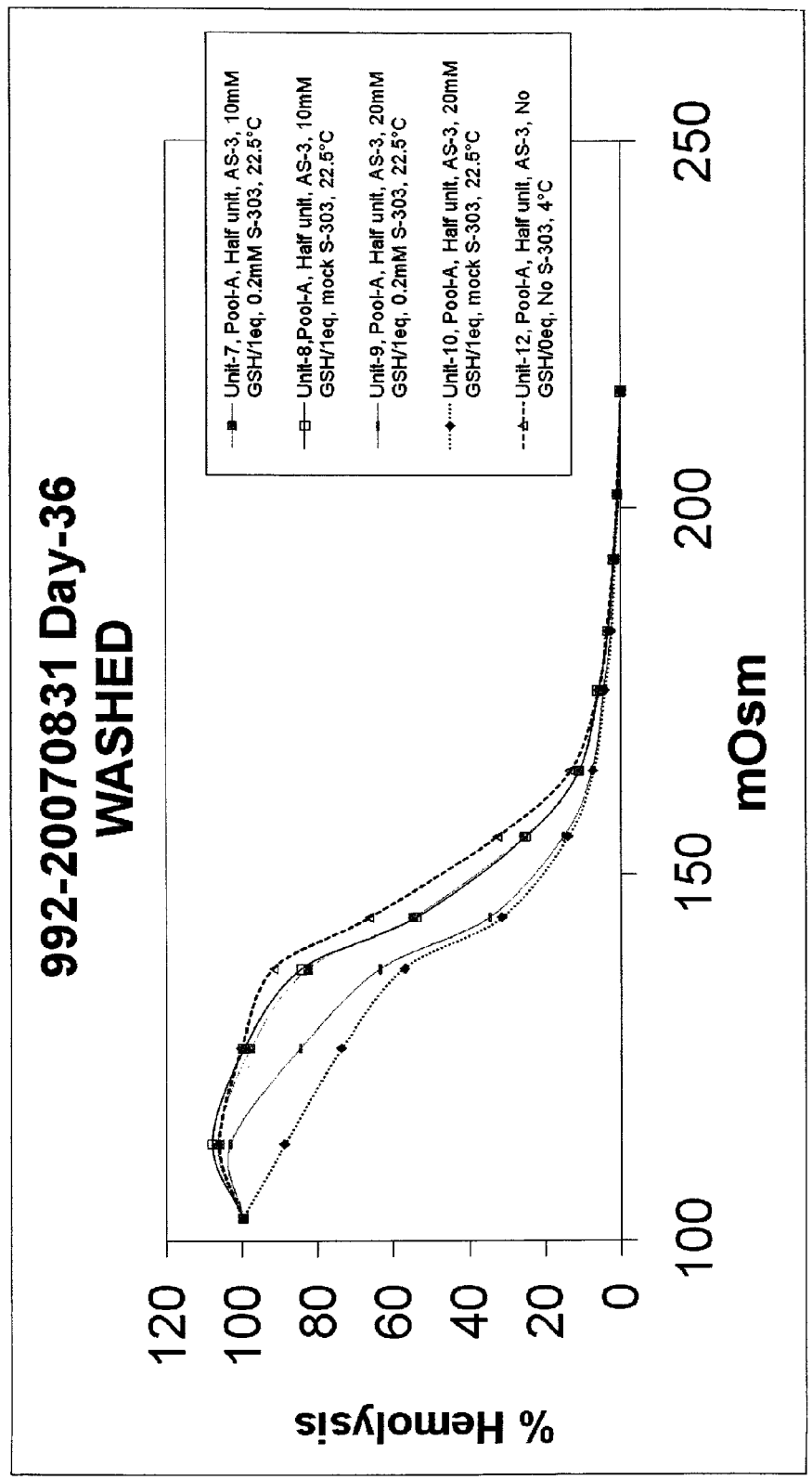
FIG. 6 shows the osmotic fragility of red blood cells after incubation and 36 days of storage with and without pathogen-inactivating compound.

Prolonged exposure of RBC to high concentrations of GSH resulted in increased RBC density and decreased osmotic fragility (e.g., see Table 5, FIGS. 3 and 4). This storage-related dehydration was corrected by removing the GSH prior to RBC storage (e.g., see FIGS. 4 and 5). The time and GSH concentration dependent dehydration was S-303 independent as the effect was also demonstrated by GSH in the absence of S-303 (e.g., see FIG. 6).

RBC hydration changes correlated with GSH. Limiting exposure to high concentrations of GSH by exchanging the treatment solution for fresh additive solution prevented the storage induced dehydration effect.

Example 8

Pathogen Inactivation for Improved Quenching Methods

Leukoreduced RBC units with a hematocrit of approximately 60% were prepared in AS-3 storage medium. RBC units were inoculated with approximately 6 logs/mL of viable organism, and an aliquot was removed to serve as the untreated, input control. GSH in a solution of 1 equivalent NaOH was added to the inoculated units to a final concentration of 20 mM and mixed well. S-303 was added to a final concentration of 0.2 mM and the units were again mixed well and incubated at 20 to 25° C. for three hours. Following incubation, samples were removed and assayed to detect residual viable organisms. Control samples were titered immediately after preparation and again after the 3-hour incubation period. At least two replicates were performed for each organism.

With the exception of *Pseudomonas*, the Gram negative, Gram positive and one example virus were effectively inactivated by treatment with GSH neutralized with 1 equivalent of NaOH compared to neutralization with 2 equivalents of NaOH (see Table 7).

Pathogen inactivation of *Pseudomonas aeruginosa* using a total inoculation titer of up to 4.4 logs per RBC unit resulted in complete inactivation.

TABLE 7

Pathogen inactivation data for improved quenching conditions vs. previous conditions.

| | Log Reduction GSH (20 mM), 1 b.e. | Log Reduction GSH (20 mM), 2 b.e. |
|---|---|---|
| *S. aureus* | 6.0 ± 0.3 (n = 4) | 6.4 |
| *S. marcescens* | 3.7 ± 0.4 (n = 3) | 4.8 |
| *Y. enterocolitica* | 5.0 ± 0.4 (n = 4) | 4.6 |
| *E. coli* | 5.9 ± 0.8 (n = 4) | 6.5 |
| *P. aeruginosa*\* | 1.2 ± 0.4 (n = 3) | 1.8 |
| VSV | >5.9 | 4.2 |

Example 9

Surface-Bound Acridine Levels for Improved Quenching Methods with Exchange Step

Figure 7:
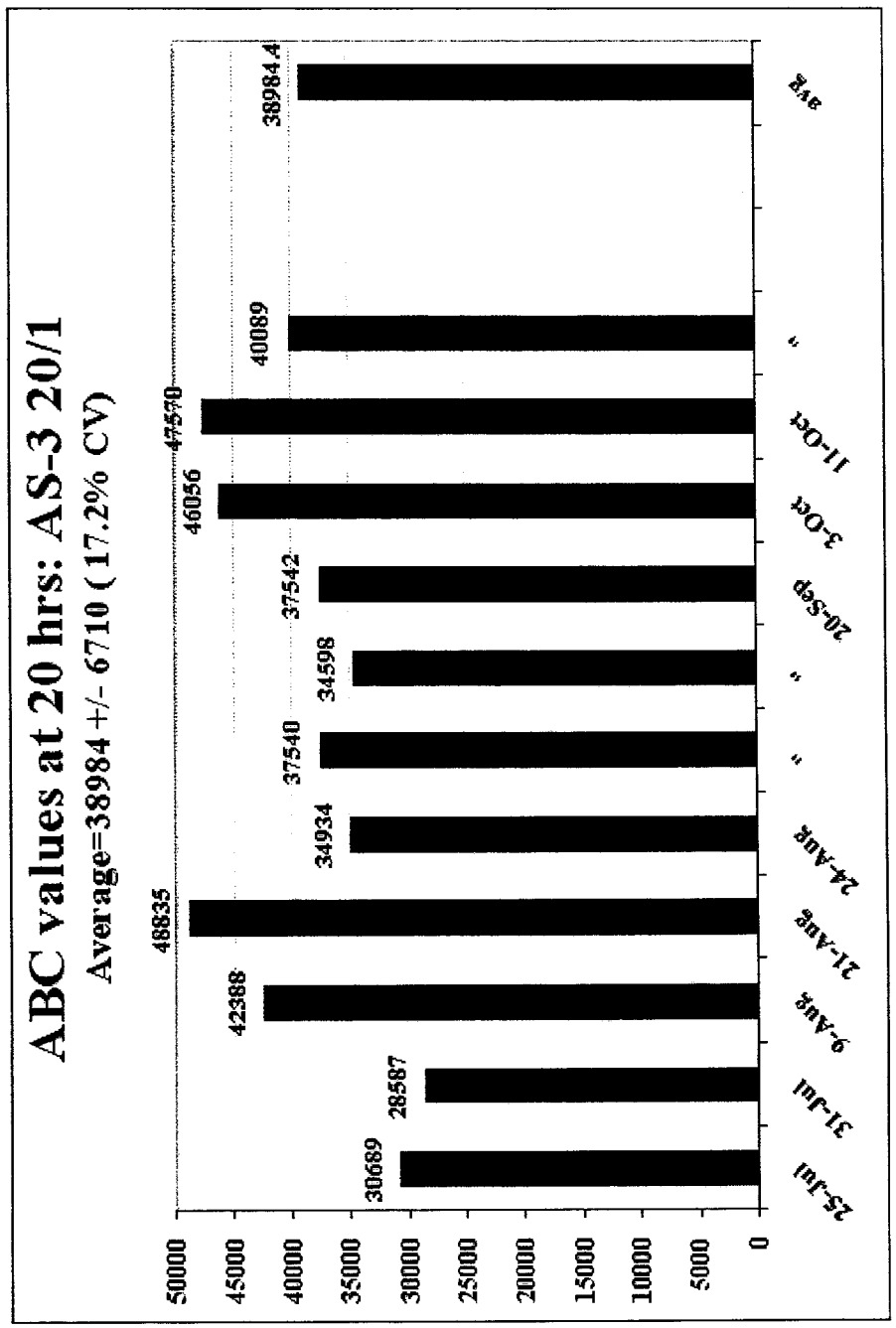
FIG. 7 shows the antibody binding capacity (ABC) values for several red blood cell preparations using the methods of the present invention.

The method described in Example 5 was used to determine the anti-acridine antibody binding capacity to red blood cells treated with 20 mM GSH neutralized with 1 equivalent of NaOH and 0.2 mM S-303. The antibody binding capacity measured across several RBC preparations was approximately 39,000 per red cell (see FIG. 7). This level of binding compares to 18,407±1195 ABC when RBC are treated with 20 mM GSH neutralized with 2 equivalents of NaOH and 123,714±5123 ABC when RBC are treated with 2 mM acidic GSH.

Example 10

Pathogen Inactivation with S-303 Treatment at Variable Hematocrit (Hct)

RBC units, from 450 to 500 mL WB collections, were prepared without additive solution (80% spun hematocrit (Hct)) or in additive solution (60% Hct). The RBC were leukofiltered before treatment unless otherwise indicated. Test units at 40% Hct were diluted with a diluent solution. RBC units were inoculated with either a high level input of ~$10^6$ organisms/mL or a low level input from 10 to $10^5$ organisms per unit. For the high level input, a control sample of 28 mL was removed prior to S-303 treatment. For the low level bacterial input, Test and Control units were prepared by pooling and splitting full RBC units and the Control unit was inoculated with ~10 organisms per unit. Test units with 80% and 60% Hct were treated with 200 µM S-303 and 20 mM GSH, neutralized with one base equivalent of sodium hydroxide (1 b.e.). Test units with 40% Hct were treated with 130 µM S-303 and 13 mM GSH (1 b.e.). The Control samples or units were treated with either 20 mM GSH or 13 mM GSH (1 b.e.) based on Hct. For units with high level input, Control samples were assayed for viable organisms at the time the Test unit was treated. After 3 hours of incubation at RT both the Test units and Control samples were assayed for viable organisms, which were quantified by growth on rich agar plates (bacteria) or by plaque assay on Vero cells (VSV). For units with low level input, the Control and Test units were incubated at RT for 20 hours and then at 37° C. for ~20 hours. Samples were then plated to detect bacterial growth. Results are shown Table 8.

TABLE 8

Pathogen inactivation data for samples of varying hematocrit values.

| Organism | 80% Hematocrit | 60% Hematocrit | 40% Hematocrit |
|---|---|---|---|
| High Level Input | Mean Log$_{10}$ Reduction$^a$ (N = 2) | | |
| Yersinia enterocolitica | 3.4$^b$ | 4.9 | 6.1 |
| Escherichia coli | 3.8$^b$ | 6.1$^c$ | 6.6 |
| Serratia marcescens | 4.4$^b$ | 4.5 | 3.1 |
| Staphylococcus aureus | ≥5.8$^b$ | 6.7 | >7 |
| Vesticular stomatitis virus (VSV) | >6.2$^b$ | >5.9 | 5.9 |
| Low Level Input | Full Unit Inactivation$^d$ (log$_{10}$) | | |
| Pseudomonas aerugenosa | ≥2.7 | ≥2.5 | ≥2.5 |

$^a$Log reduction is calculated as Log (Untreated titer/Post-treatment titer), with titer expressed as 10$^x$/mL
$^b$Pathogen reduction without leukofiltration
$^c$n = 3
$^d$In all cases, control units at the lowest input level were positive for bacterial growth Example 11

RBC Hydration Following S-303 Treatment at Varying Hematocrit (Hct)

RBCs were prepared from leukoreduced whole blood at 40% or 60% Hct, measured by spun hematocrit, in additive solution and at 80% Hct as packed red cells. Units were treated with GSH (sodium salt, BioMedica Foscama, Italy) and S-303 at a final concentration of 20 mM and 0.2 mM respectively. All treated units were incubated up to 20 hours at RT. The treatment solution was replaced with SAG-M and units were adjusted to 60% Hct for storage at 4° C. Control RBC units were prepared in SAG-M and stored at 4° C. All units were assayed periodically for physical parameters; MCHC was measured manually, osmotic fragility measurements were performed by standard methods (Beutler et al., and Lew et al., 2003). Median corpuscular fragility (MCF) was defined as the NaCl concentration at which 50% of RBCs were hemolysed. Change in MCF is an index of surface to volume ratio (SN) and hydration of RBC during storage. After approximately 6 weeks of storage all treated units had MCF values comparable to untreated controls, regardless of Hct at time of treatment. MCHC, another index of RBC hydration, was similar between Test and Control units at the end of storage. Results are shown in Table 9. Storage of treated RBC for up to 6 weeks did not significantly alter the RBC hydration and SN over a wide range of Hct used in routine practice for preparation of RBC concentrates.

TABLE 9

Hydration data for samples of varying hematocrit values.

| | MCF (mOsm) (n = 2) | | MCHC (g/dL) (n = 2) | |
|---|---|---|---|---|
| | 20 h post dosing | Post storage | 20 h post dosing | Post storage |
| 40% HCT | 156 | 152 | 33 | 31 |
| 80% HCT | 158 | 156 | 32 | 30 |
| SAG-M Control | 156 | 158 | 32 | 30 |
| 60% HCT | 151 | 148 | 33 | 33 |
| SAG-M Control | 150 | 154 | 32 | 32 |

Example 12

In Vitro Quality of Stored RBCs Following S-303 Treatment at Variable Hematocrit (Hct)

RBCs were prepared from leukoreduced whole blood at 40% or 60% Hct, measured by spun hematocrit, in additive solution and at 80% Hct as packed red cells. Units were treated with GSH (sodium salt) and S-303 at a final concentration of 20 mM and 0.2 mM respectively. All treated units were incubated up to 20 hours at RT. The treatment solution was replaced with SAG-M and units were adjusted to 60% Hct for storage at 4° C. Control RBC units were prepared in SAG-M and stored at 4° C. In vitro function was assayed pre- and post-treatment and at regular intervals for up to 6 weeks storage. Parameters assessed for in vitro RBC function included pH, total ATP, hemolysis, and extracellular potassium, glucose and lactate. After approximately 6 weeks (Day 38 to Day 44) of storage, all Test units had total ATP levels greater than 2 μmol ATP/g Hb and the hemolysis and MCHC were comparable to Control units, regardless of treatment Hct. Throughout storage the Test unit extracellular glucose was higher than that of Control units for 40% and 60% Hct, whereas units with 80% Hct were more similar to Control. Extracellular lactate was lower in all Test units, regardless of Hct, compared to Control. At the end of storage, extracellular K$^+$ was slightly lower in Test units than Control for 40% and 60% Hct units whereas the 80% Hct units were comparable to Control. The pH of all Test units was similar to Control throughout storage. Hemoglobin yield from the process, regardless of treatment Hct, met AABB requirements. The activity of all metabolic parameters was similar to Control after S-303 treatment over a wide range of Hct throughout 6 weeks of storage. Results are shown in Table 10.

TABLE 10

Metabolic parameters for pathogen inactivation of RBC at varying hematocrit values.

| | ATP (μmol/gHb) (n = 2) | % Hemolysis (n = 2) | MCHC (g/dL) (n = 2) | Glucose (mmo/L) (n = 2) |
|---|---|---|---|---|
| Test 40% HCT | 3.28 (D38) | 0.2% (D44) | 31 (D44) | 11.8 (D44) |
| Test 80% HCT | 3.42 (D38) | 0.3% (D44) | 30 (D44) | 7.7 (D44) |
| SAG-M Control | 3.35 (D38) | 0.3% (D44) | 30 (D44) | 6.3 (D44) |
| Test 60% HCT | 2.96 (D42) | 0.2% (D42) | 30 (D42) | 9.1 (D42) |
| SAG-M Control | 3.19 (D42) | 0.3% (D42) | 30 (D42) | 5.1 (D42) |

Example 13

In Vitro Function and Pathogen Inactivation of Diluted RBCs

SAG-M RBC units were prepared from leukoreduced whole blood units from 500 mL collections. For RBC function studies, SAG-M RBC units were pooled by ABO type, and split for matched Test and Control units. Prior to treatment, 150 mL of diluent solution comprising 28.8 mM mannitol, 1.3 mM adenine, 16.2 mM sodium phosphate, 20 mM sodium citrate, pH 7.5 was added to Test units. Test units were treated with a GSH sodium salt and S-303 at a final concentration of 20 mM and 0.2 mM respectively. Test units were incubated up to 20 hours at room temperature (RT). After RT incubation, units were centrifuged and the supernatant was exchanged with 100 mL of SAG-M which was added prior to storage at 4° C. Control RBC units were prepared in SAG-M and stored at 4° C. All units were evaluated over approximately 6 weeks of storage at 4° C. by sampling at various timepoints. For RBC pathogen inactivation studies, the SAG-M RBC units were split in half and the RBC units were inoculated with pathogens prior to the addition of the treatment solution and GSH. After addition of the treatment solution and GSH, a control sample (5 mL to 7 mL) was removed from the unit to determine input pathogen titer and the remaining unit was treated with S-303. Treated units were sampled for residual viable pathogen titer after a 3 hour static incubation at ambient temperature.

In vitro metabolic and physical indices were evaluated at various time points throughout storage with in vitro assays. Extracellular pH at 37° C. was measured in a SIEMENS® DIAGNOSTICS Blood Gas analyzer. Total ATP was measured using a luciferase-based enzymatic assay. Cell-free supernatants were prepared to evaluate extracellular potassium ($K^+$), glucose, and lactate. Extracellular potassium was determined by measuring the $K^+$ content of cell-free supernatant using a EASYLYTE® Na/K analyzer. Extracellular glucose and lactate were evaluated on a NEXCT™ analyzer. Mean corpuscular hemoglobin concentration (MCHC) and spun hematocrit were measured manually. Osmotic fragility measurements were performed by standard methods (Beutler et al., and Lew et al., 2003). Median corpuscular fragility (MCF) was defined as the NaCl concentration at which 50% of RBCs were hemolysed.

For bacterial inactivation studies, RBC were inoculated with approximately 6.5 log cfu/mL *E. coli*, *S. marcescens*, *S. aureus*, *Y. enterocolitica*, or *P. aeruginosa*. For viral inactivation studies, RBC were inoculated with approximately 4.1 log pfu/mL to 6.4 log pfu/mL, depending on the virus. GSH dissolved in saline was added to the unit to a final concentration of 20 mM. Bacterial titers were determined by enumeration of colony-forming units (cfu) on agar plates and viral titers were determined by enumeration of plaque-forming units (pfu) on appropriate cell lines. Untreated samples were serially-diluted before enumeration. Treated samples were not diluted prior to enumeration of titers.

The results shown in the Tables 11 and 12 below demonstrate acceptable RBC metabolic function and physiological parameters over the course of the storage duration and acceptable pathogen inactivation.

TABLE 11

Hydration and metabolic parameters for pathogen inactivation of diluted RBC units.

| Days Post Donation | Treatment | MCF (mOsm) | Hct (%) | MCHC (g/dL) | Blood pH | ATP (µmol/gHb) | Glucose (mM) | Lactate (mM) |
|---|---|---|---|---|---|---|---|---|
| 1 | Untreated | ND | 54 ± 2 | 32 ± 0 | 6.982 ± 0.015 | 4.50 ± 0.87 | 34.2 ± 1.3 | 3.6 ± 0.2 |
| 1.8 | Untreated | 153 ± 3 | 54 ± 3 | 33 ± 1 | 6.944 ± 0.015 | 4.39 ± 0.41 | 33.1 ± 1.9 | 4.8 ± 0.1 |
|  | Treated | 152 ± 2 | 57 ± 1 | 32 ± 1 | 6.837 ± 0.016 | 7.05 ± 0.91 | 29.4 ± 1.1 | 3.9 ± 0.2 |
| 7-8 | Untreated | 154 ± 2 | 54 ± 3 | 32 ± 1 | 6.823 ± 0.021 | 4.87 ± 0.45 | 30.4 ± 1.0 | 10.3 ± 0.6 |
|  | Treated | 150 ± 2 | 56 ± 1 | 32 ± 1 | 6.701 ± 0.024 | 6.23 ± 0.69 | 26.3 ± 1.1 | 7.9 ± 0.5 |
| 21-23 | Untreated | 153 ± 3 | 55 ± 3 | 31 ± 1 | 6.623 ± 0.022 | 4.30 ± 0.83 | 24.5 ± 1.8 | 18.5 ± 1.4 |
|  | Treated | 148 ± 2 | 56 ± 1 | 32 ± 1 | 6.526 ± 0.028 | 4.53 ± 0.99 | 22.2 ± 0.6 | 14.1 ± 1.3 |
| 35 | Untreated | 155 ± 2 | 54 ± 3 | 32 ± 1 | 6.532 ± 0.014 | 3.31 ± 0.28 | 21.6 ± 1.3 | 25.2 ± 0.7 |
|  | Treated | 152 ± 2 | 55 ± 1 | 33 ± 1 | 6.429 ± 0.016 | 3.90 ± 0.49 | 19.7 ± 0.6 | 18.9 ± 1.1 |

N = 4

TABLE 12

Pathogen inactivation data for samples of diluted RBC units.

| Bacteria | Average Log Kill (n = 4) |
|---|---|
| *S. marcescens* | 4.20 |
| *E. coli* | =6.69 |
| *S. aureus* | 4.15 |
| *Y. enterocolitica* | =6.57 |
| *P. aeruginosa* | 3.35 |

What is claimed is:

1. A method of treating a red blood cell composition comprising:
   (a) mixing
       (i) an effective amount of a pathogen-inactivating compound comprising a functional group which is, or which forms, a reactive electrophilic group;
       (ii) an effective amount of a quencher comprising a thiol group, wherein the thiol is capable of reacting with the reactive electrophilic group of the pathogen-inactivating compound;
       (iii) a composition comprising red blood cells; and
       (iv) about 0.5 to 1.5 equivalents of base, wherein an equivalent means a molar amount that is equivalent to the molar amount of quencher in the mixture;
       in a treatment solution or diluent solution;
       wherein the treatment solution or diluent solution comprises one or more of dextrose, adenine, mannitol, citrate, and citric acid; and
       wherein the mixture of step (a) after addition of the treatment solution or diluent solution comprises between about 40 mM and 100 mM chloride ion;
   (b) replacing the solution used during treatment of the red blood cell composition in step (a) with a final additive solution, such that the concentration of the quencher in the mixture is decreased to less than about 10 mM, wherein the level of dehydration of the treated red blood cell composition is decreased relative to the level of dehydration of a red blood cell composition treated according to a method comprising step (a), but excluding step (b) and/or with 2.0 or greater equivalents of base.

2. The method of claim 1, wherein the base is of sufficient amount to reduce the level of an unwanted reaction of the pathogen-inactivating compound with red blood cells in the mixture, relative to the mixture without the base.

3. The method of claim 1, wherein the treatment solution comprises one or more of phosphate and chloride.

4. The method of claim 1, wherein the diluent solution comprises phosphate.

5. The method of claim 1, wherein the composition comprising red blood cells (iii) further comprises an additive solution.

6. The method of claim 2, wherein the unwanted reaction of the pathogen-inactivating compound with red blood cells is modification of the red blood cells by the pathogen-inactivating compound.

7. The method of claim 1, wherein the base and the quencher are mixed with the red blood cell composition prior to, at the same time, or no more than about 30 minutes after mixing the pathogen-inactivating compound with the red blood cell composition.

8. The method of claim 1, wherein the base and the quencher are mixed together prior to mixing either the base or the quencher with the red blood cell composition.

9. The method of claim 1, wherein the base is NaOH.

10. The method of claim 1 wherein the base comprises about 0.75 to 1.25 equivalents of base, wherein an equivalent means a molar amount that is equivalent to the molar amount of quencher in step (a) of the mixture.

11. The method of claim 1, wherein the base comprises about 1 equivalent of base, wherein an equivalent means a molar amount that is equivalent to the molar amount of quencher in step (a) of the mixture.

12. The method of claim 1, wherein the resulting mixture of step (a) has a pH at 37° C. of about 6.5 to 7.1.

13. The method of claim 1, wherein the quencher comprises cysteine or a derivative of cysteine.

14. The method of claim 1, wherein the quencher is glutathione or a pharmaceutically acceptable salt thereof.

15. The method of claim 1, wherein the quencher is glutathione monosodium salt.

16. The method of claim 1, wherein the concentration of the quencher in the resulting mixture of step (a) is greater than 2 mM.

17. The method of claim 1, wherein the quencher in the resulting mixture of step (a) is at a concentration of about 5 mM to about 30 mM.

18. The method of claim 1, wherein the quencher in the resulting mixture of step (a) is at a concentration of about 15 mM to about 25 mM.

19. The method of claim 1, wherein the quencher in the resulting mixture of step (a) is at a concentration of about 20 mM.

20. The method of claim 1, wherein replacing the solution used during treatment of the red blood cell composition in step (a) with a final additive solution comprises centrifugation of the mixture followed by removal of the supernatant of the mixture.

21. The method of claim 1, wherein replacing the solution used during treatment of the red blood cell composition in step (a) with a final additive solution comprises size-exclusion separation.

22. The method of claim 1, wherein replacing the solution used during treatment of the red blood cell composition in step (a) with a final additive solution comprises use of expression devices.

23. The method of claim 1, wherein the quencher in the resulting mixture of step (b) is at a concentration of less than about 8 mM.

24. The method of claim 1, wherein the quencher in the resulting mixture of step (b) is at a concentration of less than about 6 mM.

25. The method of claim 1, wherein the functional group is selected from the group consisting of a mustard, a mustard intermediate, and a mustard equivalent.

26. The method of claim 1, wherein the functional group is, or is capable of forming, an aziridinium ion.

27. The method of claim 1, wherein the reactive electrophilic group is capable of reacting with nucleic acids.

28. The method of claim 1, wherein the pathogen-inactivating compound further comprises a nucleic acid binding ligand.

29. The method of claim 28, wherein the nucleic acid binding ligand is an intercalator.

30. The method of claim 29, wherein the intercalator is an acridine.

31. The method claim 28, wherein the pathogen-inactivating compound comprises a frangible linker linking the functional group and the nucleic acid binding ligand.

32. The method of claim 1, wherein the pathogen-inactivating compound is

β-alanine, N-(acridin-9-yl), 2-[bis(2-chloroethyl)amino] ethyl ester.

33. The method of claim 1, wherein the concentration of the pathogen-inactivating compound in the resulting mixture of step (a) is about 0.1 µM to about 5 mM.

34. The method of claim 1, wherein the concentration of the pathogen-inactivating compound in the resulting mixture of step (a) is sufficient to inactivate at least 3 logs of a pathogen in the red blood cell composition, if present.

35. The method of claim 1, wherein the time between step (a) and step (b) is about 1 to 48 hours.

36. The method of claim 1, wherein the time between step (a) and step (b) is about 4 to 30 hours.

37. The method of claim 1, wherein the treatment inactivates at least 3 logs of a pathogen contaminant in the red blood cell composition, if present.

38. The method of claim 1, further comprising the step of decreasing the concentration of the pathogen-inactivating compound in the mixture.

39. The method of claim 38, wherein the steps of decreasing the concentration of the quencher in the mixture and decreasing the concentration of the pathogen-inactivating compound in the mixture occur at the same time.

40. The method of claim 1, wherein the final additive solution comprises one or more of dextrose, sodium chloride, adenine, guanosine, glucose, citrate, citric acid, phosphate, and mannitol.

41. The method of claim 1, wherein following step (a), the red blood cells of the resulting mixture have an anti-pathogen inactivating compound antibody binding capacity (ABC) of less than 55% compared to the ABC value of red blood cells from the same method under the same conditions, but without the base.

42. The method of claim 1, wherein at 20 hours following step (a), the red blood cells of the resulting mixture have an anti-pathogen inactivating compound antibody binding capacity (ABC) of less than 65% compared to the ABC value of red blood cells from the same method under the same conditions, but without the use of base.

43. The method of claim 1, wherein the red blood cells of the resulting mixture have an average anti-pathogen inactivating compound antibody binding capacity (ABC) of less than about 50,000.

44. The method of claim 1, wherein the red blood cells of the resulting mixture have an average anti-pathogen inactivating compound antibody binding capacity (ABC) of less than about 40,000.

45. The method of claim 1, wherein the red blood cells of the resulting mixture have an average anti-pathogen inactivating compound antibody binding capacity (ABC) of between about 25,000 and 70,000.

46. The method of claim 1, wherein the red blood cells of the resulting mixture have an average anti-pathogen inactivating compound antibody binding capacity (ABC) of between about 35,000 and 45,000.

47. The method of claim 1, wherein the red blood cells of the resulting mixture have less than 1% hemolysis following step (b).

48. The method of claim 1, wherein the red blood cells of the resulting mixture have less than 1% hemolysis at a time of 42 days at 4° C. following step (b).

49. The method of claim 1, wherein the red blood cells of the resulting mixture have a Packed Cell Volume of greater than 50% following step (b).

50. The method of claim 1, wherein the red blood cells of the resulting mixture have a Packed Cell Volume of greater than 50% at a time of 42 days at 4° C. following step (b).

51. The method of claim 1, wherein the red blood cells of the resulting mixture have a Median Corpuscular Fragility value greater than 140 mOsm after 42 days at 4° C. following step (b).

52. The method of claim 8, wherein mixing the base and the quencher results in a salt form of the quencher.

53. The method of claim 52, wherein the quencher is glutathione, and the salt form is potassium glutathione or sodium glutathione.

54. The method of claim 1, wherein the mixture of step (a) after addition of the treatment solution or diluent solution and prior to step (b) comprises less than about 75 mM chloride ion.

55. The method of claim 1, wherein the composition comprising red blood cells in step (a) has a Packed Cell Volume of between about 70% and 90%.

56. The method of claim 1, wherein the composition comprising red blood cells in step (a) has a Packed Cell Volume of between about 75% and 85%.

57. The method of claim 1, wherein the composition comprising red blood cells in step (a) has a Packed Cell Volume of between about 50 and 70%.

58. The method of claim 1, wherein the composition comprising red blood cells in step (a) has a Packed Cell Volume of between about 55 and 75%.

59. The method of claim 1, wherein the composition comprising red blood cells in step (a) has a Packed Cell Volume of between about 30 and 50%.

60. The method of claim 1, wherein the composition comprising red blood cells in step (a) has a Packed Cell Volume of between about 35 and 45%.

61. The method of claim 1, wherein the red blood cells in step (a) have been leukoreduced.

62. The method of claim 1, the red blood cells in step (a) have not been leukoreduced.

63. The method of claim 1, wherein the resulting mixture of step (a) has a pH at 37° C. of about 6.0 to 7.5.

64. The method of claim 1, wherein the resulting mixture of step (a) has a pH at 37° C. of about 6.8.

65. The method of claim 1, wherein the concentration of the pathogen-inactivating compound in the resulting mixture of step (a) is sufficient to inactivate at least 1 log of a pathogen in the red blood cell composition, if present.

66. The method of claim 1, wherein the treatment inactivates at least 1 log of a pathogen contaminant in the red blood cell composition, if present.

67. A method of reducing dehydration in a red blood cell composition wherein the composition is a mixture comprising (a) a quencher capable of reacting with a pathogen-inactivating compound, (b) about 0.5 to 1.5 equivalents of base, wherein an equivalent means a molar amount that is equivalent to the molar amount of quencher in the mixture, (c) red blood cells, and (d) a treatment solution or diluent solution; wherein the treatment solution or diluent solution comprises one or more of dextrose, adenine, mannitol, citrate, and citric acid; and wherein the red blood cell composition comprises between about 40 mM and 100 mM chloride ion; the method comprising replacing the solution in the mixture with a final additive solution, such that the concentration of the quencher in the mixture is decreased to less than about 10 mM; wherein the level of dehydration of the red blood cell composition is decreased relative to the level of dehydration of a red blood cell composition comprising (a), (c), (d), and 2.0 or greater equivalents of base and in which the solution in the mixture has not been replaced with a final additive solution.

68. The method of claim 67, wherein the quencher comprises cysteine or a derivative of cysteine.

69. The method of claim 67, wherein the quencher is glutathione or a pharmaceutically acceptable salt thereof.

70. The method of claim 67, wherein the quencher is glutathione monosodium salt.

71. The method of claim 67, wherein the concentration of the quencher is decreased to less than about 8 mM.

72. The method of claim 67, wherein the concentration of the quencher is decreased to less than about 6 mM.

73. The method of claim 67, wherein the red blood cells of the mixture after decreasing the concentration of the quencher have less than 1% hemolysis.

74. The method of claim 73, wherein the red blood cells of the mixture after decreasing the concentration of the quencher have less than 1% hemolysis at a time of 42 days at 4° C.

75. The method of claim 67, wherein the red blood cells of the mixture after decreasing the concentration of the quencher have a Packed Cell Volume of greater than 50%.

76. The method of claim 75, wherein the red blood cells of the mixture after decreasing the concentration of the quencher have a Packed Cell Volume of greater than 50% at a time of 42 days at 4° C.

77. The method of claim 67, wherein the red blood cells of the mixture after decreasing the concentration of the quencher have a Median Corpuscular Fragility value greater than 140 after 42 days at 4° C.

* * * * *